US008022094B2

(12) United States Patent
Ini et al.

(10) Patent No.: US 8,022,094 B2
(45) Date of Patent: Sep. 20, 2011

(54) CARVEDILOL PHOSPHATE

(75) Inventors: Santiago Ini, Haifa (IL); Sigalit Levi, Modi'in (IL); Michal Rafilovich, Petach-Tikva (IL); Judith Aronhime, Rehovot (IL); Mili Abramov, Givataim (IL); Ron Bar-Shavit, Ariel (IL); Eran Turgeman, Herzelia (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 11/824,536

(22) Filed: Jun. 28, 2007

(65) Prior Publication Data

US 2008/0125476 A1    May 29, 2008

Related U.S. Application Data

(60) Provisional application No. 60/817,634, filed on Jun. 28, 2006, provisional application No. 60/837,878, filed on Aug. 14, 2006, provisional application No. 60/843,818, filed on Sep. 11, 2006, provisional application No. 60/845,632, filed on Sep. 18, 2006, provisional application No. 60/845,879, filed on Sep. 19, 2006, provisional application No. 60/846,699, filed on Sep. 21, 2006, provisional application No. 60/847,587, filed on Sep. 26, 2006, provisional application No. 60/848,514, filed on Sep. 28, 2006, provisional application No. 60/851,366, filed on Oct. 12, 2006, provisional application No. 60/853,505, filed on Oct. 19, 2006, provisional application No. 60/857,716, filed on Nov. 7, 2006, provisional application No. 60/859,764, filed on Nov. 16, 2006, provisional application No. 60/878,914, filed on Jan. 4, 2007, provisional application No. 60/897,083, filed on Jan. 23, 2007, provisional application No. 60/899,815, filed on Feb. 5, 2007, provisional application No. 60/903,696, filed on Feb. 26, 2007, provisional application No. 60/927,098, filed on Apr. 30, 2007, provisional application No. 60/927,099, filed on Apr. 30, 2007.

(51) Int. Cl.
*A01N 43/38* (2006.01)
*C07D 209/82* (2006.01)

(52) U.S. Cl. ........................................ 514/411; 548/444
(58) Field of Classification Search .......................... None
See application file for complete search history.

(56) References Cited

U.S. PATENT DOCUMENTS

| 4,438,128 A | 3/1984 | Wiedemann et al. |
| 4,503,067 A | 3/1985 | Wiedemann et al. |
| 4,697,022 A | 9/1987 | Leinert |
| 4,767,784 A | 8/1988 | Zolss et al. |
| 4,824,963 A | 4/1989 | Leinert |
| 4,985,454 A | 1/1991 | Leinert |
| 4,990,668 A | 2/1991 | Mai et al. |
| 5,071,868 A | 12/1991 | Leinert |
| 5,760,069 A | 6/1998 | Lukas-Laskey et al. |
| 5,902,821 A | 5/1999 | Lukas-Laskey et al. |
| 6,022,562 A | 2/2000 | Autant et al. |
| 6,699,997 B2 | 3/2004 | Hildesheim et al. |
| 6,710,184 B2 | 3/2004 | Kor et al. |
| 6,730,326 B2 | 5/2004 | Beyer et al. |
| 6,777,559 B2 | 8/2004 | Scalone et al. |
| 7,056,942 B2 | 6/2006 | Hildesheim et al. |
| 7,126,008 B2 | 10/2006 | Hildesheim et al. |
| 7,169,935 B2 | 1/2007 | Scalone et al. |
| 2002/0143045 A1 | 10/2002 | Hildesheim et al. |
| 2003/0166702 A1 | 9/2003 | Kor et al. |
| 2004/0127723 A1 | 7/2004 | Scalone et al. |
| 2004/0152756 A1 | 8/2004 | Chen et al. |
| 2004/0171665 A1 | 9/2004 | Kor et al. |
| 2004/0198812 A1 | 10/2004 | Bubendorf et al. |
| 2004/0225132 A1 | 11/2004 | Hildesheim et al. |
| 2005/0240027 A1 | 10/2005 | Brook et al. |
| 2005/0277689 A1 | 12/2005 | Brook et al. |
| 2006/0148878 A1 | 7/2006 | Bubendorf et al. |
| 2006/0167077 A1 | 7/2006 | Hercek et al. |
| 2006/0182804 A1 | 8/2006 | Burke et al. |
| 2006/0270858 A1 | 11/2006 | Chhabada et al. |
| 2007/0027202 A1 | 2/2007 | Kumar et al. |
| 2007/0055069 A1 | 3/2007 | Ramanjaneyulu et al. |
| 2007/0112054 A1 | 5/2007 | Knipp et al. |
| 2007/0191456 A1 | 8/2007 | Tarur et al. |
| 2007/0197797 A1 | 8/2007 | Harrington |

FOREIGN PATENT DOCUMENTS

| EP | 0893440 | 1/1999 |
| EP | 0 918 055 | 5/1999 |
| IN | 929/MUM/2007 | 5/2007 |
| WO | WO 99/05105 | 2/1999 |
| WO | WO 01/35938 | 5/2001 |
| WO | WO 03/059807 | 7/2003 |
| WO | WO 2004/041783 | 5/2004 |
| WO | WO 2004/094378 | 11/2004 |
| WO | WO 2005/051383 | * 11/2004 |
| WO | WO 2005/021504 | 3/2005 |
| WO | WO 2005/080329 | 9/2005 |
| WO | WO 2005/113502 | 12/2005 |

(Continued)

OTHER PUBLICATIONS

Newman et al., DDT vol. 8, Oct. 2003, p. 898-90.*

(Continued)

*Primary Examiner* — Sun Jae Loewe
(74) *Attorney, Agent, or Firm* — Kenyon & Kenyon LLP

(57) ABSTRACT

The invention encompasses novel amorphous and crystalline forms of carvedilol phosphate, carvedilol hydrogen phosphate, and carvedilol dihydrogen phosphate as well as methods of making the novel amorphous and crystalline forms. Also disclosed are pharmaceutical compositions comprising the novel amorphous and crystalline forms and uses thereof.

19 Claims, 60 Drawing Sheets

FOREIGN PATENT DOCUMENTS

| | | |
|---|---|---|
| WO | WO 2005/115981 | 12/2005 |
| WO | WO 2006/061364 | 6/2006 |
| WO | WO 2007/077111 | 7/2007 |
| WO | WO 2007/097504 | 8/2007 |
| WO | WO 2007/144900 | 12/2007 |

OTHER PUBLICATIONS

Chawla et al., CRIPS vol. 5, No. 1, Jan.-Mar. 2004, p. 9-12.*
Brittain, Polymorphism in Pharmaceutical Solids, vol. 95, p. 228-229.*
Express-Pharma-Online (http://www.expresspharmaonline.com/20031023/edit02.shtml).*
Brittain et al. #2 "Effects of pharmaceutical processing on drug polymorphs and solvates" in Polymorphism in Pharmaceutical Solids, vol. 95, p. 331-361.*
Brittain, "Polymorphism in Pharmaceutical Sciences." 183-226 (1999).
Brittain, "Polymorphism in Pharmaceutical Sciences." 1-2, 178-179, 185-186, 199-201, 219, 235, 237-238(1999).
Bryn et al., Solid-State Chemistry of Drugs, SSCI, Inc., Second edition, p. 62-63 (1999).
Carey, et al. "Advanced Organic Chemistry" Third Edition, Part A: Structure and Mechanisms; Plenum Press, pp. 232-239 (1993).
Chen et al. "Synthesis and Crystal Structure of Carvedilol" *Jiegou Huaxue*, vol. 17, No. 5, Sep. 1998, pp. 325-328.
Eagleson, "Concise Encyclopedia Chemistry," p. 872-873 (1993).
Haleblian et al., "Pharmaceutical Applications of Polymorphism", *Journal of Pharmaceutical Sciences*, vol. 58, No. 8, pp. 911-929, Jul. 1969.
Haleblian, "Characterization of Habits and Crystalline Modification of Solids and Their Pharmaceutical Applications", *Journal of Pharmaceutical Sciences*, vol. 64, No. 8, pp. 1269-1288, Jul. 1975.
Japanese Office Action from related Japanese Patent Application No. 2002-504998, mailed May 7, 2008, with English translation.
Offer of Information, dated Sep. 19, 2007, from related Japanese Patent Application No. 2002-504998 with translation.
Rouhi et al., "The Right Stuff," Chemical & Engineering News, p. 31-35 (2003).
"X-Ray Diffraction," U.S. Pharmacopia #23, National Formulatry #18, p. 1843-1844 (1995).
Wall, "Pharmaceutical Applications of Drug Crystal Studies", *Pharmaceutical Manufacturing*, vol. 3, No. 2, pp. 33-42, Feb. 1986.

* cited by examiner

Solid-state $^{13}$C-NMR spectrum of carvedilol dihydrogen phosphate Form L.

Solid-state $^{13}$C-NMR spectrum of carvedilol dihydrogen phosphate Form L.

Solid-state $^{13}$C-NMR spectrum of carvedilol dihydrogen phosphate Form L1.

Solid-state $^{13}$C-NMR spectrum of carvedilol dihydrogen phosphate Form P.

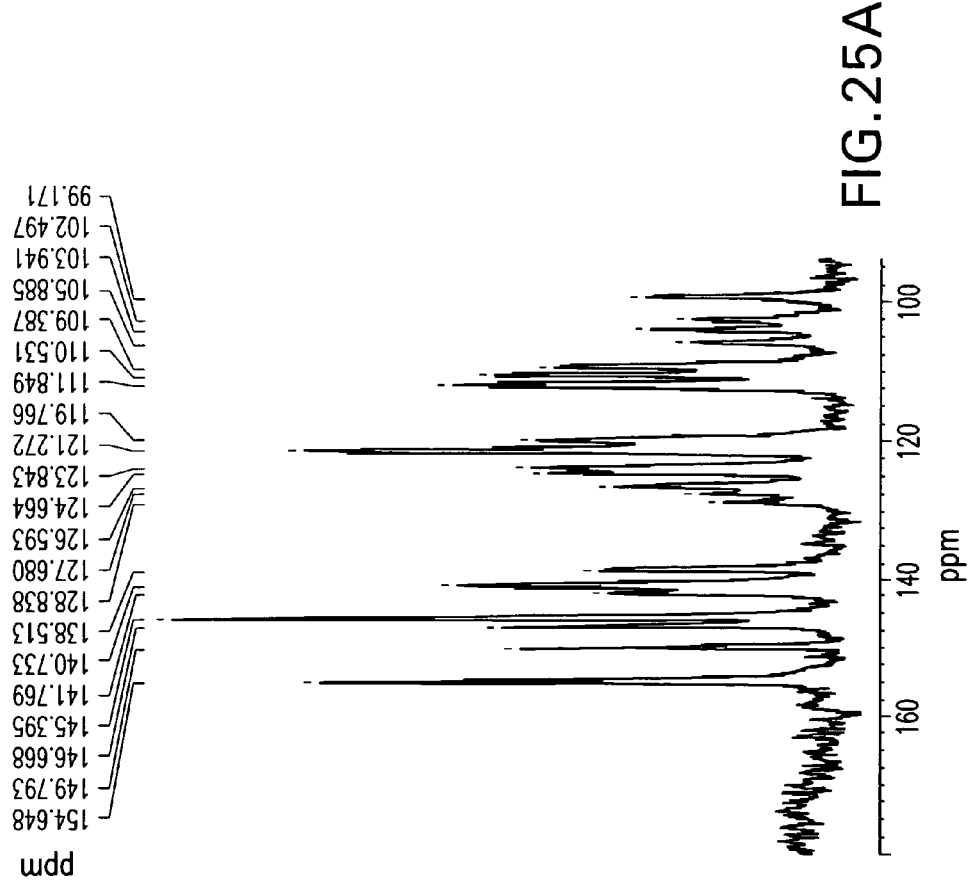

Solid-state $^{13}$C-NMR spectrum of carvedilol dihydrogen phosphate Form R.

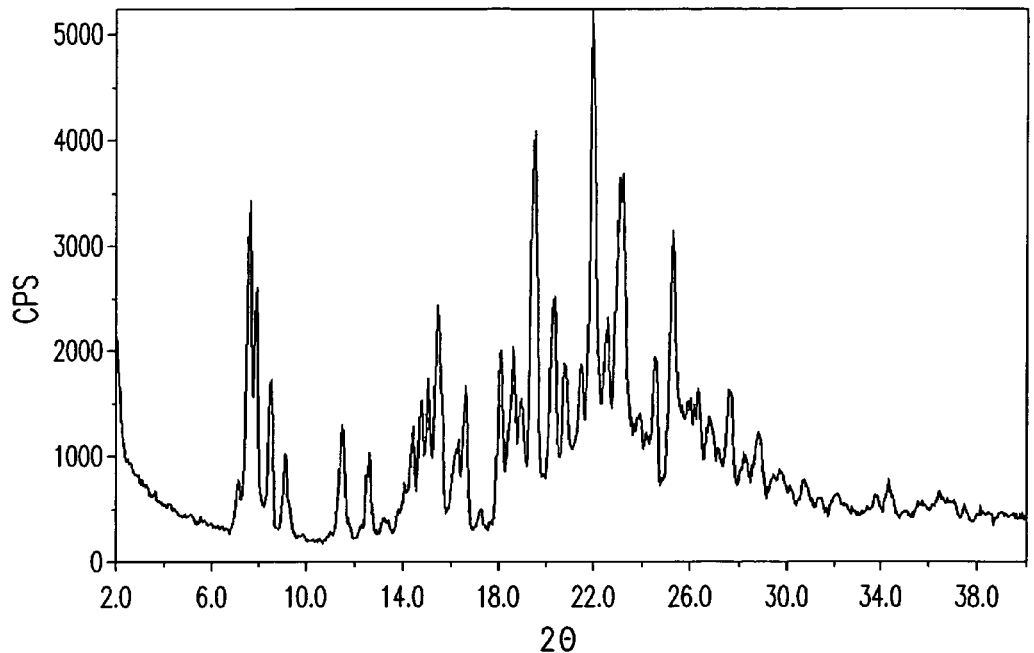
FIG.31 Powder X-ray diffractogram for carvedilol dihydrogen phosphate Form Y.
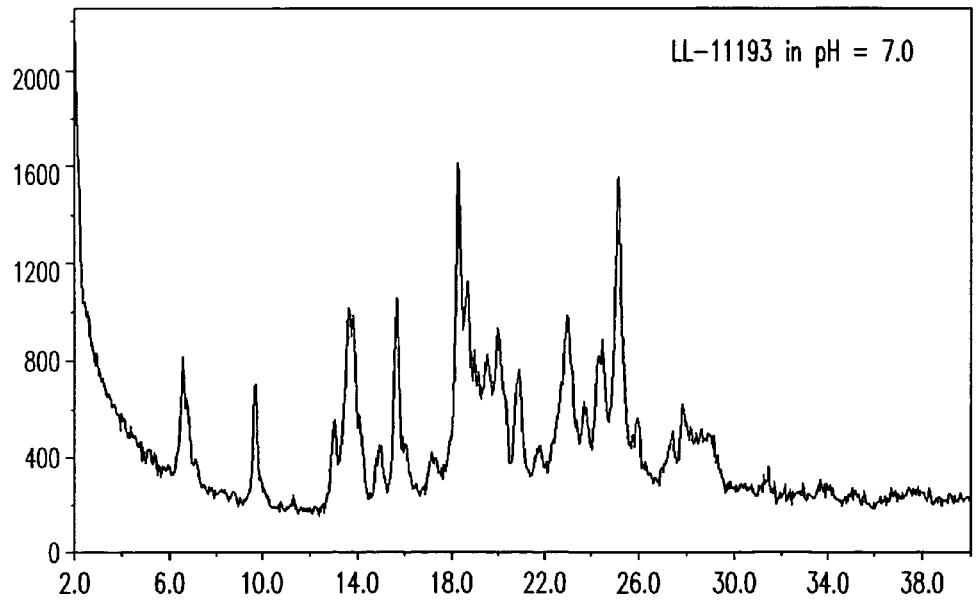
FIG.32 Powder X-ray diffractogram of carvedilol phosphate salt Form W (example 1).

Powder X-ray diffractogram for the amorphous form of carvedilol dihydrogen phosphate.

Calculated Powder X-ray diffractogram of carvedilol phosphate hemil-ethanolate Form F2 (example 1).

Sem images of the Form I.

Sem images of the Form IV.

Microscope image of the Form I.

CARVEDILOL PHOSPHATE

CROSS REFERENCE TO RELATED APPLICATIONS

This application claims the benefits of U.S. Provisional Patent Applications Nos. 60/817,634, filed 28 Jun. 2006; 60/837,878, filed 14 Aug. 2006; 60/843,818, filed 11 Sep. 2006; 60/845,632, filed 18 Sep. 2006; 60/845,879, filed 19 Sep. 2006; 60/846,699, filed 21 Sep. 2006; 60/847,587, filed 26 Sep. 2006; 60/848,514, filed 28 Sep. 2006; 60/851,366, filed 12 Oct. 2006; 60/853,505, filed 19 Oct. 2006; 60/857,716, filed 7 Nov. 2006; 60/859,764, filed 16 Nov. 2006; 60/878,914, filed 4 Jan. 2007; 60/897,083, filed 23 Jan. 2007; 60/899,815, filed 5 Feb. 2007; 60/903,696, filed 26 Feb. 2007; 60/927,098, filed 30 Apr. 2007; 60/927,099, filed 30 Apr. 2007; the contents of all of which are incorporated herein by reference.

FIELD OF THE INVENTION

The invention encompasses carvedilol phosphate and solid states thereof.

BACKGROUND OF THE INVENTION

Carvedilol, (±)-1-(Carbazol-4-yloxy)-3-[[2-(o-methoxyphenoxy)ethyl]amino]-2-propanol, is a nonselective β-adrenergic blocker with $\alpha_1$-blocking activity. Carvedilol is a racemic mixture having the following structural formula:

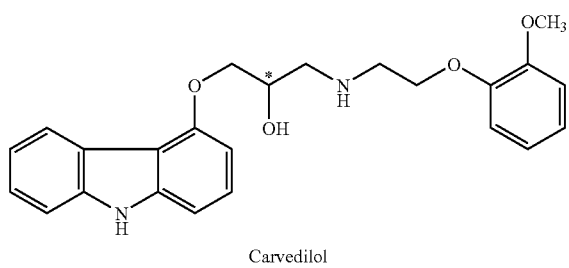

Carvedilol

Carvedilol is the active ingredient in COREG®, which is indicated for the treatment of congestive heart failure and for the management of hypertension. Since carvedilol is a multiple-action drug, its beta-blocking activity affects the response to certain nerve impulses in parts of the body. As a result, beta-blockers decrease the heart's need for blood and oxygen by reducing its workload. Carvedilol is also known to be a vasodilator resulting primarily from alpha-adrenoceptor blockade. The multiple actions of carvedilol are responsible for the antihypertensive efficacy of the drug and for its effectiveness in managing congestive heart failure.

U.S. Pat. No. 4,503,067 ("'067 patent") discloses a class of carbazolyl-(4)-oxypropanolamine compounds, including carvedilol. See '067 patent, col. 1, l. 15 to col. 2, l. 3. The '067 patent also discloses the conversion of the compounds to their pharmacologically acceptable salts, by reacting the compound with "an equivalent amount of an inorganic or organic acid," such as phosphoric acid. See id. at col. 4, ll. 23-29.

U.S. publication No. 2005/0240027 ("'027 publication") and U.S. publication No. 2005/0277689 ("'689 publication") each disclose that carvedilol has "relatively low solubility" (<1 μg/mL) in alkaline media, and that its solubility increases with decreasing pH, up to about 100 μg/mL. See '027 publication, p. 1, 7; '689 publication, p. 1, 7. These publications also disclose solid and crystalline forms of carvedilol salts, as well as solvates thereof. See, e.g., '027 publication, p. 3, 51; '689 publication, p. 5, 169.

The discovery of new salt forms of carvedilol is needed in order to have greater aqueous solubility and also greater chemical stability.

Solid state physical properties of a pharmaceutical compound can be influenced by controlling the conditions under which the compound is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state property of a pharmaceutical compound is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. The solid state form of a compound may also affect its behavior on compaction and its storage stability.

These practical physical characteristics are influenced by the conformation and orientation of molecules in the unit cell, which defines a particular polymorphic form of a substance. The polymorphic form may give rise to thermal behavior different from that of the amorphous material or another polymorphic form. Thermal behavior is measured in the laboratory by such techniques as capillary melting point, thermogravimetric analysis (TGA) and differential scanning calorimetric (DSC) and can be used to distinguish some polymorphic forms from others. A particular polymorphic form may also give rise to distinct spectroscopic properties that may be detectable by powder X-ray crystallography, solid state $^{13}C$ NMR spectrometry or infrared spectrometry.

One of the most important physical properties of a pharmaceutical compound, which can form polymorphs or solvates, is its solubility in aqueous solution, particularly the solubility in gastric juices of a patient. Other important properties relate to the ease of processing the form into pharmaceutical dosages, as the tendency of a powdered or granulated form to flow and the surface properties determine whether crystals of the form will adhere to each other when compacted into a tablet.

The discovery of new solid states of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic.

SUMMARY OF THE INVENTION

Carvedilol Phosphate

In one embodiment, the invention encompasses carvedilol phosphate in an amorphous form. The invention also encompasses pharmaceutical compositions comprising amorphous carvedilol phosphate as well as methods of treatment using such pharmaceutical compositions. X-ray diffractogram is substantially shown in FIG. 1.

In another embodiment, the invention encompasses a process for preparing carvedilol phosphate in an amorphous form comprising: (a) providing a solution of carvedilol, phosphoric acid, and ethanol; (b) optionally adding water to the solution to accelerate precipitation of the carvedilol phosphate; and (c) recovering the carvedilol phosphate in amorphous form.

Carvedilol Hydrogen Phosphate

In one embodiment, the invention encompasses a crystalline form of carvedilol hydrogen phosphate, referred to herein as Form G, and characterized by data selected from the group consisting of: X-ray powder diffraction reflections at about: 6.5, 9.7, 13.0, 16.0 and 17.8 degrees two theta±0.2 degrees two theta; a solid-state $^{13}$C-NMR spectrum having chemical shift resonances at about: 145.8, 141.7 and 110.8±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about: 43.8, 39.7 and 8.8±0.1 ppm; any five peaks selected from the following list of PXRD peaks at about: 6.5, 9.7, 13.0, 13.5, 16.0, 17.8, 22.8 and 23.2±0.2 degrees two theta; X-ray powder diffraction reflections at about: 6.5, 9.7, 13.5, 16.0 and 17.8 degrees two theta±0.2 degrees two theta; X-ray powder diffraction reflections at about: 6.5, 9.7, 16.0, 18.4 and 23.2 degrees two theta±0.2 degrees two theta; X-ray diffractogram substantially shown in FIG. 2; the solid-state $^{13}$C-NMR substantially shown in FIG. 3 or 3a.

In another embodiment, the invention encompasses a crystalline form of carvedilol hydrogen phosphate, referred to herein as Form H, and characterized by data selected from the group consisting of: X-ray powder diffraction reflections at about: 6.4, 6.6, 9.4, 14.5 and 15.4 degrees two theta±0.2 degrees two theta; X-ray powder diffraction reflections at about: 6.6, 9.7, 13.0, 13.8 and 15.6 degrees two theta±0.2 degrees two theta; any five peaks selected from the following list of PXRD peaks at about: 6.5, 6.8, 9.6, 13.0, 13.6, 15.6, 17.5 and 28.7±0.2 degrees two theta; X-ray powder diffraction reflections at about: 6.5, 9.6, 13.0, 13.6 and 18.7 degrees two theta±0.2 degrees two theta; X-ray powder diffraction reflections at about: 6.5, 9.6, 13.6, 18.7 and 20.2 degrees two theta±0.2 degrees two theta; a solid-state $^{13}$C-NMR spectrum having chemical shift resonances at about: 146.3, 142.6 and 139.1±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 34, 30.3 and 26.8±0.1 ppm; X-ray diffractogram substantially shown in FIG. 4 or 5; solid-state $^{13}$C-NMR substantially shown in FIG. 6 or 6a.

In another embodiment, the invention encompasses a crystalline form of carvedilol hydrogen phosphate, referred to herein as Form K, and characterized by data selected from the group consisting of: X-ray powder diffraction reflections at about: 6.3, 9.8, 12.7, 13.2 and 16.9 degrees two theta±0.2 degrees two theta; X-ray diffractogram substantially shown in FIG. 7; any five peaks selected from the following list of PXRD peaks at about: 6.3, 9.8, 12.7, 13.2, 16.3, 16.9, 18.3 and 19.0±0.2 degrees two theta; X-ray powder diffraction reflections at about: 6.3, 9.8, 16.9, 18.3 and 23.2 degrees two theta±0.2 degrees two theta; X-ray powder diffraction reflections at about: 6.3, 9.8, 14.9, 20.1 and 28.2 degrees two theta±0.2 degrees two theta.

In another embodiment, the invention encompasses a crystalline form of carvedilol dihydrogen phosphate, referred to herein as Form Q, characterized by data selected from the group consisting of: X-ray powder diffraction reflections at about: 6.2, 7.3, 14.5, 17.5 and 21.3 degrees two theta±0.2 degrees two theta; X-ray diffractogram substantially shown in FIG. 8.

In another embodiment, the invention encompasses an amorphous form of carvedilol hydrogen phosphate. This amorphous form is substantially depicted in XRD diffractograms shown in FIG. 9 or 10.

The invention also encompasses pharmaceutical compositions comprising the crystalline forms and the amorphous form of carvedilol hydrogen phosphate as well as methods of treatment using such pharmaceutical compositions.

In another embodiment, the invention encompasses processes for preparing the crystalline forms and the amorphous form of carvedilol hydrogen phosphate.

Carvedilol Dihydrogen Phosphate

In one embodiment, the invention encompasses a process for preparing crystalline carvedilol dihydrogen phosphate Form I, characterized by data selected from the group consisting of: X-ray powder diffraction reflections at about: 7.0, 8.0, 9.2, 11.4 and 16.0 degrees two theta±0.2 degrees two theta; a solid-state $^{13}$C-NMR spectrum having chemical shift resonances at about 154.5, 146.5, 139.7 and 122.1±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 50.7, 42.7, 35.9 and 18.3±0.1 ppm, comprising: combining carvedilol, phosphoric acid and a solvent selected from the group consisting of $C_1$-$C_8$ alcohols, $C_5$-$C_{10}$ aliphatic hydrocarbons, $C_{6-12}$ aromatic hydrocarbons, $C_3$-$C_7$ ketones, $C_4$-$C_8$ ethers, $C_3$-$C_7$ esters and acetonitrile and precipitating carvedilol dihydrogen phosphate Form I from the reaction mixture. X-ray diffractogram substantially shown in FIG. 11; solid-state $^{13}$C-NMR substantially shown in FIG. 12.

In another embodiment, the invention encompasses a crystalline form of carvedilol dihydrogen phosphate, referred to herein as Form L, characterized by data selected from the group consisting of: X-ray powder diffraction reflections at about: 4.6, 7.5, 8.7, 11.6 and 15.6 degrees two theta±0.2 degrees two theta; a solid-state $^{13}$C-NMR spectrum having chemical shift resonances at about 156.6, 150.3 and 102.5±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 54.1 and 47.8 and 0.0±0.1 ppm; X-ray diffractogram shown in FIG. 13; solid-state $^{13}$C-NMR shown in FIGS. 14 and/or 14a; any five peaks selected from the following list of PXRD peaks at about: 4.6, 7.5, 8.7, 11.6 13.4, 15.6 and 19.4±0.2 degrees two theta; X-ray powder diffraction reflections at about: 4.6, 7.5, 8.7, 11.6 and 15.0 degrees two theta±0.2 degrees two theta; X-ray powder diffraction reflections at about: 4.6, 7.5, 8.7, 15.0 and 22.9 degrees two theta±0.2 degrees two theta.

In another embodiment, the invention encompasses a crystalline form of carvedilol dihydrogen phosphate, referred to herein as Form L1, characterized by data selected from the group consisting of: X-ray powder diffraction reflections at about: 4.6, 8.7, 11.6, 14.6 and 15.3 degrees two theta±0.2 degrees two theta; a solid-state $^{13}$C-NMR spectrum having chemical shift resonances at about 156.6, 150.3 and 148.4±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 53.2, 46.9 and 45.0±0.1 ppm; X-ray diffractogram substantially shown in FIG. 15; solid-state $^{13}$C-NMR substantially shown in FIGS. 16 and/or 16a; PXRD peaks at about: 4.6, 7.4, 8.7, 11.6 14.6, 15.3 and 19.4±0.2 degrees two theta; PXRD peaks at about 4.6, 7.4, 8.7, 13.6 and 15.3 degrees two theta±0.2 degrees two theta; PXRD peaks at about 4.6, 7.4, 8.7, 11.6 and 17.4; PXRD peaks at about 4.6, 7.4, 8.7, 15.3 and 17.4 degrees two theta±0.2 degrees two theta.

In another embodiment, the invention encompasses a crystalline form of carvedilol dihydrogen phosphate, referred to herein as Form N, characterized by data selected from the group consisting of: X-ray powder diffraction reflections at about: 6.0, 6.9, 15.2, 16.3 and 17.4 degrees two theta±0.2 degrees two theta; a solid-state $^{13}$C-NMR spectrum having chemical shift resonances at about 154.4, 146.9 and 138.4±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 52.9, 45.4 and 36.9±0.1 ppm; a solid-state $^{13}$C-NMR spectrum having chemical shift resonances at about 154.4, 146.9, 138.4 and 110.9±0.2 ppm; a solid-state $^{13}$C NMR spectrum having chemical shift differences between the lowest ppm resonance in the chemical shift area of 100 to 180 ppm and another in the chemical shift area of 100 to 180 ppm of about 52.9, 45.4, 36.9 and 9.4±0.1 ppm; X-ray diffractogram substantially shown in FIGS. 17 and 18; solid-state $^{13}$C-NMR substantially shown in FIGS. 19 and/or 19a; X-ray powder diffraction reflections at about: 6.0, 6.9, 13.7 15.2 and 18.1 degrees two theta±0.2 degrees two theta; X-ray powder diffraction reflections at about: 6.0, 6.9, 13.7, 15.2 and 17.4±0.2 degrees two theta.

In another embodiment, the invention encompasses a crystalline form of carvedilol dihydrogen phosphate, referred to herein as Form O, characterized by data selected from the group consisting of: X-ray powder diffraction reflections at about: 6.1, 12.2, 12.9, 16.2 and 18.0 degrees two theta±0.2 degrees two theta; X-ray diffractogram shown in FIG. 20.

In another embodiment, the invention encompasses a crystalline form of carvedilol dihydrogen phosphate, referred to herein as Form P, characterized by data selected from the group consisting of: X-ray powder diffraction reflections at about: 5.3, 10.4, 16.8, 26.0 and 31.8 degrees two theta±0.2 degrees two theta; a solid-state $^{13}$C-NMR spectrum having chemical shift resonances at about 154.7, 146.6 and 122.2±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 54.7, 46.6 and 22.2±0.1 ppm; X-ray diffractogram shown in FIG. 21; solid-state $^{13}$C-NMR shown in FIGS. 22 and/or 22a; any five peaks selected from the following list of PXRD peaks at about: 5.3, 10.4, 14.5, 16.8, 17.8, 26.0 and 31.8±0.2 degrees two theta; X-ray powder diffraction reflections at about: 5.3, 10.4, 15.2, 17.8 and 22.5 degrees two theta±0.2 degrees two theta; Form P can also be characterized by X-ray powder diffraction reflections at about: 5.3, 14.5, 15.2, 16.8 and 17.3 degrees two theta±0.2 degrees two theta; Form P can also be characterized by X-ray powder diffraction reflections at about: 5.3, 10.4, 14.5, 15.2 and 17.8 degrees two theta±0.2 degrees two theta; Form P can also be characterized by X-ray powder diffraction reflections at about: 5.3, 14.5, 15.2, 17.8 and 20.1 degrees two theta±0.2 degrees two theta.

In another embodiment, the invention encompasses a crystalline form of carvedilol dihydrogen phosphate, referred to herein as Form F, characterized by data selected from: X-ray powder diffraction reflections at about: 7.7, 8.7, 16.8 and 22.8 degrees two theta±0.2 degrees two theta; X-ray powder diffraction reflections at about: 7.6, 8.6, 16.7 and 22.8 degrees two theta±0.2 degrees two theta; X-ray powder diffraction reflections at about: 7.7, 8.7, 16.8, 22.8 and 26.5 degrees two theta±0.2 degrees two theta; X-ray powder diffraction reflections at about: 7.6, 8.6, 16.7, 22.8 and 26.5 degrees two theta±0.2 degrees two theta; a solid-state $^{13}$C-NMR spectrum having chemical shift resonances at about 149.8, 145.4 and 140.7±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 50.6, 46.2 and 41.5±0.1 ppm; a solid-state $^{13}$C-NMR spectrum having chemical shift resonances at about 149.8, 145.4, 138.5 and 140.7±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 50.6, 46.2, 39.3 and 41.5±0.1 ppm; X-ray diffractogram shown in FIG. 23 or 24; solid-state $^{13}$C-NMR shown in FIGS. 25 and/or 25a; X-ray powder diffraction reflections at about: 7.7, 8.7, 13.5, 15.2 and 22.9 degrees two theta±0.2 degrees two theta; X-ray powder diffraction reflections at about: 7.6, 8.6, 13.4, 15.1 and 22.8 degrees two theta±0.2 degrees two theta; X-ray powder diffraction reflections at about: 7.7, 13.5, 15.2, 18.3 and 18.9 degrees two theta±0.2 degrees two theta; X-ray powder diffraction reflections at about: 7.6, 13.4, 15.1, 18.2 and 18.8 degrees two theta±0.2 degrees two theta; X-ray powder diffraction reflections at about: 7.7, 13.5, 15.2, 17.2 and 21.5 degrees two theta±0.2 degrees two theta; X-ray powder diffraction reflections at about: 7.6, 13.4, 15.1, 17.1 and 21.4 degrees two theta±0.2 degrees two theta.

In another embodiment, the invention encompasses a crystalline form of carvedilol dihydrogen phosphate, referred to herein as Form F1, characterized by X-ray powder diffraction reflections at about: 7.6, 9.8, 10.9, 21.2 and 25.0 degrees two theta±0.2 degrees two theta; a solid-state $^{13}$C-NMR spectrum having chemical shift resonances at about 155.3, 145.3 and 127.7±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 52.6, 42.6 and 25±0.1 ppm; X-ray diffractogram shown in FIG. 26 or 27; solid-state $^{13}$C-NMR shown in FIGS. 28 and/or 28a; X-ray powder diffraction reflections at about: 7.6, 10.9, 13.3, 15.2 and 18.8 degrees two theta±0.2 degrees two theta; X-ray powder diffraction reflections at about: 7.6, 8.5, 9.8, 15.2 and 16.9±0.2 degrees two theta; X-ray powder diffraction reflections at about: 7.6, 9.8, 10.9, 14.7, 15.2 and 22.8±0.2 degrees two theta; X-ray powder diffraction reflections at about: 7.6, 8.5, 9.8, 13.3 and 15.2±0.2 degrees two theta.

In another embodiment, the invention encompasses a crystalline form of carvedilol dihydrogen phosphate, referred to herein as Form R, characterized by X-ray powder diffraction reflections at about: 5.8, 11.8, 16.8, 18.6 and 23.2 degrees two theta±0.2 degrees two theta; a solid-state $^{13}$C-NMR spectrum having chemical shift resonances at about 153.7, 147.9 and 122.8±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 51.0, 45.2 and 20.1±0.1 ppm; X-ray diffractogram shown in FIG. 29; solid-state $^{13}$C-NMR shown in FIGS. 30 and/or 30a; X-ray powder diffraction reflections at about: 5.8, 11.8, 15.5, 16.2 and 18.6 degrees two theta±0.2 degrees two theta; X-ray powder diffraction reflections at about: 5.8, 16.2, 18.6, 23.2 and 27.0 degrees two theta±0.2 degrees two theta; X-ray powder diffraction reflections at about: 5.8, 16.2, 16.8, 19.9 and 25.4 degrees two theta±0.2 degrees two theta.

In another embodiment, the invention encompasses a crystalline form of carvedilol dihydrogen phosphate, referred to herein as Form Y, characterized by X-ray powder diffraction reflections at about: 7.7, 7.9, 9.1, 16.6 and 19.5 degrees two theta±0.2 degrees two theta; X-ray powder diffraction reflections at about: 7.7, 8.5, 16.6, 19.5 and 20.3 degrees two theta; X-ray diffractogram as substantially shown in FIG. 31.

In another embodiment, the invention encompasses a crystalline form of carvedilol dihydrogen phosphate, referred to herein as Form W, characterized by data selected from the group consisting of: X-ray powder diffraction reflections at about: 6.6, 9.7, 13.8, 15.7 and 17.1 degrees two theta±0.2 degrees two theta; X-ray diffractogram is shown in FIG. 32.

In another embodiment, the invention encompasses an essentially amorphous form of carvedilol dihydrogen phosphate characterized by data selected from the group consisting of: a solid-state $^{13}$C-NMR spectrum having chemical shift resonances at about 154.6, 146.7 and 140.3±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 54.2, 46.3 and 39.9±0.1 ppm; solid-state $^{13}$C-NMR spectrum having broad chemical shift resonances at about 154.6, 146.7, 140.3 and 100.4±0.2 ppm; and a solid-state $^{13}$C-NMR spectrum having chemical shift differences between the lowest ppm resonance in the chemical shift area of 100 to 180 ppm and another in the chemical shift area of 100 to 180 ppm of about 54.2, 46.3, 39.9 and 0.0±0.1 ppm; X-ray diffractogram as substantially shown in FIG. 33; solid-state $^{13}$C-NMR spectrum as substantially shown in FIGS. 34 and/or 34a.

In another embodiment the present invention provides a crystalline form of Carvedilol phosphate salt, referred to herein as Form F2. Form F2 is characterized by an X-Ray powder diffraction pattern with peaks at about 7.4, 7.9, 8.5, 8.9 and 11.1±0.2 degrees two theta. The Calculated X-ray powder diffraction pattern of Carvedilol phosphate salt Form F2 is substantially depicted in FIG. 35. The structure was solved by direct methods for triclinic P-1 group with the unit cell parameters: a=13.281(3), b=14.315(3), c=16.406(4)Å, α=66.85(2), β=85.94(2) γ=65.44(4) [deg], and cell volume 2592.4(12)Å$^3$.

The invention also encompasses pharmaceutical compositions comprising the crystalline forms and the amorphous form of carvedilol dihydrogen phosphate as well as methods of treatment using such pharmaceutical compositions.

In another embodiment, the invention encompasses processes for preparing the crystalline forms and the amorphous form of carvedilol dihydrogen phosphate.

BRIEF DESCRIPTION OF THE FIGURES

FIG. 25a illustrate a solid-state $^{13}$C-NMR spectrum of carvedilol dihydrogen phosphate Form F in the chemical shift area of 100 to 180 ppm.

FIG. 31 illustrates a characteristic powder X-ray diffractogram for phosphate salt of carvedilol Form Y.

FIG. 32 illustrates a characteristic powder X-ray diffractogram for carvedilol dihydrogen phosphate Form W.

DETAILED DESCRIPTION OF THE INVENTION

Figure 1:
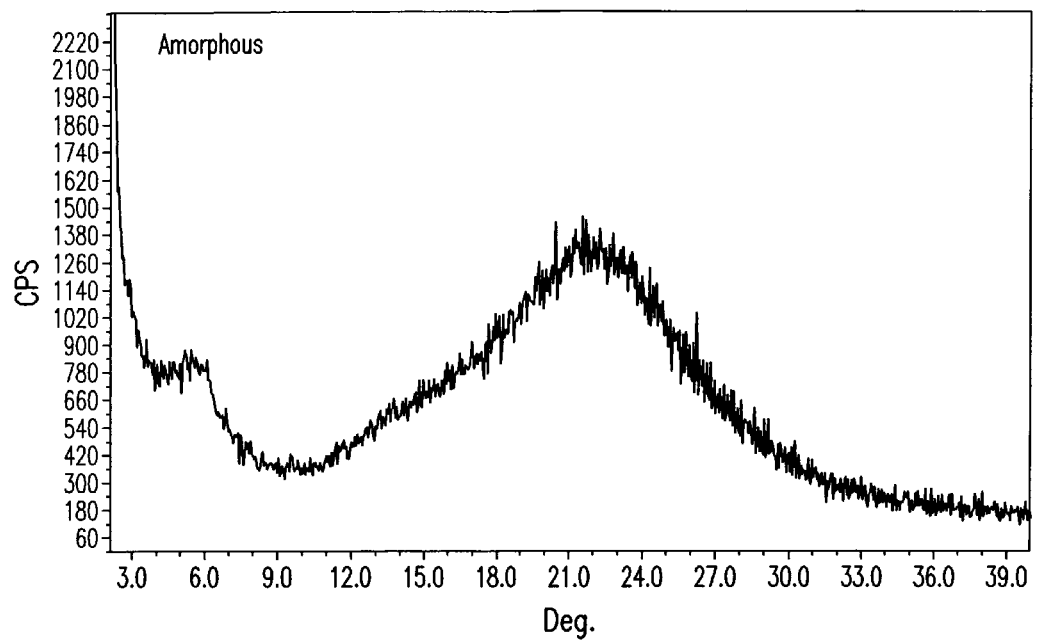
FIG. 1 is a PXRD for carvedilol phosphate amorphous form.

There is a need in the art for solid forms of carvedilol phosphate, carvedilol hydrogen phosphate, and carvedilol dihydrogen phosphate with increased solubility over the carvedilol free base. Increased solubility leads to improved bioavailability when the drug is administered to a patient, and thus allows for a reduction in the dosages required. The invention addresses this need by providing amorphous forms and crystalline forms of carvedilol phosphate, carvedilol hydrogen phosphate and carvedilol dihydrogen phosphate, which are more readily soluble than carvedilol free base. Also provided are processes for preparing the amorphous forms and crystalline forms of carvedilol phosphate, carvedilol hydrogen phosphate and carvedilol dihydrogen phosphate.

As used herein, unless otherwise defined, the term "carvedilol phosphate" refers to a tricarvedilol phosphate complex, in which carvedilol and phosphate are present in a molar ratio of about 3:1.

As used herein, the term "carvedilol hydrogen phosphate" refers to a carvedilol phosphate salt, in which carvedilol and phosphoric acid are present in a molar ratio of about 2:1.

As used herein, the term "carvedilol dihydrogen phosphate" refers to a carvedilol phosphate salt, in which carvedilol and phosphate are present in a molar ratio of about 1:1.

"Therapeutically effective amount" means the amount of a crystalline form that, when administered to a patient for treating a disease or other undesirable medical condition, is sufficient to have a beneficial effect with respect to that disease or condition. The "therapeutically effective amount" may vary depending on the crystalline form, the disease or condition and its severity, and the age, weight, etc., of the patient to be treated. Determining the therapeutically effective amount of a given crystalline form is within the ordinary skill of the art and requires no more than routine experimentation.

"Pharmaceutically acceptable" means a substance which is not biologically or otherwise undesirable, i.e., the substance can be administered to an individual without causing significant undesirable effects.

As used herein, the term "water content" refers to the content of water based upon the Loss on Drying method (the "LOD" method) as described in UPS 29-NF 24, official Aug. 1, 2006, Physical Test and Determinations, (731) LOSS ON DRYING or in Pharmacopeial Forum, Vol. 24, No. 1, p. 5438 (January-February 1998), the Karl Fisher assay for determining water content or thermogravimetric analysis (TGA). All percentages herein are by weight unless otherwise indicated. Those skilled in the art will also understand that the term "dihydrate" when used in reference to carvedilol dihydrogen phosphate describes carvedilol dihydrogen phosphate having a water content of between about 4.7-6.9% w/w. Those skilled in the art will also understand that the term "hemihydrate" when used in reference to carvedilol dihydrogen phosphate describes carvedilol dihydrogen phosphate having a water content of about 1.7-2.0% w/w.

As used herein, the term "GC measurement of residual solvent" refers to an automatic headspace gas-chromatographic system.

As used herein, "solvate" is meant to include any crystalline form which incorporates solvent in a level of more than about 1%.

Those skilled in the art will understand that the term "hemimethanolate" when used in reference to carvedilol dihydrogen phosphate describes carvedilol dihydrogen phosphate having a methanol content of between about 2.7-3.2% w/w.

Those skilled in the art will understand that the term "hemiethanolate" when used in reference to carvedilol dihydrogen phosphate describes carvedilol dihydrogen phosphate having an ethanol content of between about 4.4-4.7% w/w.

Those skilled in the art will understand that the term "isopropanol solvate" when used in reference to carvedilol dihydrogen phosphate describes carvedilol dihydrogen phosphate having an isopropanol content of between about 7.5-10.3% w/w.

Spray drying broadly refers to processes involving breaking up liquid mixtures into small droplets (atomization) and rapidly removing solvent from the mixture. In a typical spray drying apparatus, there is a strong driving force for evaporation of solvent from the droplets, which may be provided by providing a drying gas. Spray drying processes and equipment are described in Perry's Chemical Engineer's Handbook, pp. 20-54 to 20-57 (6th ed. 1984) and Remington: The Science and Practice of Pharmacy, 19th ed., vol. 1, pg. 1627, which are herein incorporated by reference.

By way of non-limiting example only, the typical spray drying apparatus comprises a drying chamber, atomizing means for atomizing a solvent-containing feed into the drying chamber, a source of drying gas that flows into the drying chamber to remove solvent from the atomized-solvent-containing feed, an outlet for the products of drying, and product collection means located downstream of the drying chamber. Examples of such apparatuses include Niro Models PSD-1, PSD-2 and PSD-4 (Niro A/S, Soeborg, Denmark). Typically, the product collection means includes a cyclone connected to the drying apparatus. In the cyclone, the particles produced during spray drying are separated from the drying gas and evaporated solvent, allowing the particles to be collected. A filter may also be used to separate and collect the particles produced by spray drying.

As used herein, the term chemical shift difference refers to the difference in chemical shift resonance between a reference chemical shift resonance and another chemical shift resonance in the same NMR spectrum. In the present patent application, the chemical shift differences were calculated by subtracting the lowest ppm resonance (reference chemical shift resonance) in the NMR spectrum of chemical shifts in the area of 100 to 180 ppm from another (observed) ppm resonance in the same NMR spectrum of chemical shifts in the area of 100 to 180 ppm. These chemical shift differences provide a measurement for a substance, for example carvedilol phosphate, of the present invention that compensates for a phenomenon in NMR spectroscopy wherein, depending on the instrumentation and calibration method used, a shift in the SS-NMR "footprint" is observed. This shift in the SS-NMR "footprint", having chemical shift resonances at a certain positions, is such that although the individual chemical shift resonances have altered, the distance between each chemical shift resonance and the next is retained.

Carvedilol Phosphate

In one embodiment, the invention provides an amorphous form of carvedilol phosphate. The amorphous form of carvedilol phosphate may be free of any crystalline form.

In another embodiment, the invention encompasses a process for preparing the amorphous form of carvedilol phosphate. The amorphous form of carvedilol phosphate can be prepared by precipitation from ethanol. Preferably, the carvedilol phosphate is prepared by precipitation from a mixture of ethanol and water.

Accordingly, the invention provides a method for preparing amorphous carvedilol phosphate comprising:
(a) precipitating amorphous carvedilol phosphate from a solution of carvedilol and phosphoric acid in a mixture of ethanol and water; and
(b) recovering the amorphous carvedilol phosphate.

In one preferred embodiment, the process comprises: (a) providing a solution of carvedilol, phosphoric acid, and ethanol; (b) optionally adding water to the solution to accelerate precipitation of the carvedilol phosphate; and (c) recovering the carvedilol phosphate in amorphous form.

The carvedilol and phosphoric acid in step (a) can be present in a molar ratio of about 5:1 to about 1:1, preferably about 4:1 to about 2:1, more preferably about 2.5:1 to about 3.5:1, and even more preferably about 3:1. The solution of step (a) may be prepared by combining carvedilol and ethanol to form a mixture and then slowly adding phosphoric acid to the mixture. The solution of step (a) may also be prepared by combining phosphoric acid and ethanol and then adding carvedilol or by adding carvedilol and phosphoric acid more or less simultaneously to ethanol.

The ingredients in step (a) may be heated in order to achieve dissolution. Stirring may also be employed to promote dissolution. In one embodiment, heating is carried out to about 60° C. to about reflux temperature, followed by cooling to a temperature of about 0° C. to about 30° C. Preferably, the ingredients in step (a) are heated to reflux (about 78° C. to 82° C.) and maintained at reflux for a period of time. More preferably, the ingredients in step (a) are maintained at reflux for about 5 to about 10 minutes, or for about 5 to about 100 minutes, optionally, with stirring.

If the solution of step (a) is heated, the solution is preferably cooled to about 20° C. to about 35° C., preferably to about room temperature (about 20-23° C.), before adding the water of step (b). Preferably, after water is added to the solution of step (a), the resulting mixture is stirred at about 20° C. to about 35° C., preferably at about room temperature (about 20-23° C.). More preferably, the mixture is stirred at about 20° C. to about 35° C. for about 4 to about 16 hours, or about 6 to about 12 hours, or about 8 to about 10 hours, or overnight.

In certain embodiments, the ratio of water to ethanol is about 3:1 to about 1:3, preferably about 2:1 to about 1:2, and more preferably about 1:1 (v/v).

In certain embodiments, the ratio of carvedilol to ethanol is about 1:5 to about 1:30, preferably about 1:10 to about 1:20, and more preferably about 1:15 (g/ml).

In certain embodiments, the ratio of carvedilol to water is about 1:5 to about 1:30, preferably about 1:10 to about 1:20, and more preferably about 1:15 (g/ml).

The precipitated carvedilol phosphate may be recovered by any method known to the skilled artisan. Preferably, the carvedilol phosphate is recovered from the mixture by filtration, and then dried under reduced pressure (<1 atmosphere). Preferably, the drying can be at elevated temperature, e.g., in an oven at about 40° C. to about 60° C., preferably about 50° C.

Amorphous solids, in contrast to crystalline forms, do not possess a distinguishable crystal lattice and do not have an orderly arrangement of structural units. Amorphous forms are generally more soluble, and thus they are desirable for pharmaceutical purposes because the bioavailability of amorphous compounds may be greater than their crystalline counterparts.

Amorphous carvedilol phosphate may be analyzed to determine the amorphous nature of the product. The powder X-ray diffraction ("PXRD") pattern of amorphous carvedilol phosphate would show no peaks characteristic of crystalline forms of carvedilol phosphate, thus demonstrating the amorphous nature of the product. The presence of peaks characteristic of crystalline forms would indicate presence of crystalline carvedilol phosphate. A representative PXRD pattern for amorphous carvedilol phosphate is depicted in FIG. 1.

Preferably, the amorphous carvedilol phosphate comprises less than about 20% crystalline carvedilol and or carvedilol phosphate salts by weight, more preferably less than about 10% by weight, and even more preferably less than about 5% by weight, more preferably less than 1% by weight. The presence of a particular crystalline carvedilol can be determined by the presence of PXRD peaks characteristic of crystalline forms of carvedilol phosphate salts. The amount of crystallinity is quantified by methods known in the art like "crystallinity index" available to most XRD softwares.

In certain embodiments, the amorphous carvedilol phosphate comprises less than about 20% of Form I crystalline carvedilol by weight, more preferably less than about 10% by weight, and even more preferably less than about 5% by weight of Form I, as judged by the presence of PXRD peaks characteristic of Form I crystalline carvedilol. Form I is disclosed in European Patent Application EP 0893440.

Carvedilol Hydrogen Phosphate

The invention provides crystalline forms and an amorphous form of carvedilol hydrogen phosphate, which are more readily soluble than carvedilol free base. The amorphous carvedilol hydrogensulfate of the present invention has an XRD spectrum as substantially depicted in FIGS. 9 and 10.

Also provided is a process for preparing amorphous carvedilol hydrogen phosphate comprising dissolving carvedilol hydrogen phosphate in $C_1$-$C_8$ alcohols or in a mixture of C3-7 ketones with water, followed by solvent removal. Preferably the carvedilol hydrogen phosphate is dissolved in acetone and the ratio of acetone/water is about 2:1 (v/v).

Preferably the solvent is removed by fast evaporation, more preferably by spray drying. Spray drying can be carried out with an inlet temperature of about 80° C. to about 120° C. and an outlet temperature of below about 100° C. In one embodiment the spray drying is carried out with an inlet temperature of about 95° C. to about 105° C. and an outlet temperature of below about 40° C.

Figure 2:
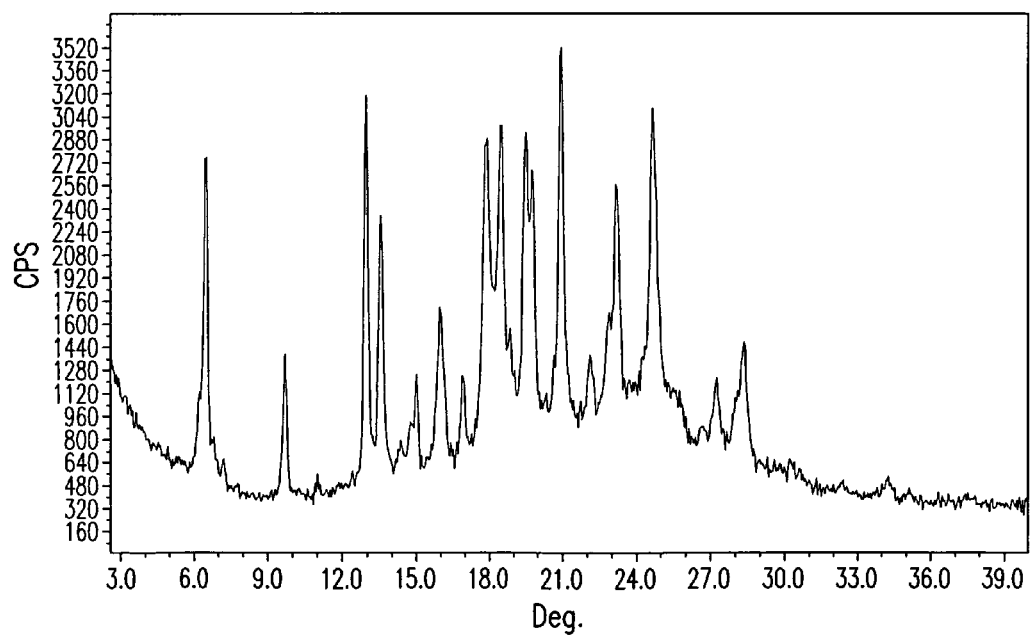
FIG. 2 is a powder X-ray diffractogram for carvedilol hydrogen phosphate Form G.
Figure 3:
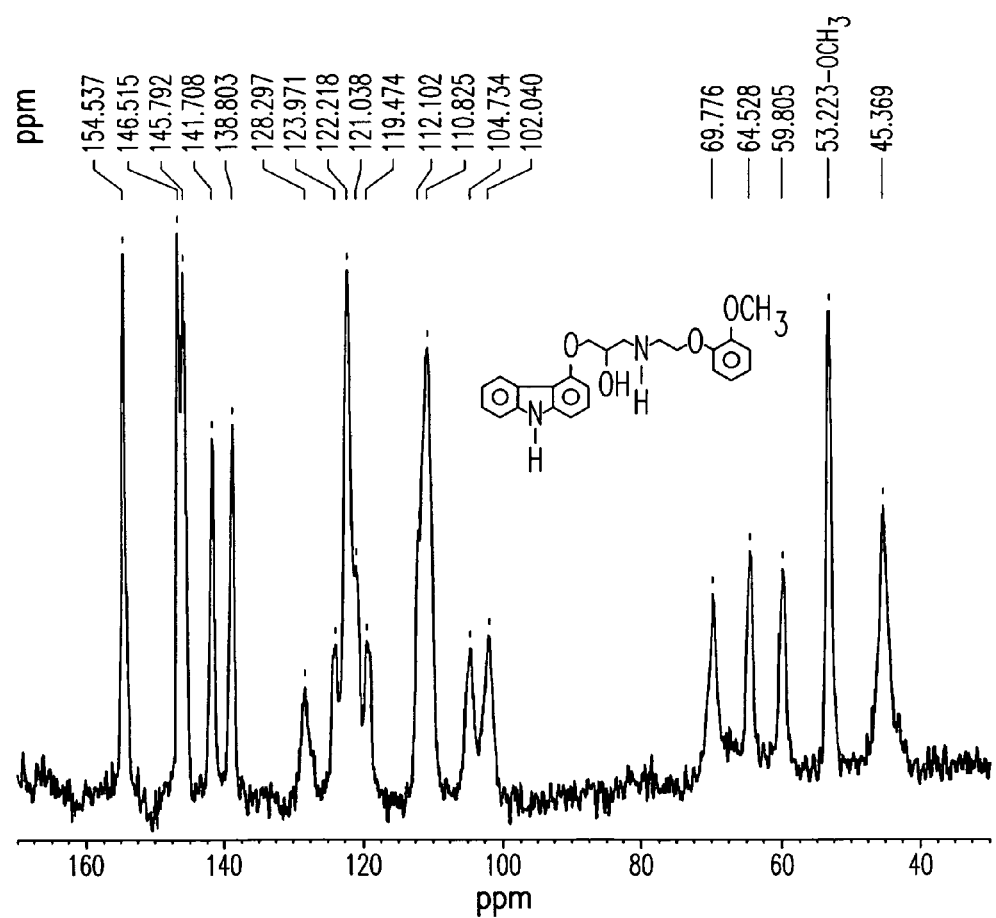
FIG. 3 illustrate a solid-state $^{13}$C-NMR spectrum of carvedilol hydrogen phosphate Form G.
Figure 3A:
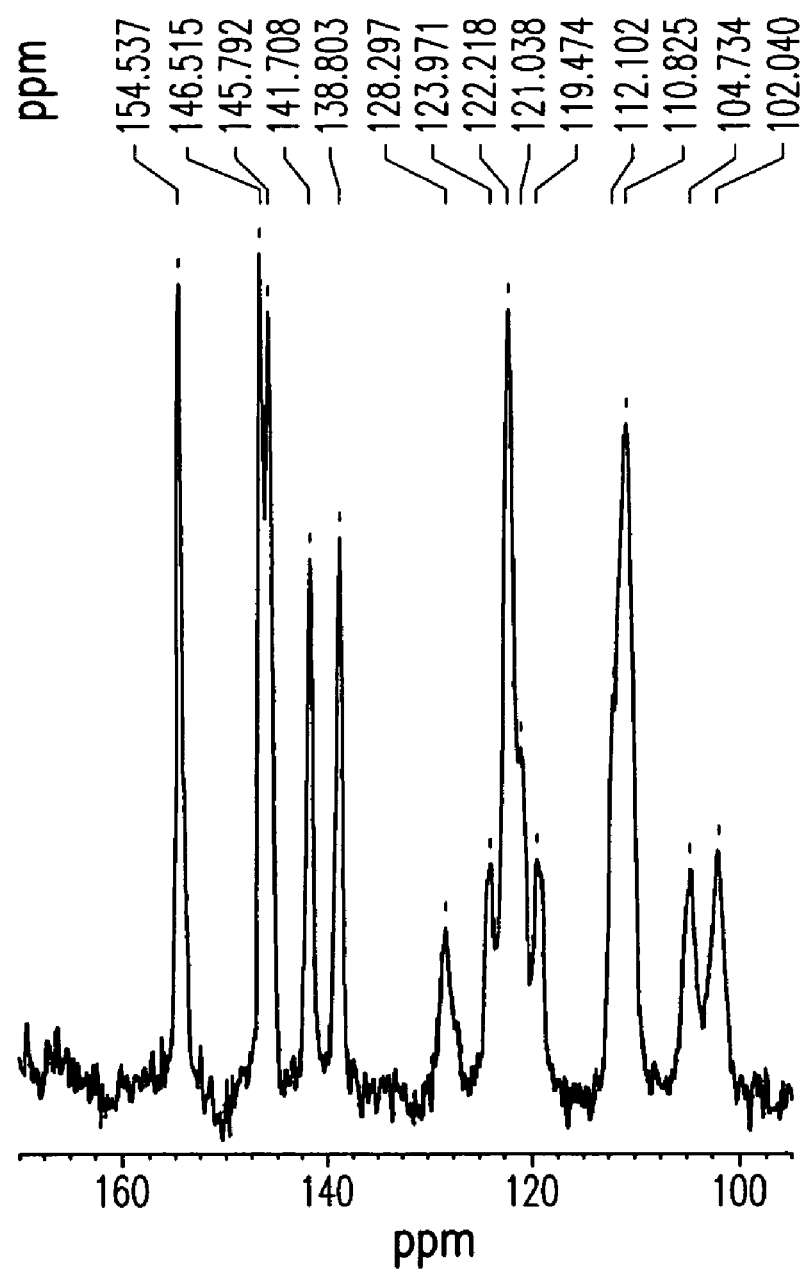
FIG. 3a illustrate a solid-state $^{13}$C-NMR spectrum of carvedilol dihydrogen phosphate Form G in the chemical shift area of 100 to 180 ppm.

In one embodiment, the invention encompasses a crystalline form of carvedilol hydrogen phosphate, referred to herein as Form G, characterized by data selected from the group consisting of: X-ray powder diffraction reflections at about: 6.5, 9.7, 13.0, 16.0 and 17.8 degrees two theta±0.2 degrees two theta; a solid-state $^{13}$C-NMR spectrum having chemical shift resonances at about 145.8, 141.7 and 110.8±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 43.8, 39.7 and 8.8±0.1 ppm. The lowest ppm resonance in the chemical shift area of 100 to 180 ppm is typically at about 102.0±1 ppm. The X-ray powder diffractogram of Form G is substantially shown in FIG. 2. The solid-state $^{13}$C NMR spectrum of Form G is substantially shown in FIGS. 3 and/or 3a.

Form G can also be characterized by any five peaks selected from the following list of PXRD peaks at about: 6.5, 9.7, 13.0, 13.5, 16.0, 17.8, 22.8 and 23.2±0.2 degrees two theta. In another embodiment Form G is characterized by data selected from: X-ray powder diffraction reflections at about: 6.5, 9.7, 16.0, 18.4 and 23.2 degrees two theta±0.2 degrees two theta.

Form G, and can be further characterized by data selected from the group consisting of: X-ray powder diffraction reflections at about 18.5, 19.5, 20.9, 23.1 and 24.7 degrees two-theta, ±0.2 degrees two-theta; a solid-state $^{13}$C-NMR spectrum having chemical shift resonances at about 154.5, 146.5 and 138.8±0.2 ppm; and a solid-state $^{13}$C NMR spectrum having chemical shift differences between the lowest ppm resonance in the chemical shift area of 100 to 180 ppm and another in the chemical shift area of 100 to 180 ppm of 52.5, 44.5 and 36.8±0.1 ppm. The lowest ppm resonance in the chemical shift area of 100 to 180 ppm is typically at about 102.0±1 ppm.

Form G has a weight loss, as measured by TGA, of between about 4.5-11.0% by weight.

In another embodiment, the invention encompasses a process for preparing carvedilol hydrogen phosphate Form G comprising: (a) combining carvedilol, phosphoric acid, and methanol to obtain a solution; (b) combining the solution with water to obtain a solid; and (c) recovering carvedilol hydrogen phosphate Form G.

The carvedilol and phosphoric acid in step (a) are preferably combined in a molar ratio of about 2:1. The solution of step (a) may be prepared by combining carvedilol and methanol to form a mixture and then slowly adding phosphoric acid to the mixture. Alternatively, the carvedilol and phosphoric acid may be added more or less simultaneously to the methanol.

The ratio of carvedilol to water can be about 1:8 (g/ml) to about 1:12 (g/ml). Preferably, the ratio of carvedilol to water is about 1:10 (g/ml).

The ingredients in step (a) may be heated to in order to achieve dissolution. Stirring may also be employed to promote dissolution. Preferably, the ingredients in step (a) are heated to reflux.

If the solution of step (a) is heated, the solution is preferably cooled to about 20° C. to about 35° C. before combining the solution with water in step (b).

The precipitated carvedilol hydrogen phosphate Form G may be recovered by any method known to the skilled artisan. Preferably, the carvedilol hydrogen phosphate Form G is recovered from the mixture by filtration, and then dried under reduced pressure (<1 atmosphere).

In another embodiment, the invention encompasses a process for preparing carvedilol hydrogen phosphate Form G comprising: (a) combining carvedilol, phosphoric acid, and acetone/water to obtain a mixture; (b) maintaining the mixture to obtain a solid; and (c) recovering carvedilol hydrogen phosphate Form G.

The carvedilol and phosphoric acid in step (a) are preferably combined in a molar ratio of about 2:1. In some embodiments, the molar ratio of phosphoric acid to carvedilol is about 0.8:1 to about 2.5:1. The mixture of step (a) may be prepared by first combining carvedilol and acetone/water and then slowly adding phosphoric acid to the mixture. Alternatively, the and phosphoric acid may be added more or less simultaneously to the acetone/water mixture.

Preferably, the acetone/water in step (a) is in a ratio of from about 4:1 to about 2:1 (v/v), and most preferably at about 3:1 (v/v).

Preferably, in step (b), the mixture is maintained, while stirring, at a temperature of about 20° C. to about 35° C., preferably at about room temperature (about 20° C. to about 23° C.) for about 12 hours.

The precipitated carvedilol hydrogen phosphate Form G may be recovered by any method known to the skilled artisan. Preferably, the carvedilol hydrogen phosphate Form G is recovered from the mixture by filtration, and then dried under reduced pressure (<1 atmosphere).

Form G can also be prepared by slurrying Form R, F1 or I in water. The slurry may be carried out for about 6 hours to about 3 days. The product is recovered and may be dried, such as at about 40° C. to about 60° C.

In another embodiment, the invention encompasses a process for preparing a phosphate salt of carvedilol, characterized by data selected from the group consisting of: X-ray powder diffraction reflections at about: 6.5, 9.7, 13.0, 16.0 and 17.8 degrees two theta±0.2 degrees two theta; a solid-state $^{13}$C-NMR spectrum having chemical shift resonances at about 145.8, 141.7 and 110.8±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 43.8, 39.7 and 8.8±0.1 ppm. The lowest ppm resonance in the chemical shift area of 100 to 180 ppm is typically at about 102.0±1 ppm. The X-ray powder diffractogram of Form G is substantially shown in FIG. 2. The solid-state $^{13}$C NMR spectrum of Form G is substantially shown in FIGS. 3 and/or 3a.

Form G can also be characterized by any five peaks selected from the following list of PXRD peaks at about: 6.5, 9.7, 13.0, 13.5, 16.0, 17.8, 22.8 and 23.2±0.2 degrees two theta. In one embodiment, Form G is characterized by data selected from: X-ray powder diffraction reflections at about: 6.5, 9.7, 13.5, 16.0 and 17.8 degrees two theta±0.2 degrees two theta. In another embodiment Form G is characterized by data selected from: X-ray powder diffraction reflections at about: 6.5, 9.7, 16.0, 18.4 and 23.2 degrees two theta±0.2 degrees two theta.

In another embodiment the present invention provides a method for preparing Form G comprising: (a) providing a suspension of amorphous carvedilol dihydrogen phosphate in phosphoric acid and water at a pH of about 3.5-7; (b) maintaining the mixture for at least 15 hours; and (c) recovering the phosphate salt of carvedilol.

Typically, in step (a) an aqueous solution of phosphoric acid is combined with the amorphous carvedilol dihydrogen phosphate.

Preferably, in step (b), the suspension is maintained, while stirring, at a temperature of about 20° C. to about 35° C., preferably at about 25° C., for about 19-21 hours.

The precipitated Form G may be recovered by any method known to the skilled artisan. Preferably, the carvedilol hydrogen phosphate Form G is recovered from the mixture by filtration, and then dried under reduced pressure (<1 atmosphere).

In another embodiment, the invention encompasses a process for preparing carvedilol hydrogen phosphate Form G comprising slurrying carvedilol dihydrogen phosphate Form R in water.

The ingredients are preferably maintained, while stirring, at a temperature of about 20° C. to about 35° C., preferably about room temperature (about 20° C. to about 23° C.), for about 12 hours to about 24 hours.

The obtained carvedilol hydrogen phosphate may be further recovered by any method known to the skilled artisan. Preferably, the carvedilol dihydrogen phosphate is recovered by filtration, and then dried under reduced pressure (<1 atmosphere).

In another embodiment, the invention encompasses a process for preparing carvedilol hydrogen phosphate Form G comprising slurrying carvedilol dihydrogen phosphate Form F1 in water.

The ingredients are preferably maintained, while stirring, at a temperature of about 20° C. to about 35° C., preferably about room temperature (about 20° C. to about 23° C.), for about 12 hours to about 24 hours.

The obtained carvedilol hydrogen phosphate may be further recovered by any method known to the skilled artisan. Preferably, the carvedilol dihydrogen phosphate is recovered by filtration, and then dried under reduced pressure (<1 atmosphere).

In one embodiment, the invention encompasses a crystalline form of carvedilol hydrogen phosphate, referred to herein as Form H, characterized by data selected from the group consisting of: X-ray powder diffraction reflections at about: 6.4, 6.6, 9.4, 14.5 and 15.4 degrees two theta±0.2 degrees two theta; X-ray powder diffraction reflections at about: 6.6, 9.7, 13.0, 13.8 and 15.6 degrees two theta±0.2 degrees two theta; any five peaks selected from the following list of PXRD peaks at about: 6.5, 6.8, 9.6, 13.0, 13.6, 15.6, 17.5 and 28.7±0.2 degrees two theta; X-ray powder diffraction reflections at about: 6.5, 9.6, 13.0, 13.6 and 18.7 degrees two theta±0.2 degrees two theta; X-ray powder diffraction reflections at about: 6.5, 9.6, 13.6, 18.7 and 20.2 degrees two theta±0.2 degrees two theta; a solid-state $^{13}$C-NMR spectrum having chemical shift resonances at about 146.3, 142.6 and 139.1±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 34, 30.3 and 26.8±0.1 ppm. The lowest ppm resonance in the chemical shift area of 100 to 180 ppm is typically at about 112.3±1 ppm.

Figure 4:
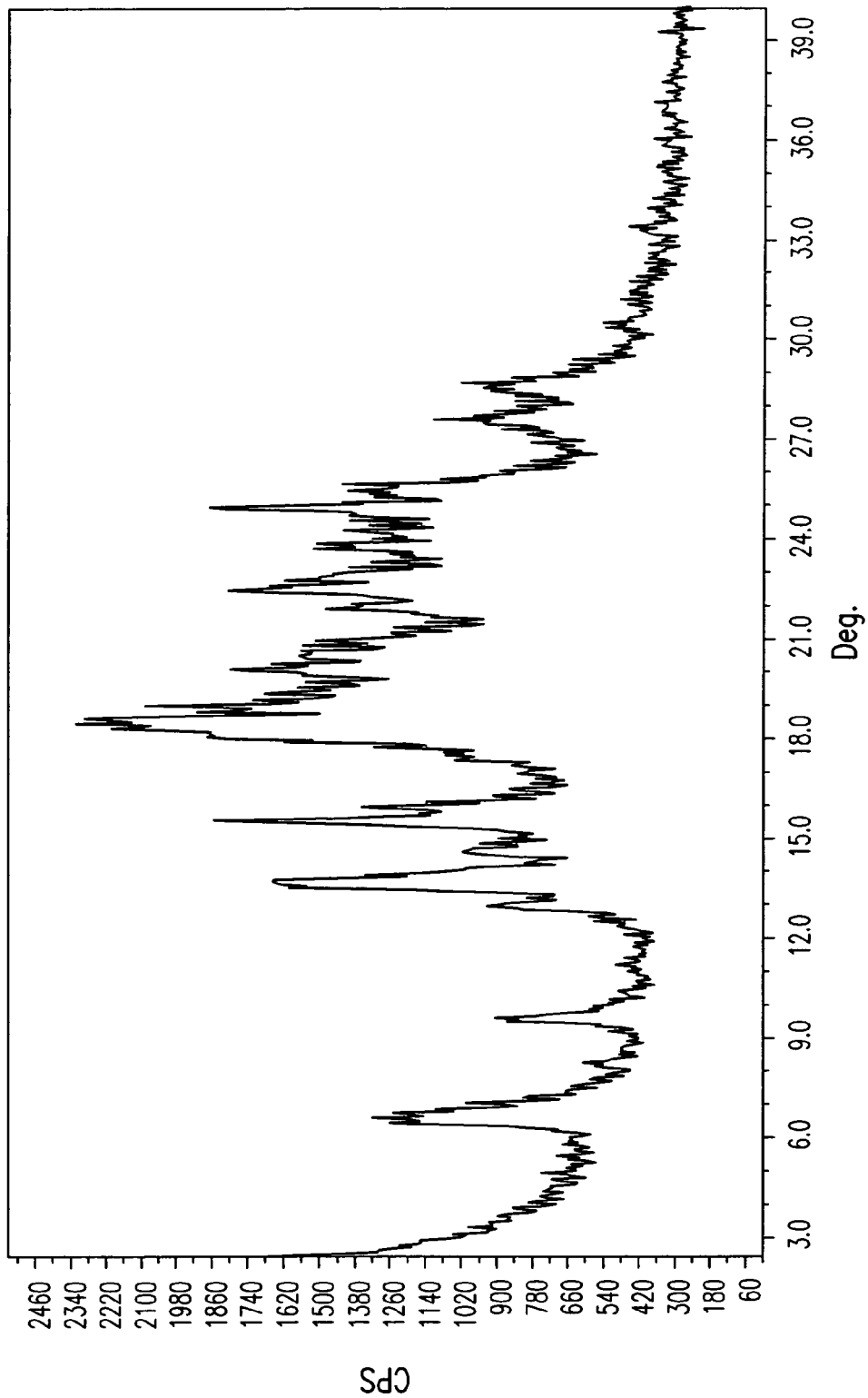
FIGS. 4 and 5 are powder X-ray diffractograms for carvedilol hydrogen phosphate Form H.
Figure 5:
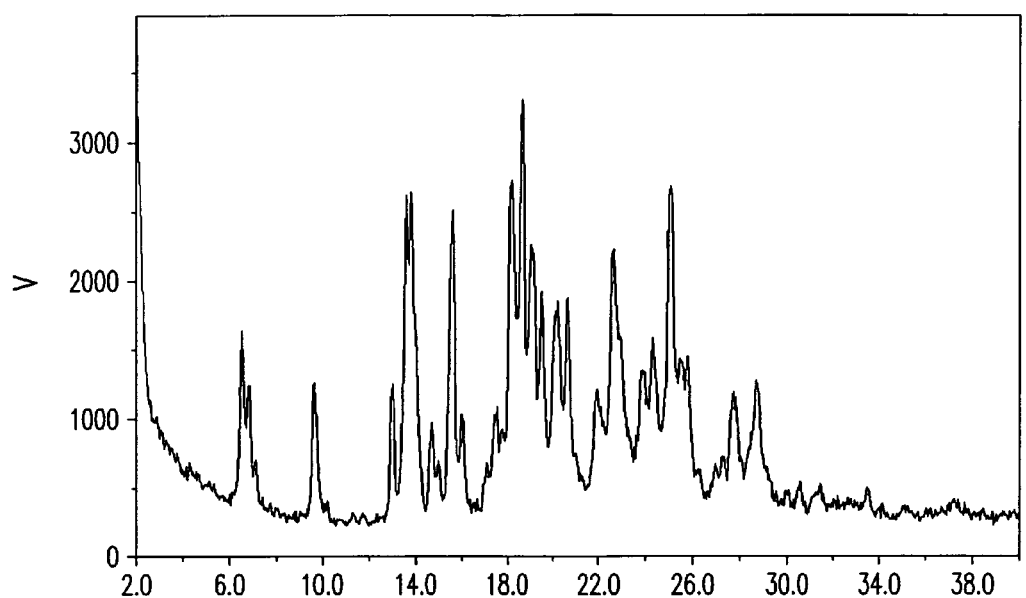
Figure 6:
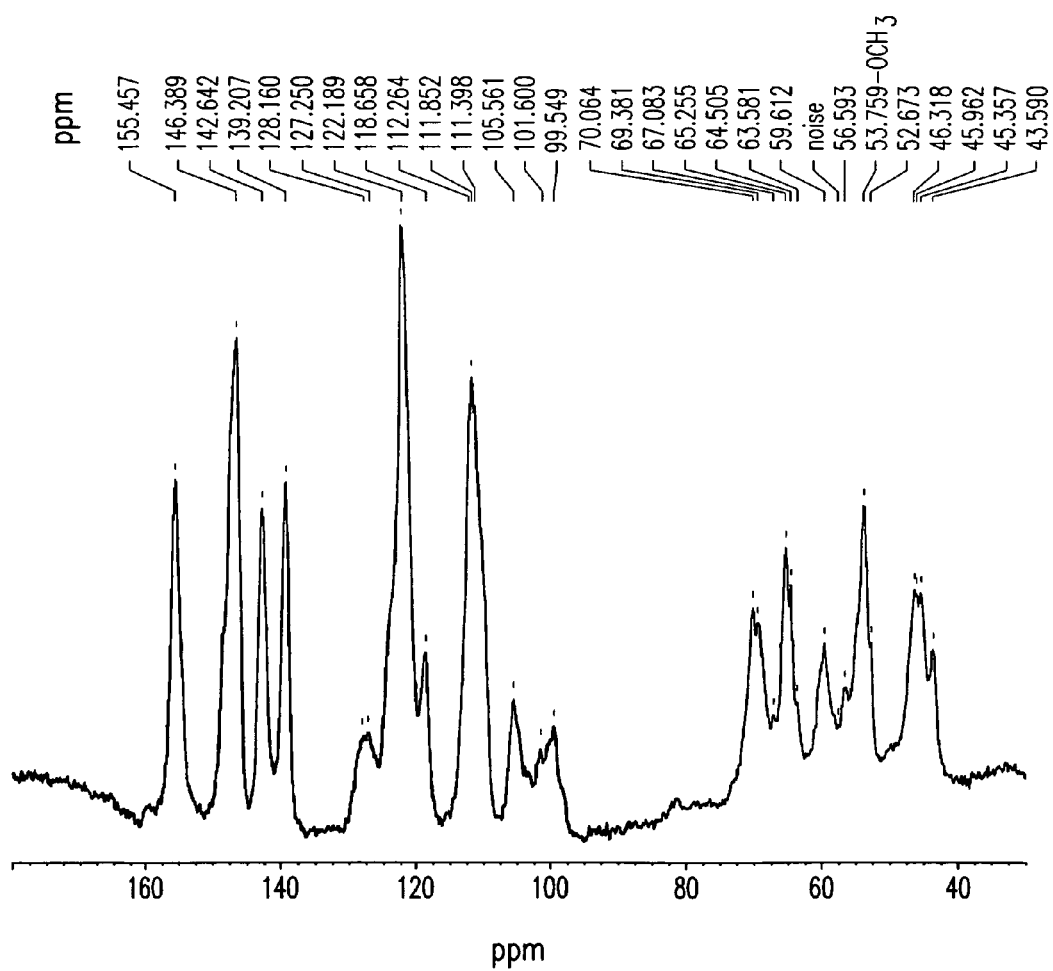
FIG. 6 illustrate a solid-state $^{13}$C-NMR spectrum of carvedilol hydrogen phosphate Form H.
Figure 6A:
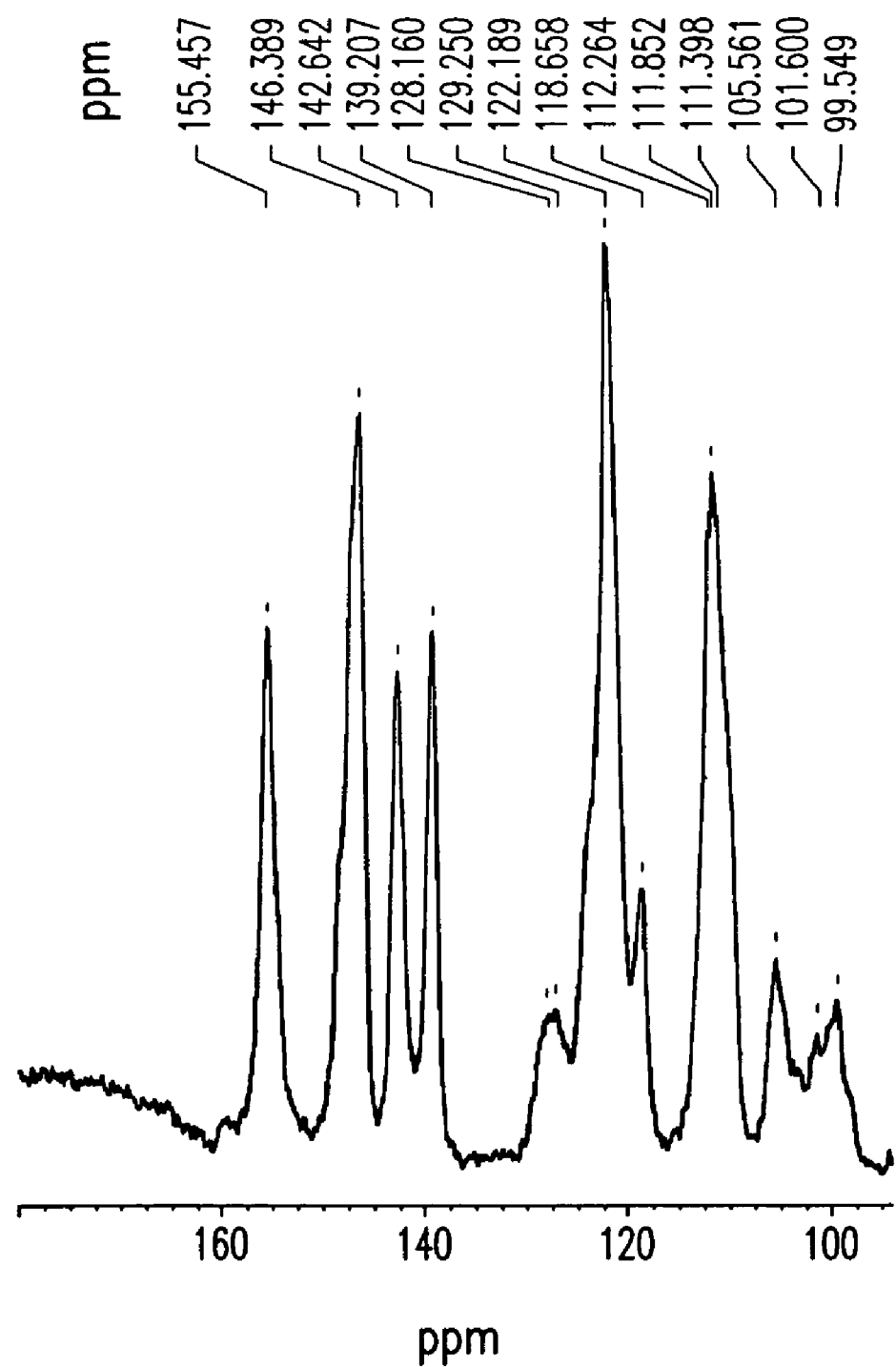
FIG. 6a illustrate a solid-state $^{13}$C-NMR spectrum of carvedilol dihydrogen phosphate Form H in the chemical shift area of 100 to 180 ppm.

The X-ray powder diffractogram of Form H is substantially shown in FIG. 4 or 5. The solid-state $^{13}$C NMR spectrum of Form H is substantially shown in FIGS. 6 and/or 6a.

Form H, and can be further characterized by data selected from the group consisting of: X-ray powder diffraction reflections at about 18.4, 19.3, 20.4, 22.4 and 25.3 degrees two-theta, ±0.2 degrees two-theta; X-ray powder diffraction reflections at about 18.6, 19.5, 20.6, 22.6 and 25.0 degrees two-theta, ±0.2 degrees two-theta; a solid-state $^{13}$C-NMR spectrum having chemical shift resonances at about 155.3, 122.2 and 112.3±0.2 ppm; and a solid-state $^{13}$C NMR spectrum having chemical shift differences between the lowest ppm resonance in the chemical shift area of 100 to 180 ppm and another in the chemical shift area of 100 to 180 ppm of 43, 9.9 and 0±0.1 ppm. The lowest ppm resonance in the chemical shift area of 100 to 180 ppm is typically at about 112.3±1 ppm.

Form H has a weight loss, as measured by TGA, of between about 2.9-7.1% by weight.

In another embodiment, the invention encompasses a process for preparing carvedilol hydrogen phosphate Form H comprising: (a) combining carvedilol, phosphoric acid, and ethanol/water to obtain a mixture; (b) maintaining the mixture for at least 6 hours to obtain a solid; and (c) recovering carvedilol hydrogen phosphate Form H.

The carvedilol and phosphoric acid in step (a) are preferably combined in a molar ratio of about 2.5:1 to about 0.8:1, more preferably about 2:1. The mixture of step (a) may be prepared by first combining carvedilol and ethanol, then slowly adding phosphoric acid to the mixture, heating to reflux and finally adding water.

Preferably, the ethanol/water in step (a) is in a ratio of from about 1:1 to about 7:1, most preferably about 5:1.

If the solution of step (a) is heated, the solution is cooled to about 20° C. to about 35° C., preferably to about room temperature (about 20° C. to about 23° C.), prior to step (b).

Preferably, in step (b), the mixture is maintained, while stirring, at a temperature of about 20° C. to about 35° C., preferably about room temperature (about 20° C. to about 23° C.), for about 12 hours.

The precipitated carvedilol hydrogen phosphate Form H may be recovered by any method known to the skilled artisan. Preferably, the carvedilol hydrogen phosphate Form H is recovered from the mixture by filtration, and then dried under reduced pressure (<1 atmosphere).

Figure 7:
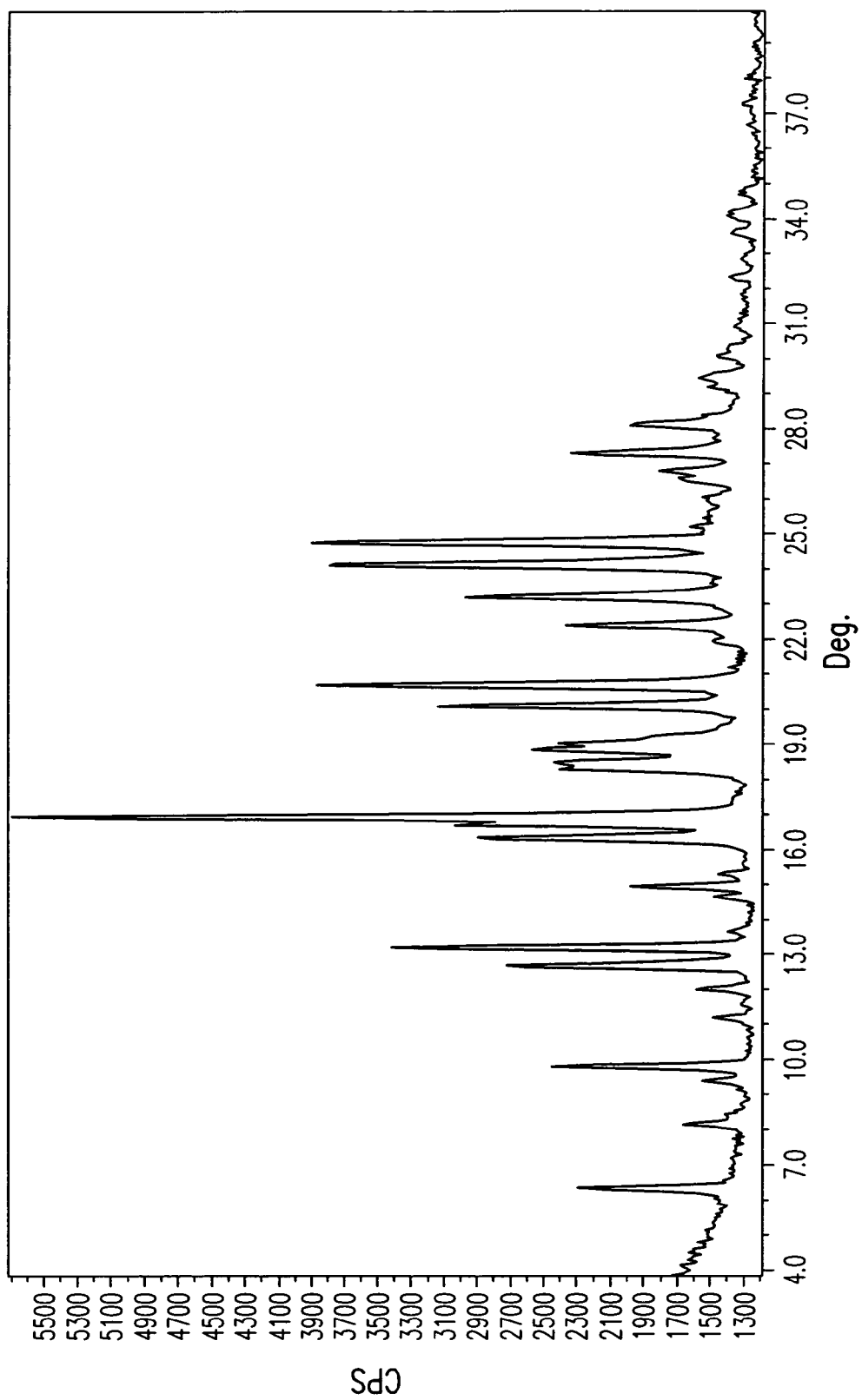
FIG. 7 is a powder X-ray diffractogram for carvedilol hydrogen phosphate Form K.

In another embodiment, the invention encompasses a crystalline form of carvedilol hydrogen phosphate, referred to herein as Form K, characterized by X-ray powder diffraction reflections at about: 6.3, 9.8, 12.7, 13.2 and 16.9 degrees two theta±0.2 degrees two theta;

Form K has an X-ray powder diffractogram as substantially shown in FIG. 7.

Form K can also be characterized by any five peaks selected from the following list of PXRD peaks at about: 6.3, 9.8, 12.7, 13.2, 16.3, 16.9, 18.3 and 19.0±0.2 degrees two theta.

Form K can also be characterized by data selected from: X-ray powder diffraction reflections at about: 6.3, 9.8, 16.9, 18.3 and 23.2 degrees two theta±0.2 degrees two theta.

Form K can also be characterized by data selected from: X-ray powder diffraction reflections at about: 6.3, 9.8, 14.9, 20.1 and 28.2 degrees two theta±0.2 degrees two theta.

Form K can be further characterized by X-ray powder diffraction reflections at about 16.3, 20.1, 20.7, 24.1 and 24.8 degrees two-theta, ±0.2 degrees two-theta Form K has a weight loss, as measured by TGA, of between about 9.1-13.0% by weight.

In another embodiment, the invention encompasses a process for preparing carvedilol hydrogen phosphate Form K comprising exposing carvedilol hydrogen phosphate Form H to more than about 80% relative humidity for at least about 7 days.

Fork K can also be prepared by combining carvedilol in acetone/water, preferably (3:1) solution higher than 50 ml and adding phosphoric acid, preferably about 85% concentration. The resulting reaction mixture can then be stirred and maintained to obtain a precipitate. The product can be recovered and dried, under a pressure of less than one atmosphere.

In another embodiment, the invention encompasses a process for preparing an amorphous form of carvedilol hydrogen phosphate. This process comprises dissolving carvedilol hydrogen phosphate in $C_1$-$C_8$ alcohols or in a mixture of $C_{3-7}$ ketones with water, followed by solvent removal.

Preferably, the solvent in which carvedilol hydrogen phosphate is dissolved is methanol or acetone.

Whenever acetone is used, the ratio of acetone/water is preferably from about 3:1 to about 1:1 (v/v), and more preferably about 2:1 (v/v).

Preferably, removing the solvent is performed using spray drying.

The processes of the present invention may preferably employ spray drying with an inlet temperature of about 80° C. to about 120° C., and an outlet temperature of less than about 100° C.

The processes of the present invention may preferably employ spray drying with an inlet temperature of about 95° C. to about 105° C., preferably about 100° C.

The spray drying may preferably be conducted with an outlet temperature of below the inlet temperature, preferably below about 35° C. to about 45° C., and more preferably below about 40° C.

The drying gas used in the process of the present invention may be any suitable gas, although inert gases such as nitrogen, nitrogen-enriched air, and argon are preferred.

The carvedilol dihydrogen phosphate product produced by spray drying may be recovered by techniques commonly used in the art, such as using a cyclone or a filter.

The carvedilol hydrogen phosphate starting material used for the processes of the present invention may be any crystalline form of carvedilol hydrogen phosphate, including any solvates and hydrates. With processes where carvedilol hydrogen phosphate goes into solution, the form of the starting material is of minimal relevance since any solid state structure is lost in solution.

In another embodiment, the invention encompasses a phosphate salt of carvedilol, referred to herein as Form Q, characterized by X-ray powder diffraction reflections at about: 6.2, 7.3, 14.5, 17.5 and 21.3 degrees two theta±0.2 degrees two theta.

Figure 8:
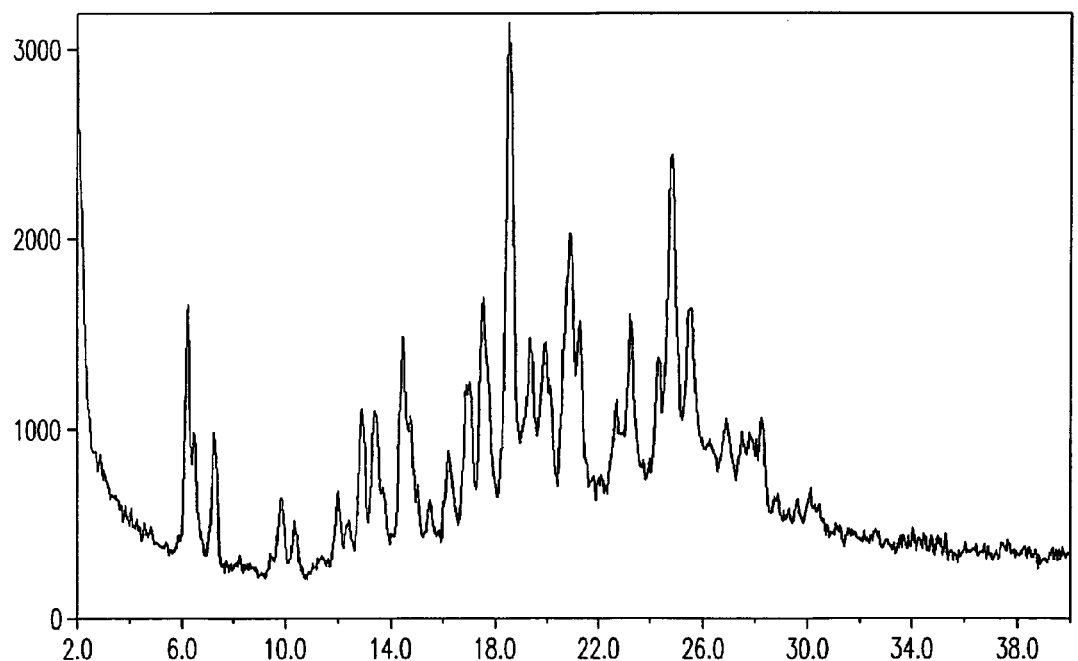
FIG. 8 is a powder X-ray diffractogram for carvedilol hydrogen phosphate Form Q.

In another embodiment, Form Q having X-ray powder diffractogram as substantially shown in FIG. 8.

Form Q has a weight loss, as measured by TGA, of about 3.8% by weight.

Form Q Carvedilol hydrogen phosphate can be prepared by exposing Form K to a relative humidity of less than about 20%, preferably about 0% relative humidity (RH). Exposure is preferably from about 1 day to about 10 days, more preferably about 7 days. The process can be carried out at room temperature (about 20-23° C.).

Each of Forms G, H, K and Q contain less than comprises less than about 20% crystalline carvedilol phosphate salts by weight, more preferably less than about 10% by weight, and even more preferably less than about 5% by weight add: less than 1%. The presence of a particular crystalline carvedilol can be determined by the presence of PXRD peaks characteristic of crystalline carvedilol phosphate salts.

In certain embodiments, Each of Forms G, H, K and Q contain less than 50%, less than 25%, less than 10%, less than 5%, or less than 1% by weight of carvedilol dihydrogen phosphate Form I. In certain embodiments, Each of Form G, H, K and Q is provided as a solid material in which Each of Form G, H, K and Q represents 50%, 75%, 90%, 95%, or 99% by weight of the solid material.

Figure 9:
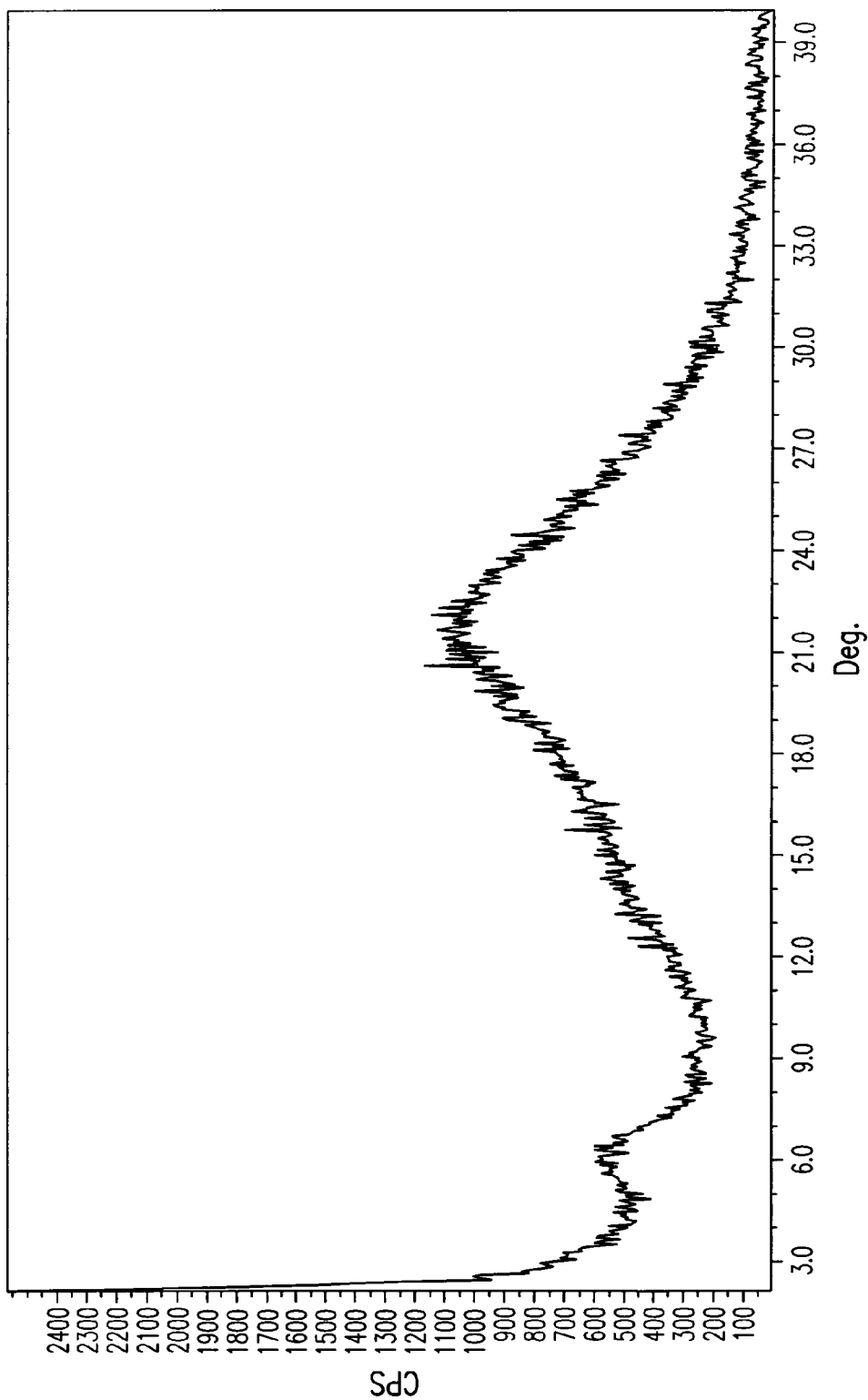
FIG. 9 is a powder X-ray diffractogram for the amorphous form of carvedilol hydrogen phosphate (according to Example 12).
Figure 10:
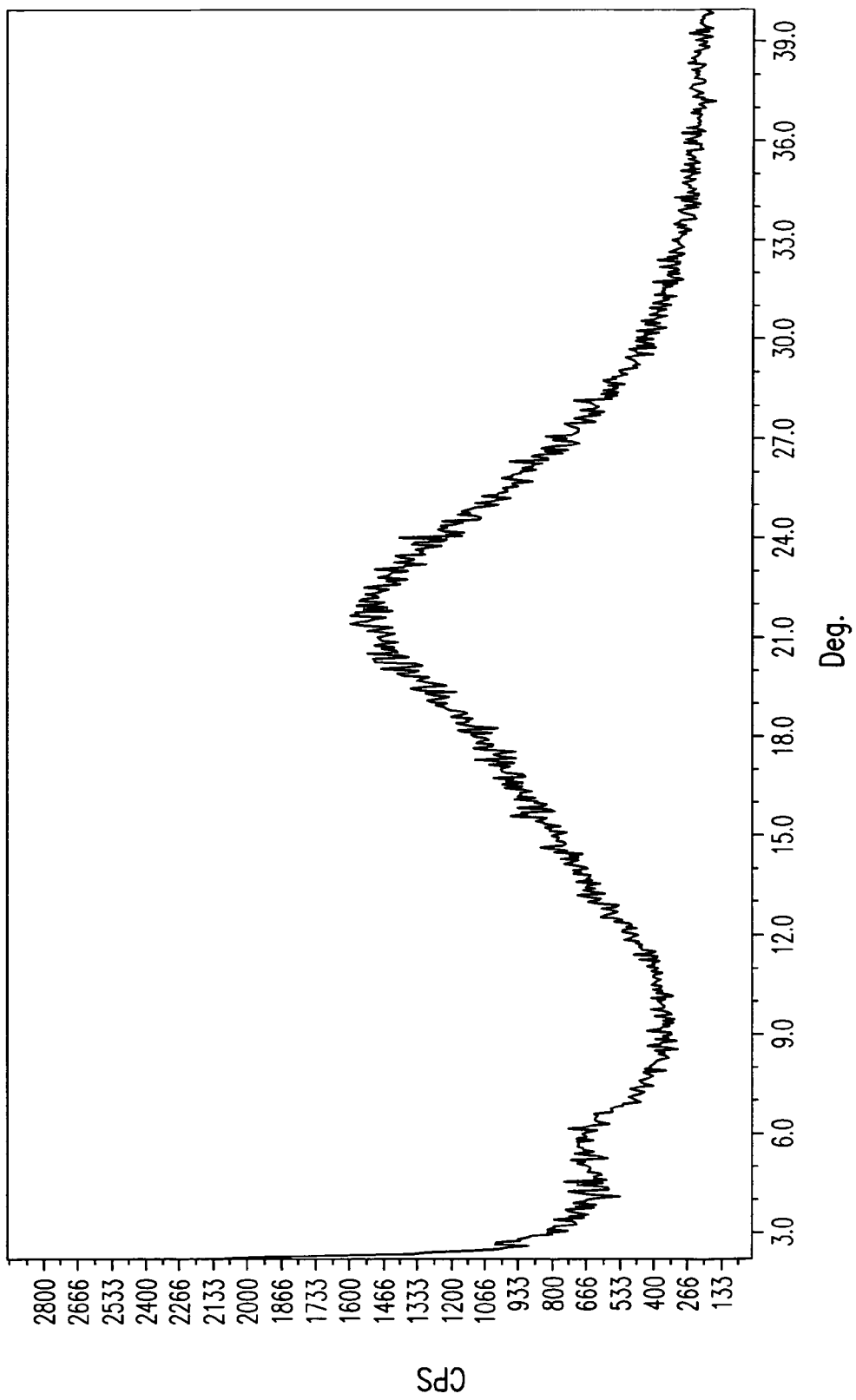
FIG. 10 is a powder X-ray diffractogram for the amorphous form of carvedilol hydrogen phosphate (according to Example 13).

In another embodiment, the invention encompasses an amorphous form of carvedilol hydrogen phosphate. A typical powder x-ray diffraction diagram for the amorphous form is shown in FIGS. 9 and 10.

Amorphous carvedilol hydrogen phosphate may be analyzed to determine the amorphous nature of the product. The powder X-ray diffraction ("PXRD") pattern of amorphous carvedilol hydrogen phosphate would show no peaks characteristic of crystalline forms of carvedilol hydrogen phosphate, thus demonstrating the amorphous nature of the product. The presence of peaks characteristic of crystalline forms would indicate presence of crystalline carvedilol hydrogen phosphate.

Preferably, the amorphous carvedilol hydrogen phosphate comprises less than about 20% crystalline carvedilol and or carvedilol phosphate salts by weight, more preferably less than about 10% by weight, and even more preferably less than about 5% by weight, and even more preferably less than about 1% by weight. The presence of crystalline carvedilol hydrogen phosphate can be determined by the presence of PXRD peaks characteristic of crystalline carvedilol phosphate salts.

In certain embodiments, the amorphous carvedilol hydrogen phosphate comprises less than about 20% of Form I crystalline carvedilol by weight, more preferably less than about 10% by weight, and even more preferably less than about 5% by weight of Form I, as judged by the presence of PXRD peaks characteristic of Form I crystalline carvedilol. Form I is disclosed in European Patent Application EP 0893440.

Carvedilol Dihydrogen Phosphate

The invention provides crystalline forms of carvedilol dihydrogen phosphate as well as processes for obtaining crystalline forms of carvedilol dihydrogen phosphate, which are more readily soluble than carvedilol free base.

Figure 11:
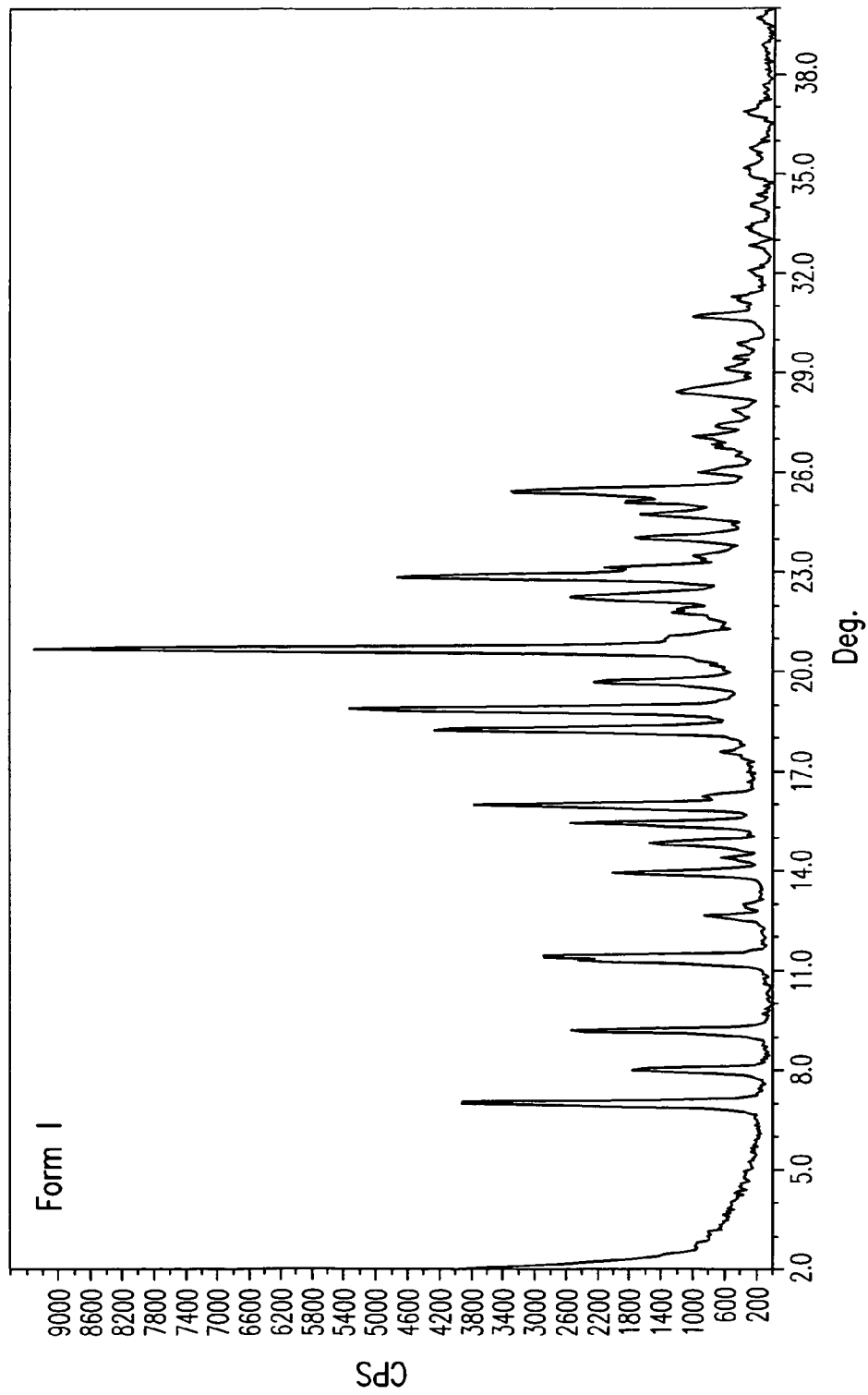
FIG. 11 illustrates a characteristic powder X-ray diffractogram for carvedilol dihydrogen phosphate Form I.
Figure 12:
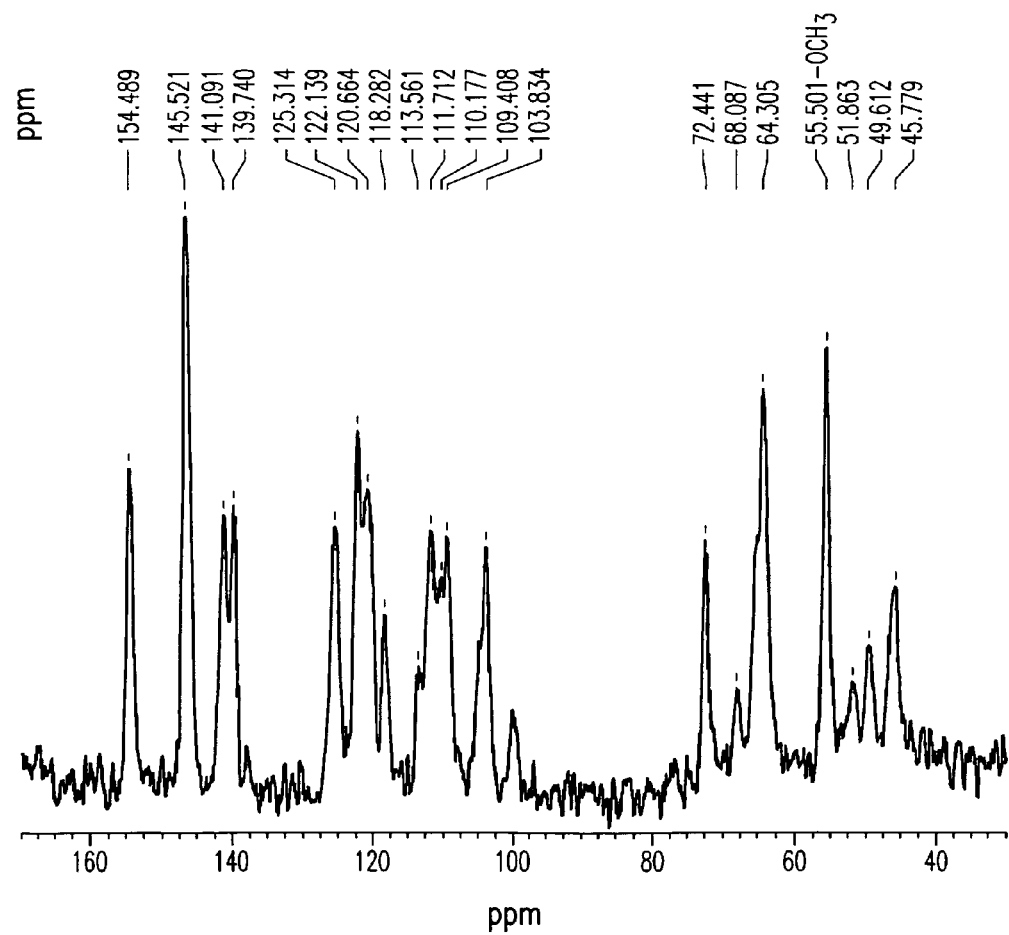
FIG. 12 illustrates a solid-state $^{13}$C-NMR spectrum of carvedilol dihydrogen phosphate Form I.

In one embodiment the present invention provides processes for preparing carvedilol dihydrogen phosphate Form I. Form I is characterized by data selected from the group consisting of: X-ray powder diffraction reflections at about: 7.0, 8.0, 9.2, 11.4 and 16.0 degrees two theta±0.2 degrees two theta; a solid-state $^{13}$C-NMR spectrum having chemical shift resonances at about 154.5, 146.5, 139.7 and 122.1±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 50.7, 42.7 and 18.3±0.1 ppm. X-ray diffractogram substantially shown in FIG. 11; solid-state $^{13}$C-NMR substantially shown in FIG. 12.

I can be prepared by exposing Form F to about 100% humidity at elevated temperature, preferably about 30° C. to about 80° C., more preferably about 60° C. Preferably the exposure is carried out for about 1 to about 10 days, more preferably for about 7 days.

In one embodiment, the invention encompasses a process for preparing crystalline carvedilol dihydrogen phosphate Form I, comprising: combining carvedilol, phosphoric acid and a solvent selected from the group consisting of $C_4$-$C_8$ alcohols, $C_5$-$C_{10}$ aliphatic hydrocarbons, $C_{6-12}$ aromatic hydrocarbons, $C_3$-$C_7$ ketones $C_4$-$C_8$ ethers, $C_3$-$C_7$ esters and acetonitrile and precipitating carvedilol dihydrogen phosphate Form I from the reaction mixture.

Preferably, the solvent is selected from the group consisting of: butanol, 2-butanol, n-butanol, tert-butanol, heptane, acetone, methyl isobutyl ketone (MIBK), methyl ethyl ketone (MEK), propylene glycol monomethyl ether (PGME), THF, methyl tert-butyl ether (MTBE), methyl acetate, isobutyl acetate, ethyl acetate and acetonitrile. More preferably, the solvent is selected from the group consisting of: methanol, ethanol, isopropyl alcohol (IPA), and THF. Acetone is not used in a mixture with another solvent.

$C_1$-$C_4$ alcohols can be used, but the process with methanol and ethanol is carried out at about room temperature (about 20-23° C.). Recovery from methanol and ethanol is carried out rapidly, preferably less than about 4 hours. The process with isopropyl alcohol is carried out at a temperature higher than about 55° C.

The carvedilol and phosphoric acid are preferably present in a molar ratio of about 1:1. Precipitation may be obtained from a solution or a slurry of carvedilol, phosphoric acid and the solvent.

The ingredients may be heated in order to achieve dissolution. Stirring may also be employed to promote dissolution. Preferably, the ingredients are heated to reflux. Whether the ingredients are heated, the process may further comprise cooling, to induce crystallization.

Whenever precipitation occurs from a slurry of carvedilol, phosphoric acid and the solvent, the ingredients are preferably maintained, while stirring, at a temperature of about 20° C. to about 35° C. for about 12 hours to about 24 hours. When precipitation occurs from a slurry in ethanol, stirring is employed for about 1 hour.

Precipitation may occur with or without the presence of water, except when acetone is used water is absent and when methanol is used water is present. The precipitated carvedilol dihydrogen phosphate Form I may be recovered by any method known to the skilled artisan. Preferably, the carvedilol dihydrogen phosphate Form I is recovered by filtration, and then dried under reduced pressure (<1 atmosphere).

In another embodiment, the invention encompasses a process for preparing crystalline carvedilol dihydrogen phosphate Form I, is characterized by data selected from the group consisting of: X-ray powder diffraction reflections at about: 7.0, 8.0, 9.2, 11.4 and 16.0 degrees two theta±0.2 degrees two theta; a solid-state $^{13}$C-NMR spectrum having chemical shift resonances at about 154.5, 146.5, 139.7 and 122.1±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 50.7, 42.7 and 18.3±0.1 ppm. X-ray diffractogram substantially shown in FIG. 11; solid-state $^{13}$C-NMR substantially shown in FIG. 12 comprising slurrying carvedilol dihydrogen phosphate Form R in ethanol.

The carvedilol dihydrogen phosphate Form R starting material may be obtained as described below.

The ingredients are preferably maintained, while stirring, at a temperature of about 20° C. to about 35° C. for about 12 hours to about 24 hours.

Preferably, absolute ethanol is used. "Absolute" or "technical grade" or "anhydrous" are common terms used in the art to refer to alcohols having less than about 2% water by volume.

The obtained carvedilol dihydrogen phosphate Form I may be further recovered by any method known to the skilled artisan. Preferably, the carvedilol dihydrogen phosphate Form I is recovered by filtration, and then dried under reduced pressure (<1 atmosphere).

From I can be prepared by heating Form, N, P carvedilol dihydrogen phosphate, preferably to about 60° C. to about 140° C., more preferably about 80° C.-120° C. Preferably the heating is carried out for about 10 minutes to about 3 hours, more preferably about 30 minutes.

From I can be prepared by heating Form L1, R and amorphous carvedilol dihydrogen phosphate, preferably to about 110° C. to about 150° C., more preferably about 120° C.-140° C. Preferably the heating is carried out for about 10 minutes to about 3 hours, more preferably about 30 minutes.

Form I can also be prepared by slurrying Form F1, amorphous carvedilol dihydrogen phosphate, Form R, or Form N in acetone. The slurry can be maintained until obtaining the transformation. The slurry may be maintained for about 12 hours to about 5 days, preferably for about 1 day. The crystals can then be recovered by conventional techniques, and can also be dried such as at a temperature of about 50° C. to about 90° C., and a pressure of below one atmosphere.

Form I can also be prepared by putting Form P or Form N under pressure, such as pressure of about 1 ton to about 3 ton, preferably about 2 ton.

Form I can also be prepared by grinding Forms F and P, such as for about 1 to about 3 minutes.

Form I can also be prepared by placing amorphous carvedilol dihydrogen phosphate in an atmosphere of n-propanol, iso-propanol, butanol, acetone and ethyl acetate.

Form I can be prepared by slurrying Form N in water. The slurry can be carried out for about 12 hours to about 5 days, preferably about 12 hours. The product can then be recovered by conventional techniques, such as filtration, and then dried, such as at about 40° C. to about 60° C., under pressure below one atmosphere.

In another embodiment, the invention encompasses a crystalline form of carvedilol dihydrogen phosphate, referred to herein as Form F, characterized by data selected from: X-ray powder diffraction reflections at about: 7.7, 8.7, 16.8 and 22.8 degrees two theta±0.2 degrees two theta; X-ray powder diffraction reflections at about: 7.6, 8.6, 16.7 and 22.8 degrees two theta±0.2 degrees two theta; X-ray powder diffraction reflections at about: 7.7, 8.7, 16.8, 22.8 and 26.5 degrees two theta±0.2 degrees two theta; and X-ray powder diffraction reflections at about: 7.6, 8.6, 16.7, 22.8 and 26.5 degrees two theta±0.2 degrees two theta; a solid-state $^{13}$C-NMR spectrum having chemical shift resonances at about 149.8, 145.4 and 140.7±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 50.6, 46.2 and 41.5±0.1 ppm. The lowest ppm resonance in the chemical shift area of 100 to 180 ppm is typically at about 99.2±1 ppm; a solid-state $^{13}$C-NMR spectrum having chemical shift resonances at about 149.8, 145.4, 138.5 and 140.7±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 50.6, 46.2, 39.3 and 41.5±0.1 ppm. The lowest ppm resonance in the chemical shift area of 100 to 180 ppm is typically at about 99.2±1 ppm.

Figure 23:
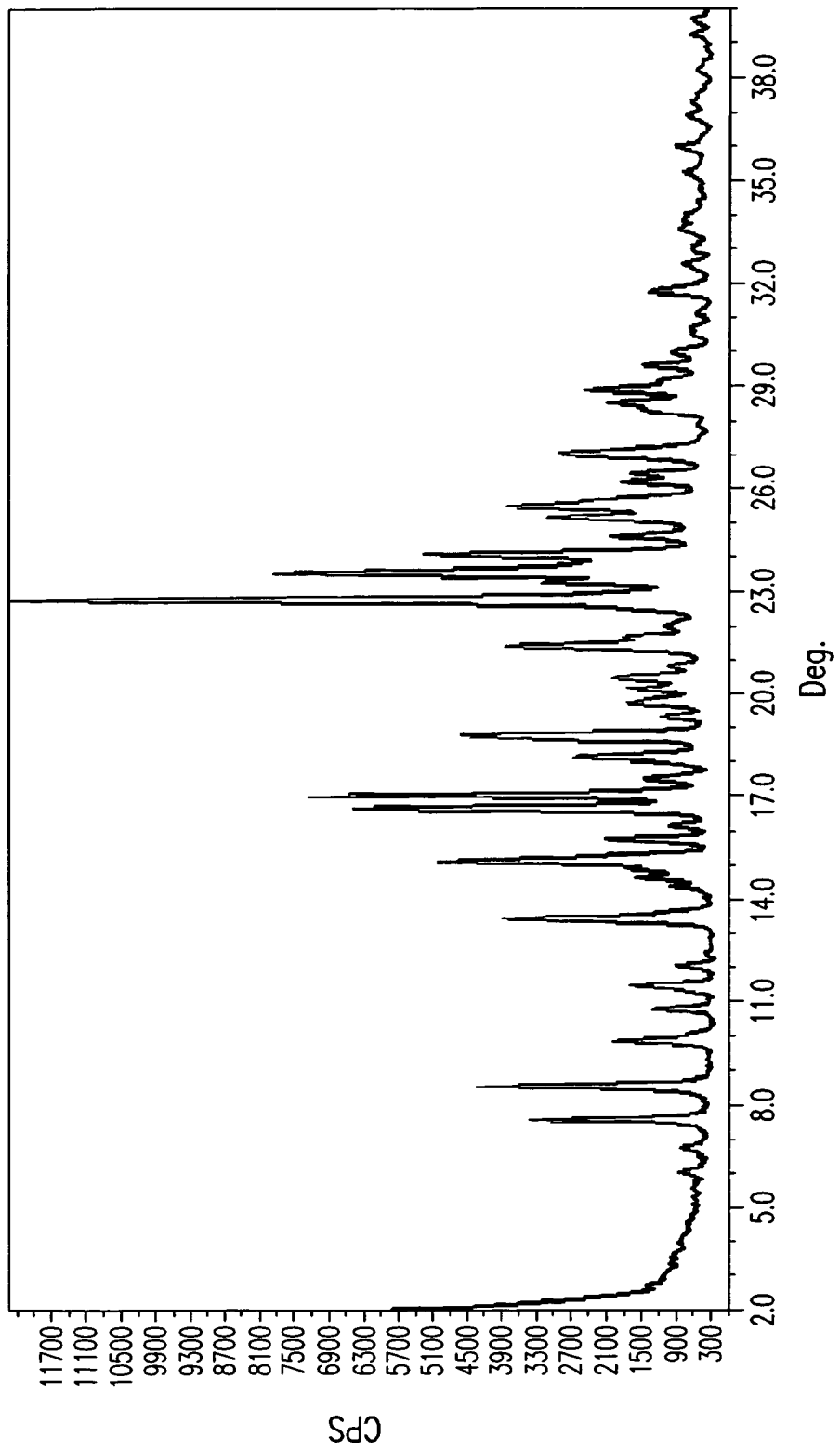
FIG. 23 illustrates a characteristic powder X-ray diffractogram for carvedilol dihydrogen phosphate Form F obtained in Example 49.
Figure 24:
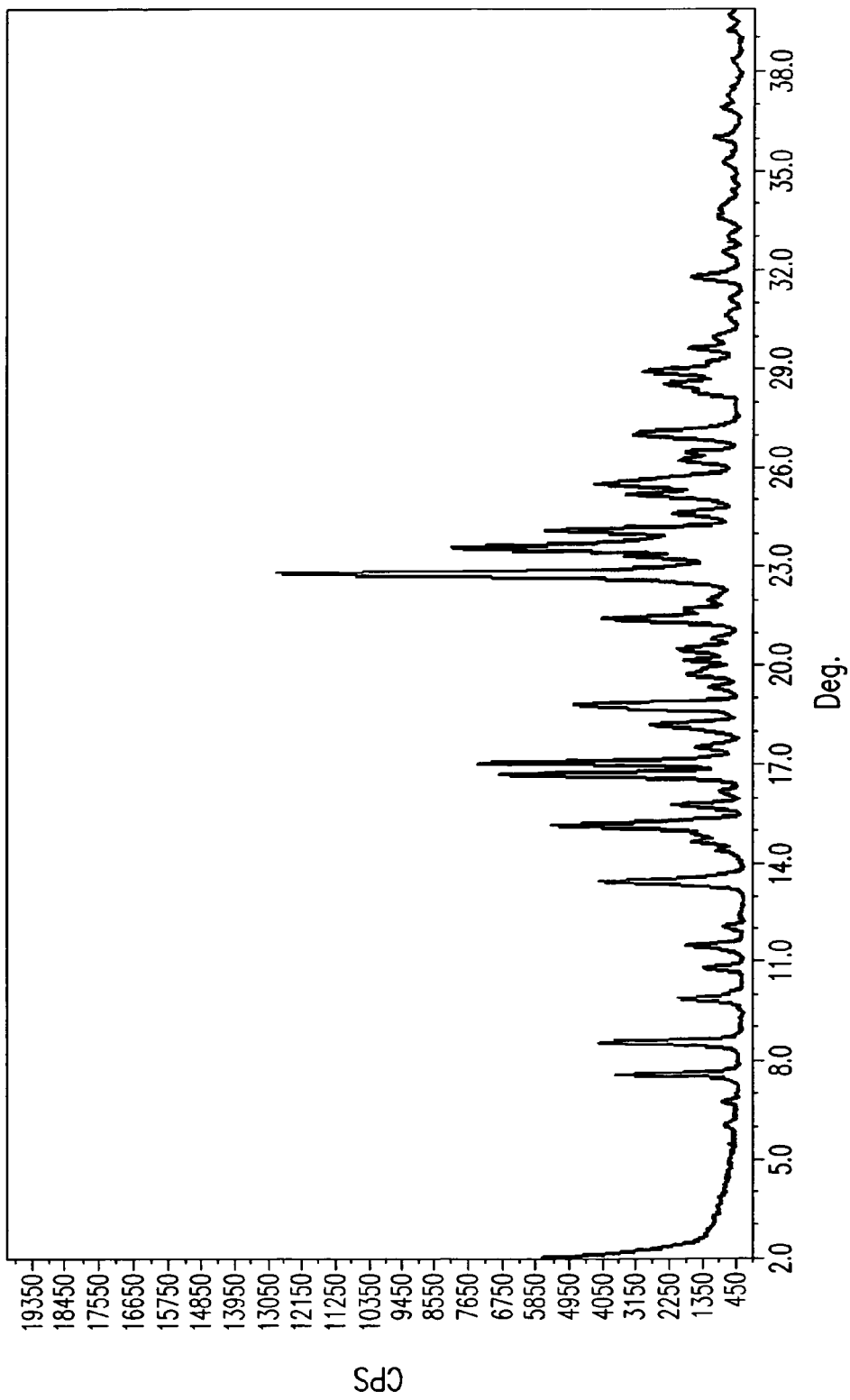
FIG. 24 illustrates a characteristic powder X-ray diffractogram for carvedilol dihydrogen phosphate Form F obtained in Example 50.

Form F has an X-ray powder diffractogram as substantially shown in FIG. 23 or 24. Form F has a solid-state $^{13}$C NMR spectrum as substantially shown in FIG. 25 and or 25a.

In another embodiment, the invention encompasses a crystalline form of carvedilol dihydrogen phosphate, referred to herein as Form F, characterized by data selected from: X-ray powder diffraction reflections at about: 7.7, 8.7, 13.5, 15.2 and 22.9 degrees two theta±0.2 degrees two theta; X-ray powder diffraction reflections at about: 7.6, 8.6, 13.4, 15.1 and 22.8 degrees two theta±0.2 degrees two theta.

In another embodiment, the invention encompasses a crystalline form of carvedilol dihydrogen phosphate, referred to herein as Form F, characterized by data selected from: X-ray powder diffraction reflections at about: 7.7, 13.5, 15.2, 18.3 and 18.9 degrees two theta±0.2 degrees two theta; X-ray powder diffraction reflections at about: 7.6, 13.4, 15.1, 18.2 and 18.8 degrees two theta±0.2 degrees two theta.

In another embodiment, the invention encompasses a crystalline form of carvedilol dihydrogen phosphate, referred to herein as Form F, characterized by data selected from: X-ray powder diffraction reflections at about: 7.7, 13.5, 15.2, 17.2 and 21.5 degrees two theta±0.2 degrees two theta; X-ray powder diffraction reflections at about: 7.6, 13.4, 15.1, 17.1 and 21.4 degrees two theta±0.2 degrees two theta.

Figure 25:
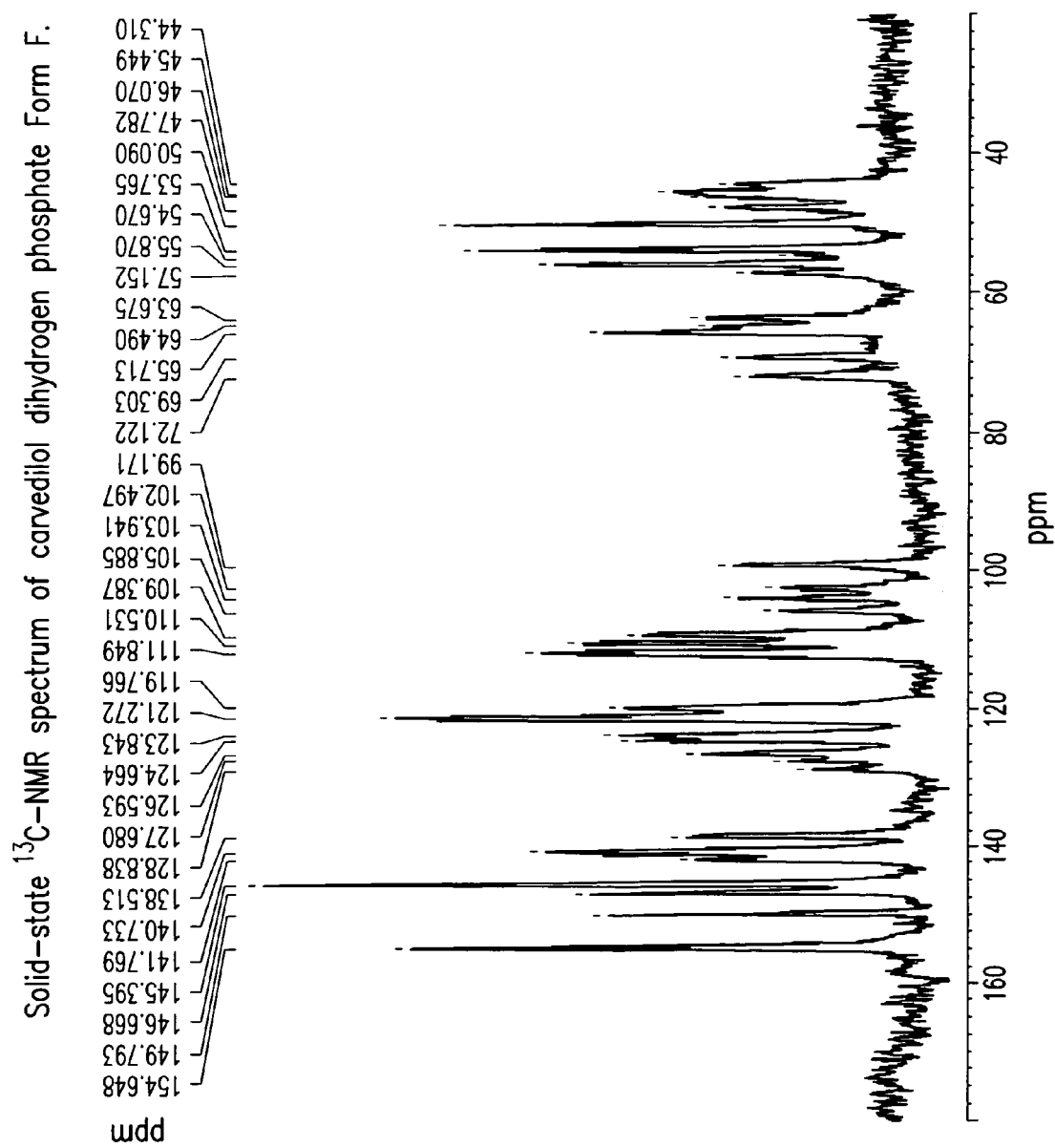
FIG. 25 illustrates a solid-state $^{13}$C-NMR spectrum of carvedilol dihydrogen phosphate Form F.

Form F can be further characterized by data selected from: X-ray powder diffraction reflections at about 10.0, 11.6, 13.6, 15.2 and 27.1 degrees two-theta, ±0.2 degrees two-theta; and X-ray powder diffraction reflections at about 9.9, 11.5, 13.4, 15.1 and 27.0 degrees two-theta, ±0.2 degrees two-theta; a solid-state $^{13}$C-NMR spectrum having chemical shift resonances at about 146.7, 138.5 and 111.8±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 47.5, 39.3 and 12.6±0.1 ppm. The lowest ppm resonance in the chemical shift area of 100 to 180 ppm is typically at about 99.2±1 ppm. Typical powder x-ray diffractograms for Form F are shown in FIGS. 23 and 24. A typical solid-state $^{13}$C-NMR spectrum of Form F is shown in FIGS. 25 and/or 25a.

Form F has a weight loss, as measured by TGA, of about 2.9% by weight, while it has water content, as measured by KF, of about 0.2% by weight. This corresponds to carvedilol dihydrogen phosphate hemimethanolate. GC measurement of residual solvents gives about 30,800-32,300 ppm of methanol confirming presence of hemimethanolate solvate of carvedilol dihydrogen phosphate.

In another embodiment, the invention encompasses a process for crystallizing carvedilol dihydrogen phosphate Form F from a solution of carvedilol, phosphoric acid and methanol.

The carvedilol and phosphoric acid are preferably present in a molar ratio of about 0.8:1 to about 1.2:1, more preferably about 1:1.

The ingredients may be heated in order to achieve dissolution. Stirring may also be employed to promote dissolution. Preferably, the ingredients are heated to reflux. Whether the ingredients are heated, the process may further comprise cooling, to induce crystallization.

Crystallization occurs without addition of water; a minimal amount of water may be present from the phosphoric acid. Preferably, the methanol is anhydrous, i.e., contains less than 2% water by volume.

Crystallization may be carried out for about 5 minutes to about 30 minutes or for about 5 minutes to about 300 minutes.

The carvedilol dihydrogen phosphate may be recovered by any method known to the skilled artisan. Preferably, the carvedilol dihydrogen phosphate is recovered from the mixture by filtration, and then dried under reduced pressure (<1 atmosphere).

In another embodiment, the invention encompasses a process for crystallizing carvedilol dihydrogen phosphate Form F from a solution of carvedilol dihydrogen phosphate and methanol.

The starting material used for the processes for obtaining carvedilol dihydrogen phosphate Form F may be any crystalline or amorphous form of carvedilol dihydrogen phosphate, including various solvates and hydrates. With crystallization processes, the crystalline form of the starting material does not usually affect the final result.

Preferably, the carvedilol dihydrogen phosphate starting material is carvedilol dihydrogen phosphate Form I.

The ingredients may be heated in order to achieve dissolution. Stirring may also be employed to promote dissolution. Preferably, the ingredients are heated to reflux. Whether the ingredients are heated, the process may further comprise cooling, to induce crystallization.

Crystallization occurs without addition of water; a minimal amount of water may be present from the phosphoric acid.

The carvedilol dihydrogen phosphate may be recovered by any method known to the skilled artisan. Preferably, the carvedilol dihydrogen phosphate is recovered from the mixture by filtration, and then dried under reduced pressure (<1 atmosphere).

In another embodiment, the invention encompasses a crystalline form of carvedilol dihydrogen phosphate, referred to herein as Form F1, characterized by data selected from: X-ray powder diffraction reflections at about: 7.6, 9.8, 10.9, 21.2 and 25.0 degrees two theta±0.2 degrees two theta; a solid-state $^{13}$C-NMR spectrum having chemical shift resonances at about 155.3, 145.3 and 127.7±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 52.6, 42.6 and 25±0.1 ppm. The lowest ppm resonance in the chemical shift area of 100 to 180 ppm is typically at about 102.7±1 ppm.

Figure 26:
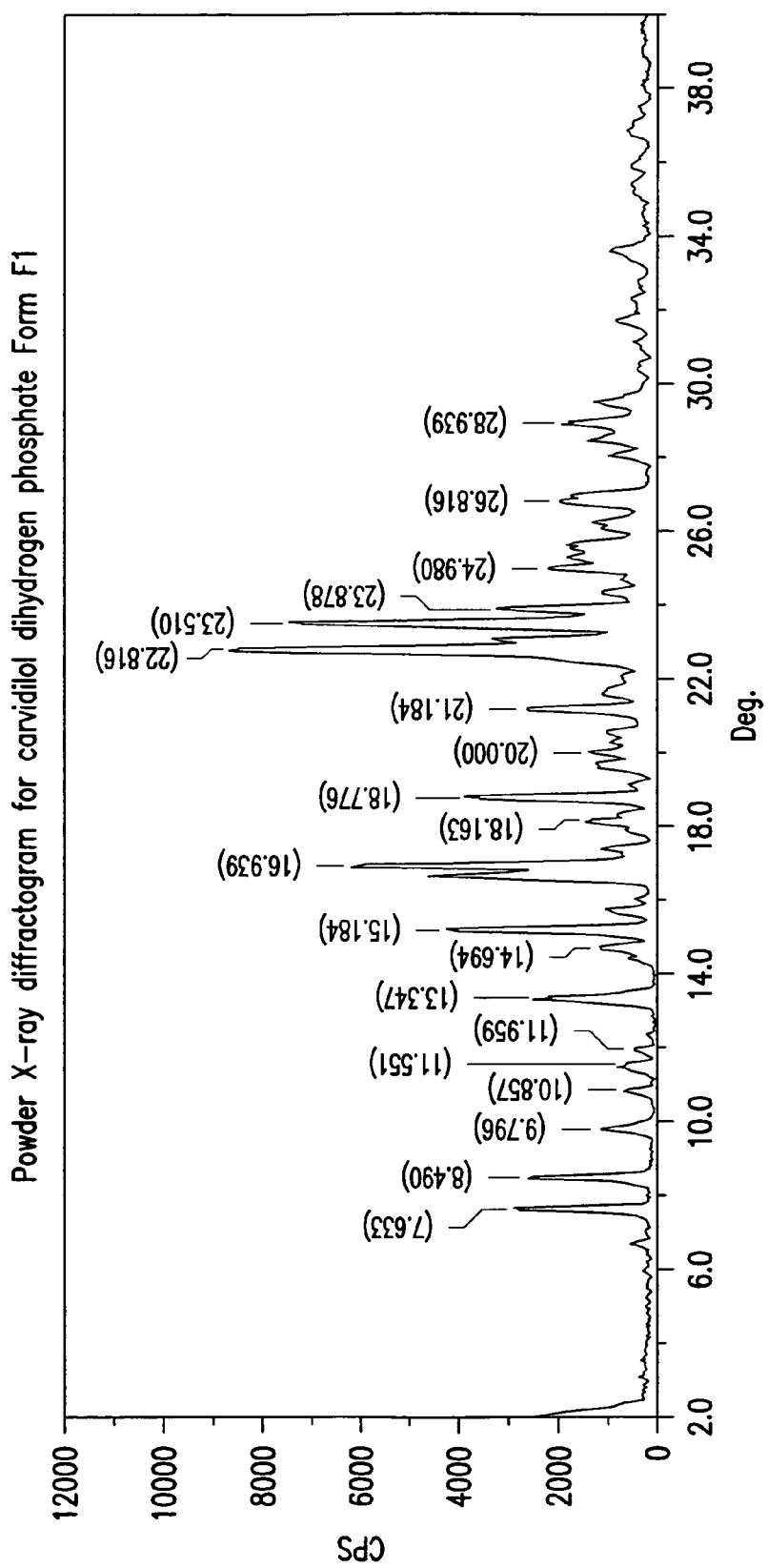
FIG. 26 illustrates a characteristic powder X-ray diffractogram for carvedilol dihydrogen phosphate Form F1 obtained in Example 52.
Figure 27:
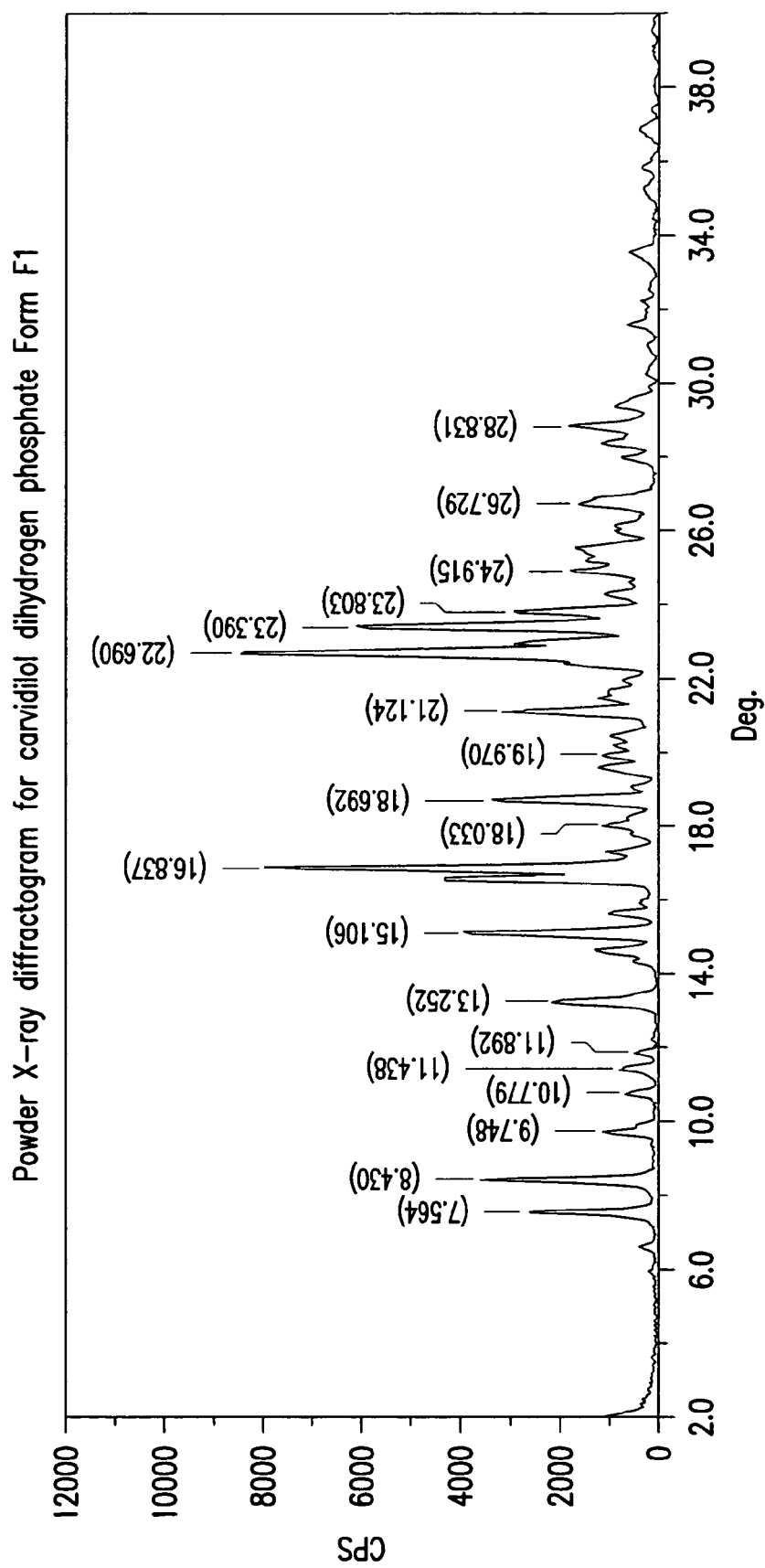
FIG. 27 illustrates a characteristic powder X-ray diffractogram for carvedilol dihydrogen phosphate Form F1 obtained in Example 86.

In another embodiment, Form F1 having X-ray powder diffractogram as substantially shown in FIGS. 26 and 27.

Figure 28:
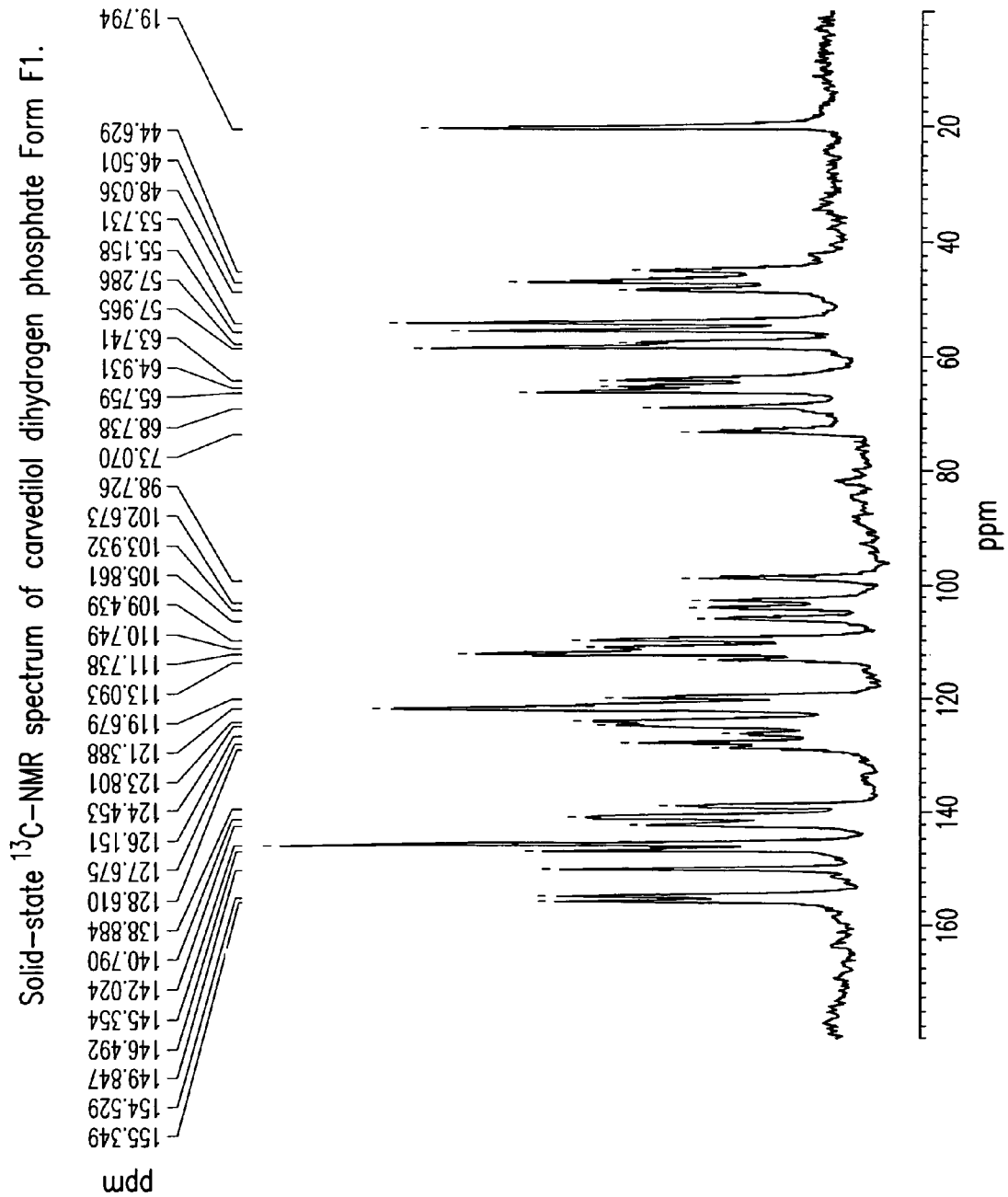
FIG. 28 illustrate a solid-state $^{13}$C-NMR spectrum of carvedilol dihydrogen phosphate Form F1.
Figure 28A:
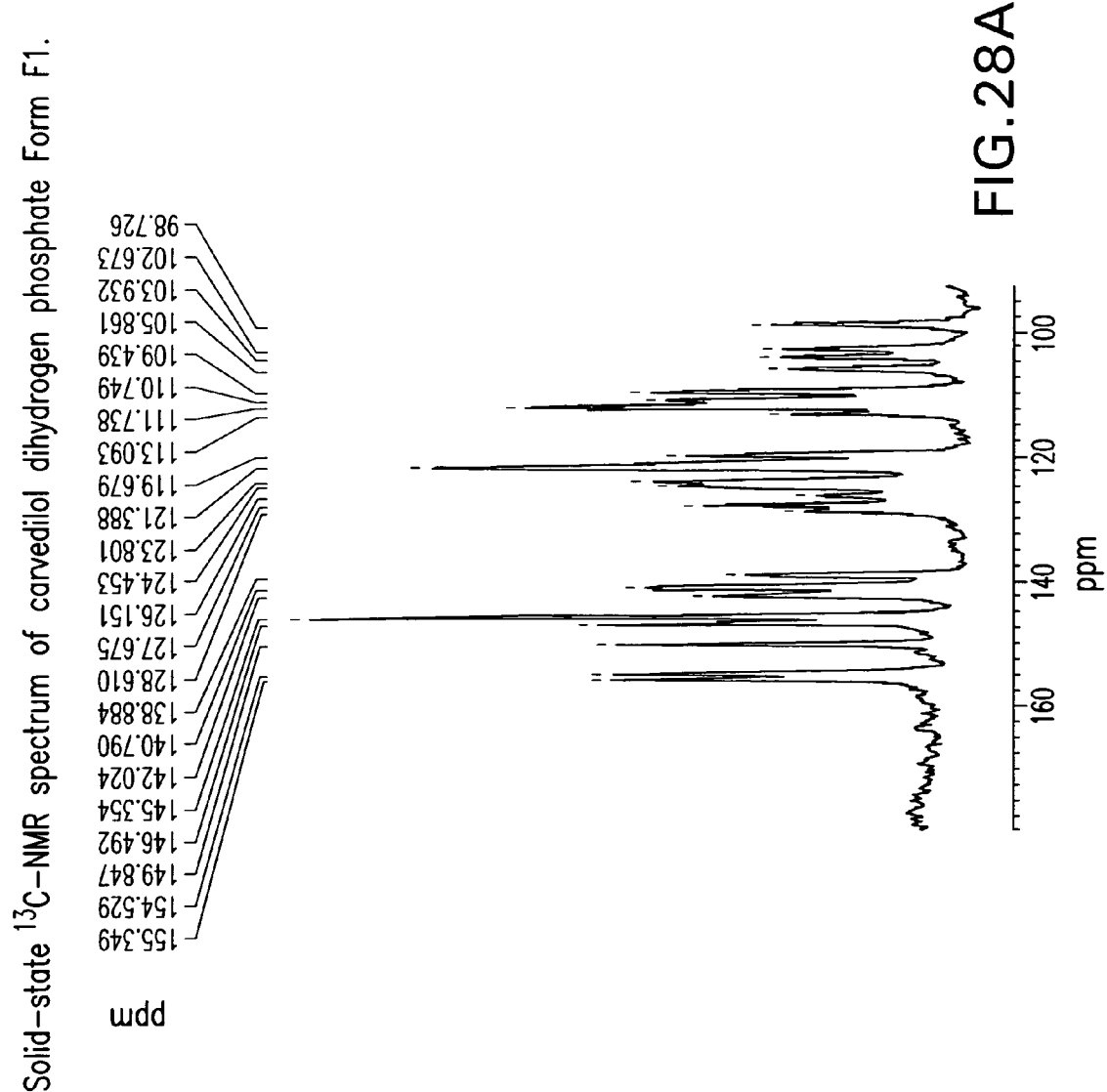
FIG. 28a illustrates a solid-state $^{13}$C-NMR spectrum of carvedilol dihydrogen phosphate Form F1 in the chemical shift area of 100 to 180 ppm.

In another embodiment, Form F1 having solid-state $^{13}$C NMR spectrum as substantially shown in FIGS. 28 and 28a.

Form F1 can also be characterized by X-ray powder diffraction reflections at about: 7.6, 10.9, 13.3, 15.2 and 18.8 degrees two theta±0.2 degrees two theta.

Form F1 can also be characterized by X-ray powder diffraction reflections at about: 7.6, 8.5, 9.8, 15.2 and 16.9±0.2 degrees two theta.

Form F1 can also be characterized by X-ray powder diffraction reflections at about: 7.6, 9.8, 10.9, 14.7, 15.2 and 22.8±0.2 degrees two theta.

Form F1 can also be characterized by X-ray powder diffraction reflections at about: 7.6, 8.5, 9.8, 13.3 and 15.2±0.2 degrees two theta.

Form F1 can be further characterized by X-ray powder diffraction reflections at about 15.7 and 28.0 degrees two-theta, ±0.2 degrees two-theta. A typical powder x-ray diffractogram for Form F1 is shown in FIGS. 26 and 27.

Form F1 can be distinguished from Form F by having four diffraction peaks in the area of about 19-20.7 degrees two-theta, whereas Form F has only three; further, Form F1 has four diffraction peaks in the area of about 24.8-26.0 degrees two-theta, whereas Form F has two; lastly, Form F1 has three diffracted peaks in the area of about 27.8-29.3 degrees two-theta, whereas Form F has two.

Form F1 has a weight loss, as measured by GC measurement of residual solvents between about 42,500-47,000 ppm of ethanol. Hence, Form F1 is hemiethanolate solvate of carvedilol dihydrogen phosphate.

In another embodiment, the invention encompasses a process for preparing carvedilol dihydrogen phosphate Form F1 comprising precipitation from a slurry of carvedilol, phosphoric acid and ethanol, wherein the slurry is stirred for at least about 4 hours.

The carvedilol and phosphoric acid are preferably present in a molar ratio of about 0.8:1 to about 1.2:1, and more preferably about 1:1.

Preferably, absolute ethanol is used.

Preferably, the ingredients are heated to reflux. Whether the ingredients are heated, the process may further comprise cooling, to induce precipitation.

The carvedilol dihydrogen phosphate may be recovered by any method known to the skilled artisan. Preferably, the carvedilol dihydrogen phosphate is recovered from the mixture by filtration, and then dried under reduced pressure (<1 atmosphere).

In another embodiment, the invention encompasses a process for preparing carvedilol dihydrogen phosphate Form F1 comprising precipitation from a slurry of carvedilol dihydrogen phosphate and ethanol, wherein the slurry is maintained for at least about 4 hours.

Preferably, the carvedilol dihydrogen phosphate starting material is carvedilol dihydrogen phosphate Form I, Form N or Form R.

Preferably, absolute ethanol is used.

Preferably, the ingredients are heated to reflux. Whether the ingredients are heated, the process may further comprise cooling, to induce precipitation.

The carvedilol dihydrogen phosphate may be recovered by any method known to the skilled artisan. Preferably, the carvedilol dihydrogen phosphate is recovered from the mixture by filtration, and then dried under reduced pressure (<1 atmosphere).

In one embodiment, carvedilol base is combined with ethanol and heated to obtain a solution. Heating is preferably carried out of about 65° C. to about 82° C. (reflux temperature), preferably about 78-82° C. Phosphoric acid and optionally an additional amount of ethanol are added to the solution. The solution is cooled, preferably to about 10° C. to about 20° C. The product is then recovered as described above.

Figure 35:
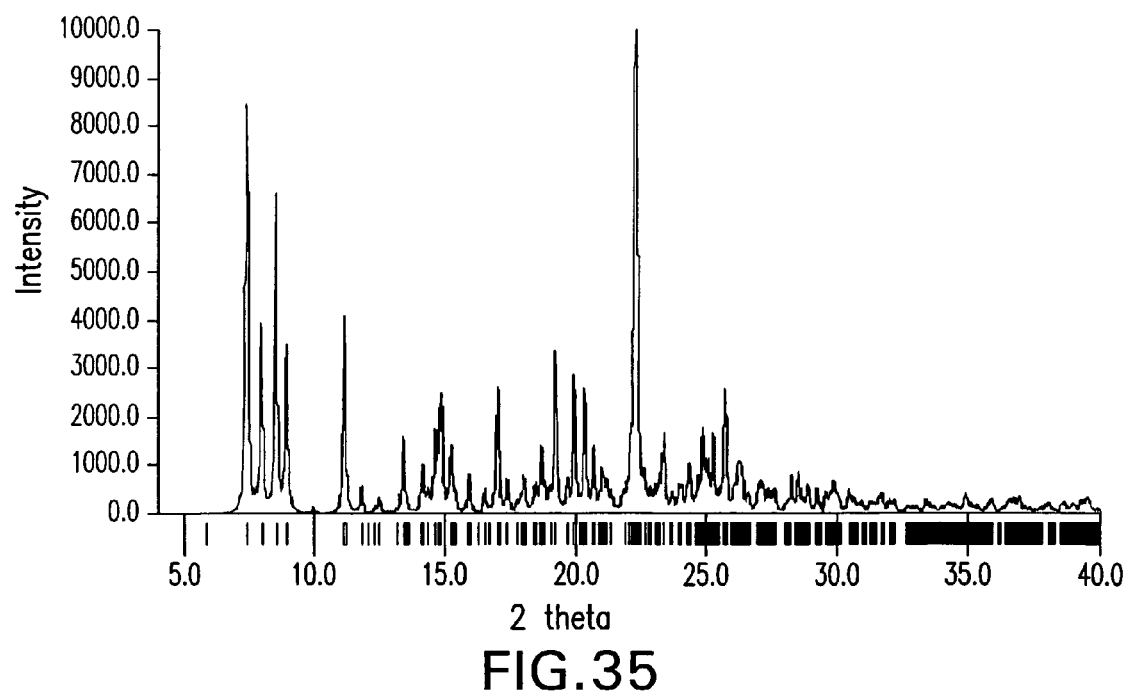
FIG. 35 illustrates a characteristic powder X-ray diffractogram for the carvedilol hydrogen phosphate Form F2.

In another embodiment the present invention provides a crystalline form of Carvedilol phosphate salt, referred to herein as Form F2. Form F2 is characterized by an X-Ray powder diffraction pattern with peaks at about: 7.4, 7.9, 8.5, 8.9 and 11.1±0.2 degrees two theta. The Calculated X-ray powder diffraction pattern of Carvedilol phosphate salt Form F2 is substantially depicted in FIG. 35. The structure was solved by direct methods for triclinic P-1 group with the unit cell parameters: a=13.281(3), b=14.315(3), c=16.406(4)Å, α=66.85(2), β=85.94(2) γ=65.44(4) [deg], and cell volume 2592.4(12) Å$^3$. Form F2 is carvedilol dihydrogen phosphate hemiethanolate.

Form F2 is prepared by dissolution of Carvedilol dihydrogen phosphate in ethanol at elevated temperature, of about 25° C. to about reflux temperature, preferably about 70° C., followed by cooling. Carvedilol dihydrogen phosphate Form I can be used as starting material. Cooling is preferably carried out in about one to about 10 days, preferably about 6 days. A final temperature can be about 10° C. to about 30° C., preferably about 20° C. The crystal form can then be recovered by conventional techniques.

In another embodiment, the invention encompasses a crystalline form of carvedilol dihydrogen phosphate, denominated Form L, characterized by data selected from the group consisting of: X-ray powder diffraction reflections at about: 4.6, 7.5, 8.7, 11.6 and 15.6 degrees two theta±0.2 degrees two theta; a solid-state $^{13}$C-NMR spectrum having chemical shift resonances at about 156.6, 150.3 and 102.5±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 54.1, 47.8 and 0.0±0.1 ppm. The lowest ppm resonance in the chemical shift area of 100 to 180 ppm is typically at about 102.5±1 ppm.

Figure 13:
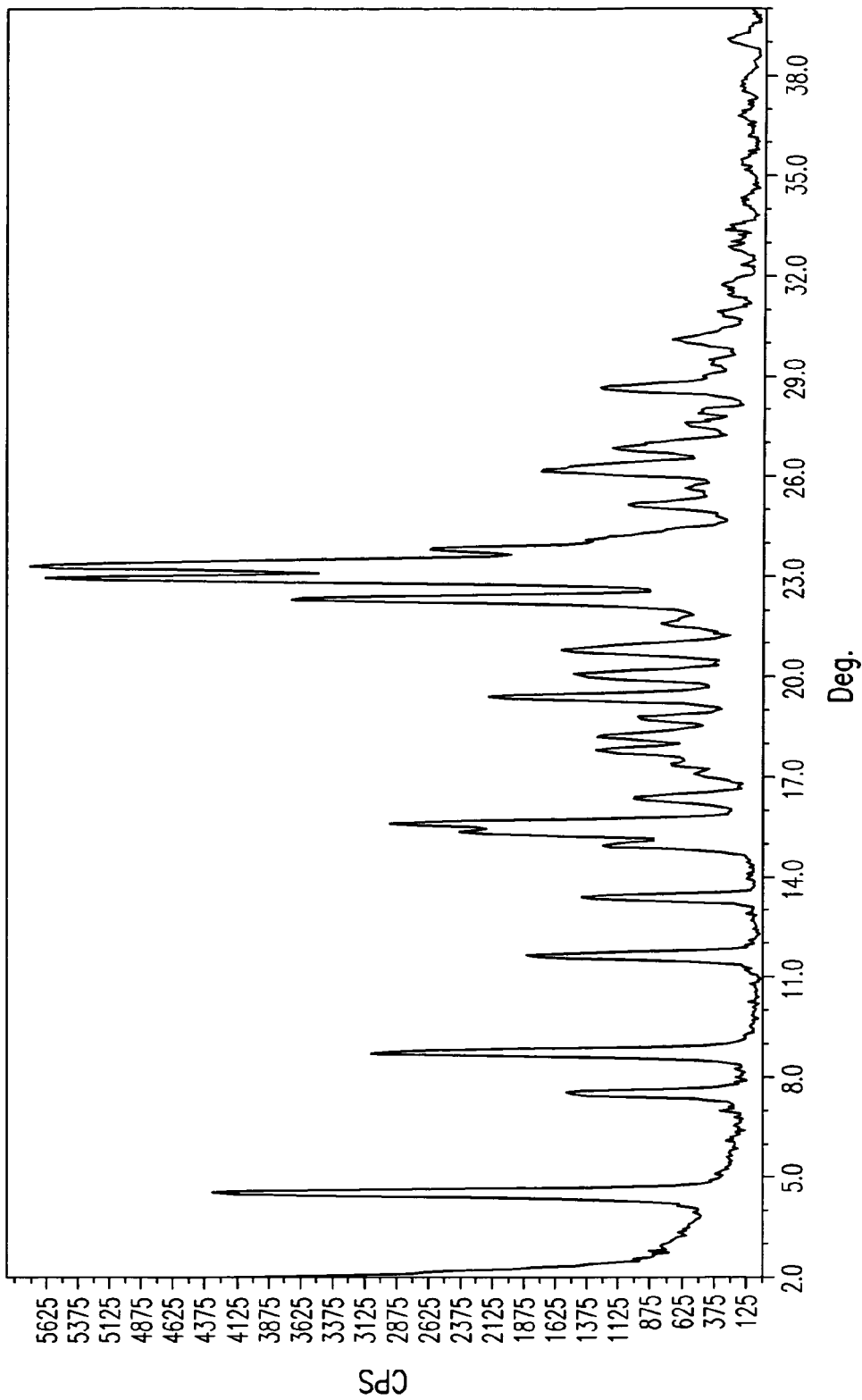
FIG. 13 illustrates a characteristic powder X-ray diffractogram for carvedilol dihydrogen phosphate Form L.
Figure 14:
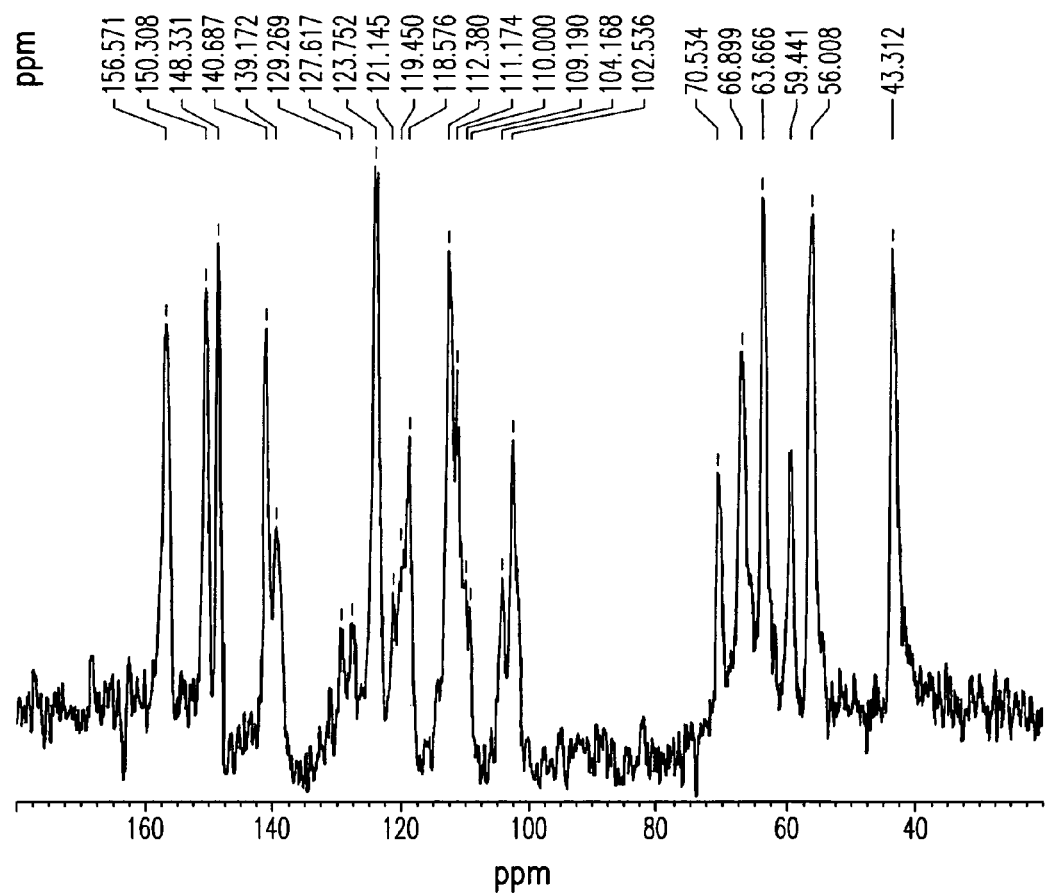
FIG. 14 illustrates a solid-state $^{13}$C-NMR spectrum of carvedilol dihydrogen phosphate Form L.
Figure 14A:
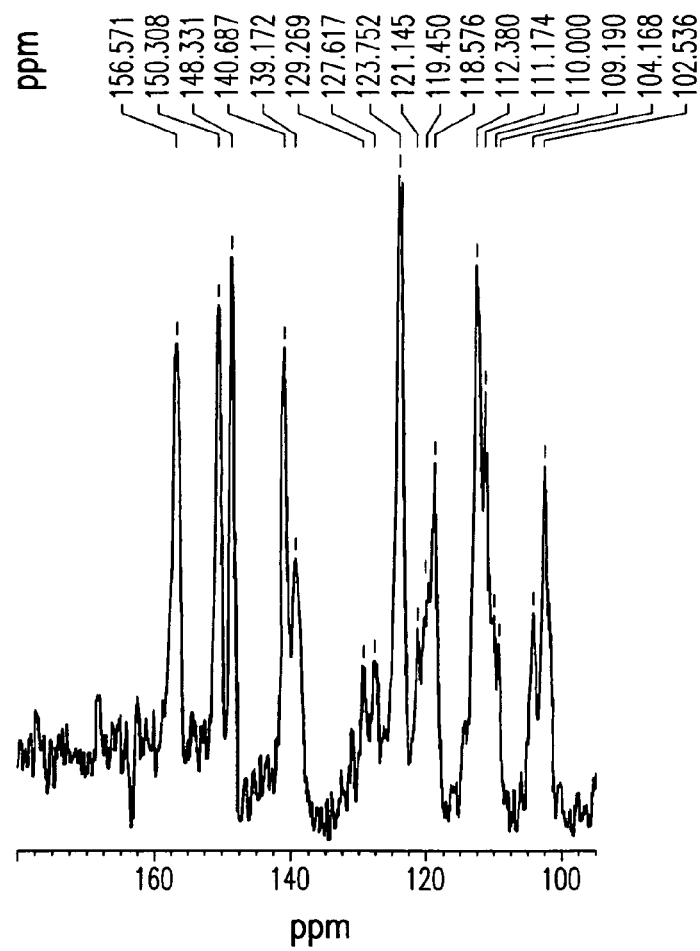
FIG. 14a illustrate a solid-state $^{13}$C-NMR spectrum of carvedilol dihydrogen phosphate Form L in the chemical shift area of 100 to 180 ppm.

A typical powder x-ray diffractogram for Form L is shown in FIG. 13. A typical solid-state $^{13}$C-NMR spectrum of Form L is shown in FIG. 14 and or 14a.

Form L can also be characterized by any five peaks selected from the following list of PXRD peaks at about: 4.6, 7.5, 8.7, 11.6 13.4, 15.6 and 19.4±0.2 degrees two theta.

Form L can also be characterized by data selected from: X-ray powder diffraction reflections at about: 4.6, 7.5, 8.7, 11.6 and 15.0 degrees two theta±0.2 degrees two theta.

Form L can also be characterized by data selected from: X-ray powder diffraction reflections at about: 4.6, 7.5, 8.7, 15.0 and 22.9 degrees two theta±0.2 degrees two theta.

Form L can be further characterized by data selected from the group consisting of: X-ray powder diffraction reflections at about 13.4, 19.4, 22.3, 22.9 and 23.3 degrees two-theta, ±0.2 degrees two-theta; a solid-state $^{13}$C-NMR spectrum having chemical shift resonances at about 148.3, 139.2 and 112.4±0.2 ppm; and a solid-state $^{13}$C NMR spectrum having chemical shift differences between the lowest ppm resonance in the chemical shift area of 100 to 180 ppm and another in the chemical shift area of 100 to 180 ppm of 45.8, 36.7 and 9.9±0.1 ppm. The lowest ppm resonance in the chemical shift area of 100 to 180 ppm is typically at about 102.5±1 ppm.

GC measurement of residual solvents of Form L gives about 137500 ppm of dioxane. Form L is a dioxane solvate of carvedilol dihydrogen phosphate In another embodiment, the invention encompasses a process for preparing carvedilol dihydrogen phosphate Form L comprising: combining carvedilol, phosphoric acid and dioxane and precipitating carvedilol dihydrogen phosphate Form L from the reaction mixture. In this embodiment less than about 30 g of carvedilol dihydrogen phosphate and less than about 300 ml dioxane are used.

Precipitation may also be obtained from a slurry of carvedilol dihydrogen phosphate and dioxane.

Whenever precipitation occurs from a slurry of carvedilol, phosphoric acid and dioxane, the carvedilol and phosphoric acid are preferably present in a molar ratio of about 1:1.

The ingredients are preferably heated to reflux, and further maintained for about 12 hours.

The carvedilol dihydrogen phosphate may be recovered by any method known to the skilled artisan. Preferably, the carvedilol dihydrogen phosphate is recovered from the mixture by filtration, and then dried under reduced pressure (<1 atmosphere).

In another embodiment, the invention encompasses a crystalline form of carvedilol dihydrogen phosphate, referred to herein as Form L1, characterized by data selected from the group consisting of: X-ray powder diffraction reflections at about: 4.6, 8.7, 11.6, 14.6 and 15.3 degrees two theta±0.2 degrees two theta; a solid-state $^{13}$C-NMR spectrum having chemical shift resonances at about 156.6, 150.3 and 148.4±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 53.2, 46.9 and 45.0±0.1 ppm. The lowest ppm resonance in the chemical shift area of 100 to 180 ppm is typically at about 103.4±1 ppm.

Figure 15:
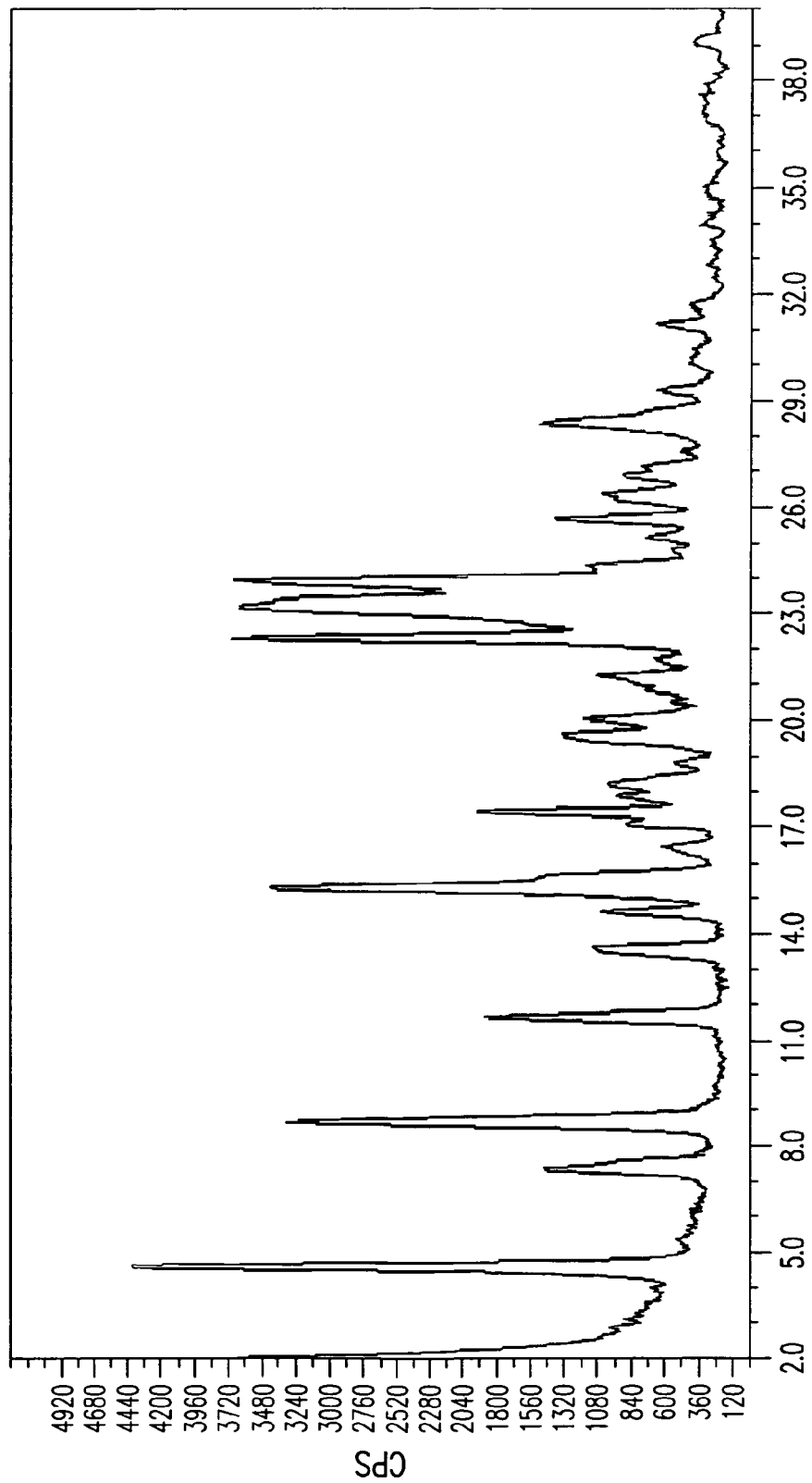
FIG. 15 illustrates a characteristic powder X-ray diffractogram for carvedilol dihydrogen phosphate Form L1.

Form L1 has an X-ray powder diffractogram as substantially shown in FIG. 15. Form L1 has a solid-state $^{13}$C NMR spectrum as substantially shown in FIG. 16 and or 16a.

Form L1 can also be characterized by PXRD peaks at about: 4.6, 7.4, 8.7, 11.6 14.6, 15.3 and 19.4±0.2 degrees two theta.

Form L1 can also be characterized by PXRD peaks at about 4.6, 7.4, 8.7, 13.6 and 15.3 degrees two theta±0.2 degrees two theta.

Form L1 can also be characterized by PXRD peaks at about 4.6, 7.4, 8.7, 11.6 and 17.4.

Form L1 can also be characterized by PXRD peaks at about 4.6, 7.4, 8.7, 15.3 and 17.4 degrees two theta±0.2 degrees two theta.

Form L1 can be further characterized by data selected from the group consisting of: X-ray powder diffraction reflections at about 7.4, 13.6, 21.3 and 28.4 degrees two-theta, ±0.2 degrees two-theta; a solid-state $^{13}$C-NMR spectrum having chemical shift resonances at about 140.3, 139.1, 123.5 and 112.5±0.2 ppm; and a solid-state $^{13}$C NMR spectrum having chemical shift differences between the lowest ppm resonance in the chemical shift area of 100 to 180 ppm and another in the chemical shift area of 100 to 180 ppm of 36.9, 35.7 20.1 and 9.1±0.1 ppm. The lowest ppm resonance in the chemical shift area of 100 to 180 ppm is typically at about 103.4±1 ppm.

Figure 16:
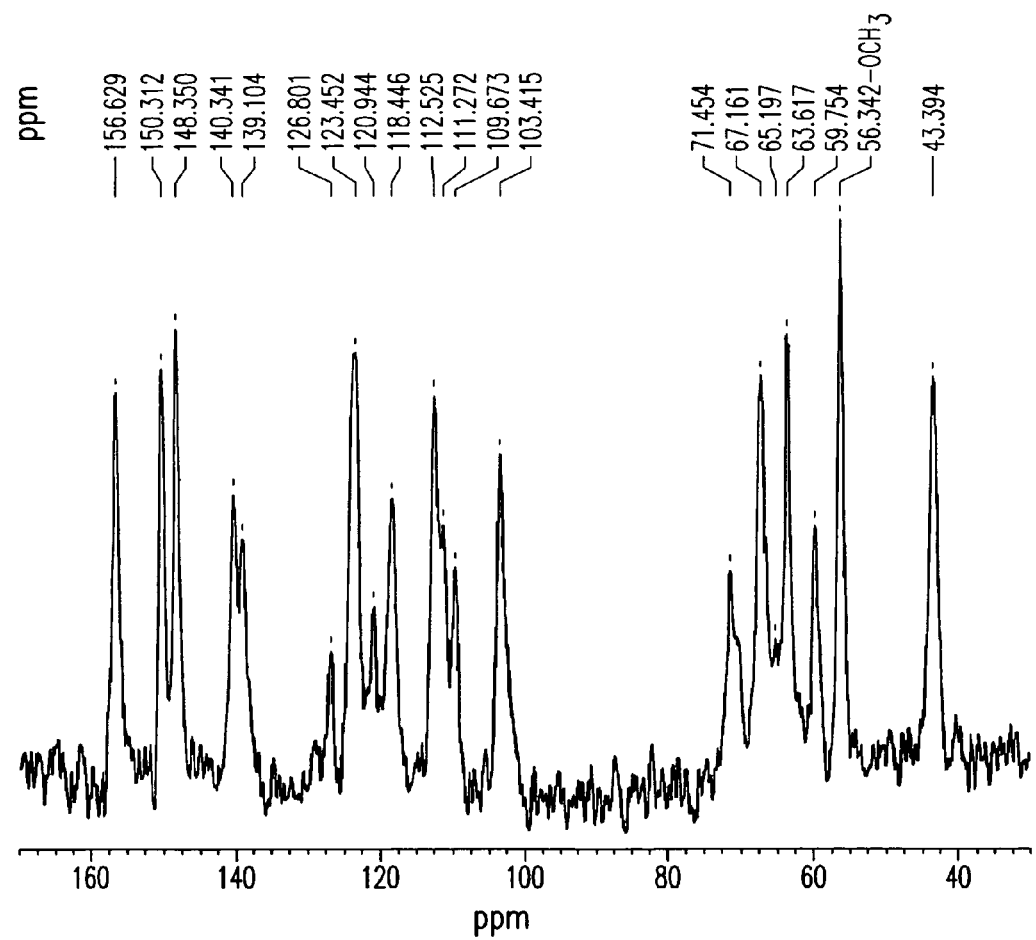
FIG. 16 illustrates a solid-state $^{13}$C-NMR spectrum of carvedilol dihydrogen phosphate Form L1.
Figure 16A:
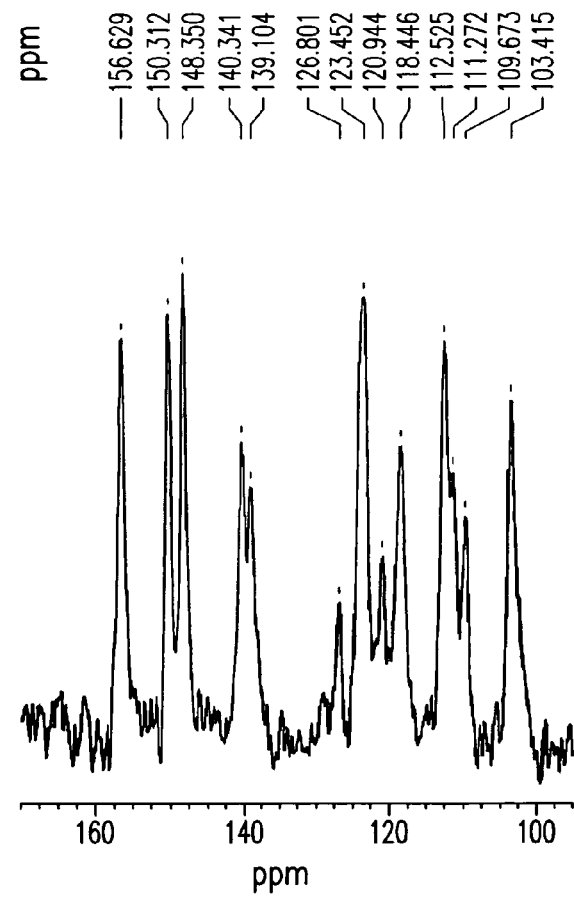
FIG. 16a illustrates a solid-state $^{13}$C-NMR spectrum of carvedilol dihydrogen phosphate Form L1 in the chemical shift area of 100 to 180 ppm.

A typical powder x-ray diffractogram for Form L1 is shown in FIG. 15. A typical solid-state $^{13}$C-NMR spectrum of Form L1 is shown in FIG. 16 and or 16a.

Form L1 has a weight loss, as measured by TGA, of about 9.7% by weight, while it has water content, as measured by KF, of about 0.4% by weight. Form L1 is a dioxane solvate of carvedilol dihydrogen phosphate.

Form L1 can be obtained by a scaled up version of the process for producing Form L. Accordingly, the invention also encompasses a process for preparing carvedilol dihydrogen phosphate Form L1 comprising slurrying at least about 30 g carvedilol dihydrogen phosphate, preferably Form I, in at least about 300 ml dioxane. Preferably, the slurry is heated to reflux.

The carvedilol dihydrogen phosphate may be recovered by any method known to the skilled artisan. Preferably, the carvedilol dihydrogen phosphate is recovered from the mixture by filtration, and then dried, preferably at about 55° C., under reduced pressure (<1 atmosphere).

In another embodiment, the invention encompasses a crystalline form of carvedilol dihydrogen phosphate, denominated Form N, characterized by data selected from the group consisting of: X-ray powder diffraction reflections at about: 6.0, 6.9, 15.2, 16.3 and 17.4 degrees two theta±0.2 degrees two theta; a solid-state $^{13}$C-NMR spectrum having chemical shift resonances at about 154.4, 146.9 and 138.4±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 52.9, 45.4 and 36.9±0.1 ppm. The lowest ppm resonance in the chemical shift area of 100 to 180 ppm is typically at about 101.5±1 ppm; a solid-state $^{13}$C-NMR spectrum having chemical shift resonances at about 154.4, 146.9, 138.4 and 110.9±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 52.9, 45.4, 36.9 and 9.4±0.1 ppm. The lowest ppm resonance in the chemical shift area of 100 to 180 ppm is typically at about 101.5±1 ppm.

Figure 17:
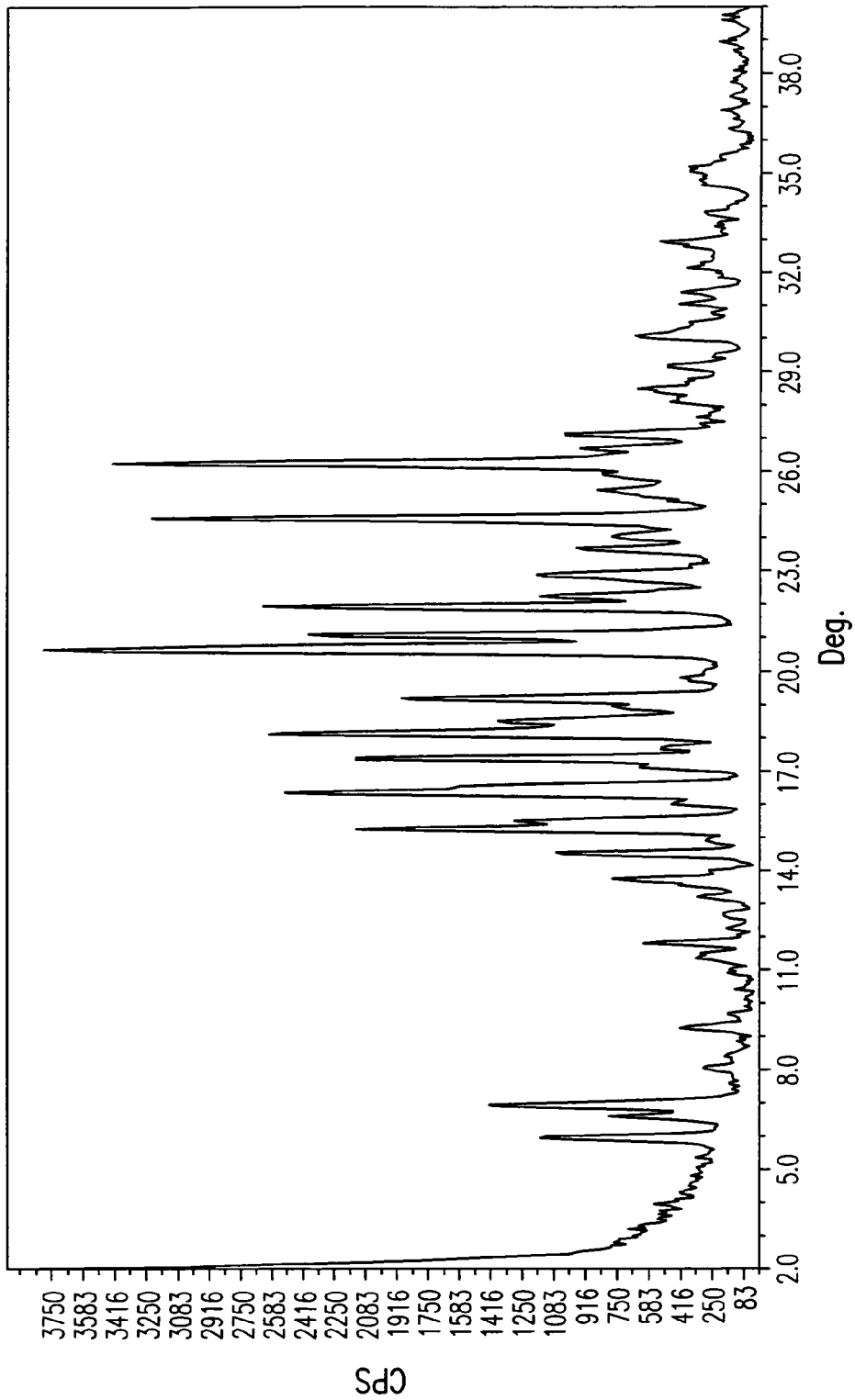
FIGS. 17 and 18 illustrate a characteristic powder X-ray diffractogram for carvedilol dihydrogen phosphate Form N.
Figure 18:
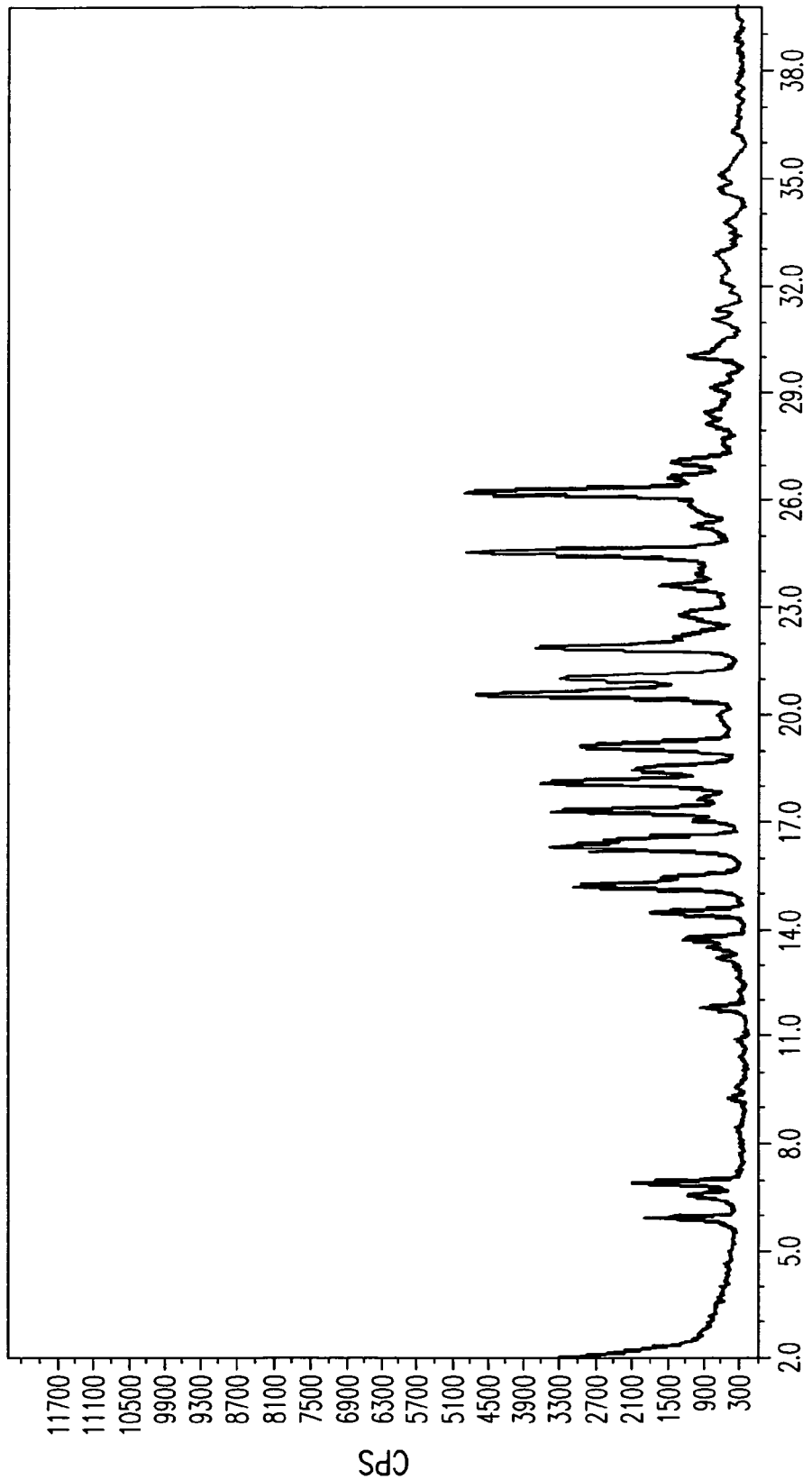

Form N has an X-ray powder diffractogram as substantially shown in FIGS. 17 and 18. Form N also has a solid-state $^{13}$C NMR spectrum as substantially shown in FIG. 19 and or 19a.

In another embodiment, the invention encompasses a crystalline form of carvedilol dihydrogen phosphate, referred to herein as Form N, characterized by data selected from: X-ray powder diffraction reflections at about: 6.0, 6.9, 13.7 15.2 and 18.1 degrees two theta±0.2 degrees two theta.

In another embodiment, the invention encompasses a crystalline form of carvedilol dihydrogen phosphate, referred to herein as Form N, characterized by data selected from: X-ray powder diffraction reflections at about: 6.0, 6.9, 13.7, 15.2 and 17.4±0.2 degrees two theta.

Figure 19:
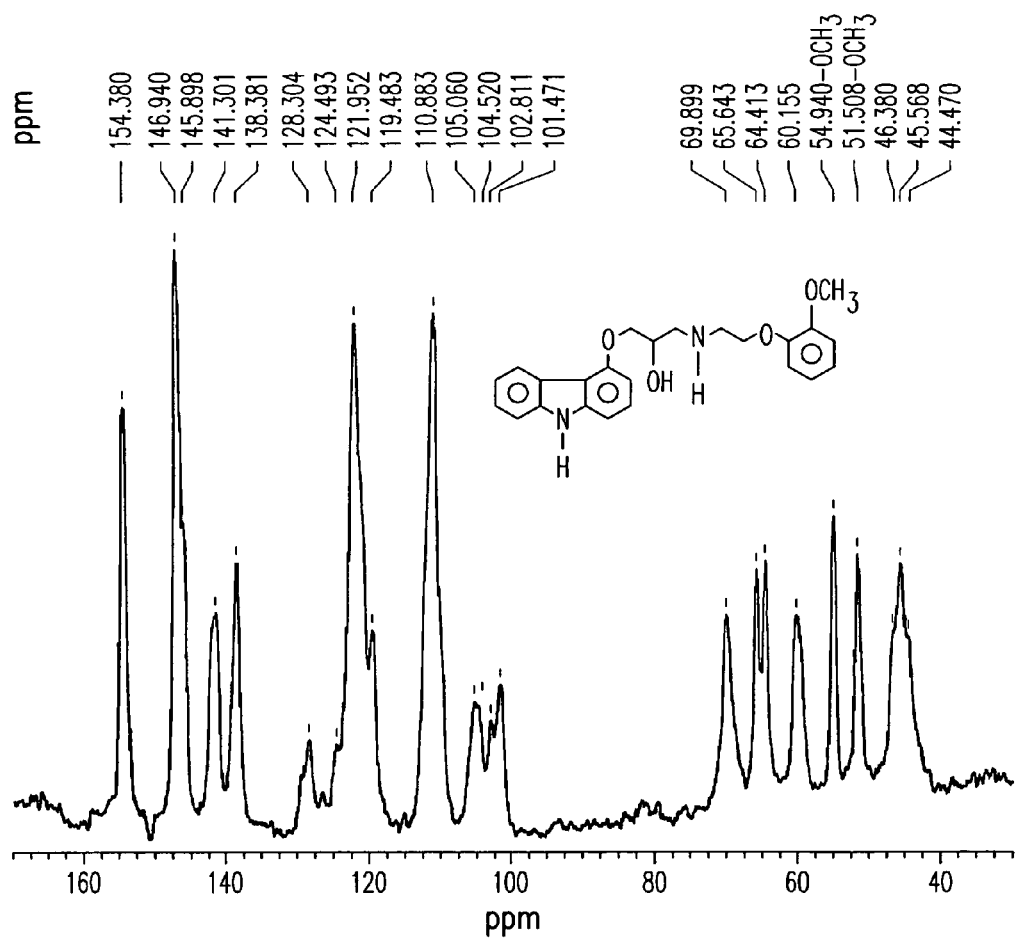
FIG. 19 illustrates a solid-state $^{13}$C-NMR spectrum of carvedilol dihydrogen phosphate Form N.
Figure 19A:
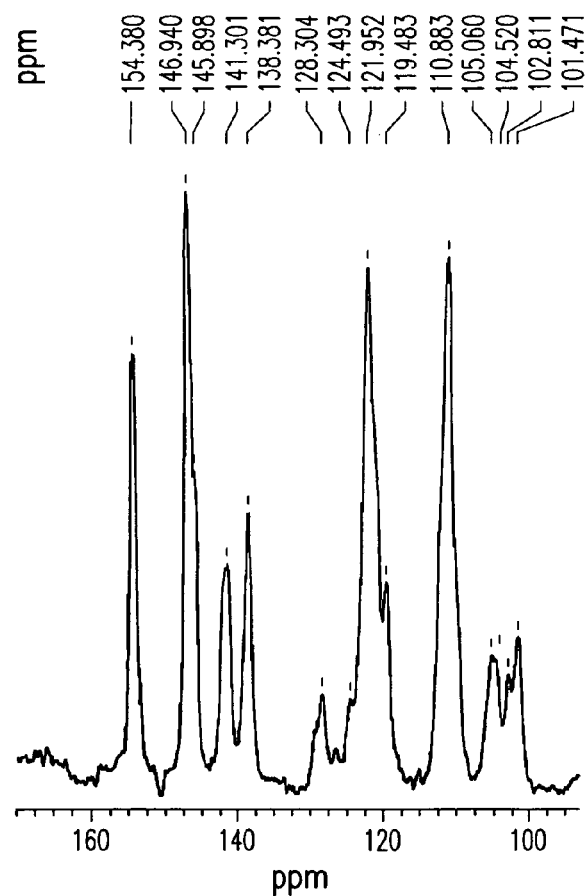
FIG. 19a illustrates a solid-state $^{13}$C-NMR spectrum of carvedilol dihydrogen phosphate Form N in the chemical shift area of 100 to 180 ppm.

Form N can be further characterized by data selected from the group consisting of: X-ray powder diffraction reflections at about 18.1, 20.6, 24.6 and 26.3 degrees two-theta, ±0.2 degrees two-theta; a solid-state $^{13}$C-NMR spectrum having chemical shift resonances at about 141.3, 122.0 and 110.9±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 39.8, 20.5 and 9.4±0.1 ppm. The lowest ppm resonance in the chemical shift area of 100 to 180 ppm is typically at about 101.5±1 ppm, or substantially as depicted in FIG. 19a.

A typical powder x-ray diffractogram for Form N is shown in FIGS. 17 and 18. A typical solid-state $^{13}$C-NMR spectrum of Form N is shown in FIGS. 19 and 19a.

Form N has a weight loss, as measured by TGA, of about 5.0-6.6% by weight, while it has water content, as measured by KF, between 4.7-6.9% by weight. This corresponds to carvedilol dihydrogen phosphate dihydrate.

In another embodiment, the invention encompasses a process for preparing carvedilol dihydrogen phosphate Form N comprising exposing carvedilol dihydrogen phosphate Form L to high relative humidity (e.g., greater than about 80%, greater than about 90%, greater than about 95% or about 100% relative humidity), preferably for at least about 7 days.

In another embodiment, the invention encompasses a process for preparing carvedilol dihydrogen phosphate Form N comprising exposing carvedilol dihydrogen phosphate Form F1, L1 or R to high relative humidity (e.g., greater than about 80%, greater than about 90%, greater than about 95% or about 100% relative humidity), preferably for at least about 7 days.

In another embodiment, the invention encompasses a process for preparing carvedilol dihydrogen phosphate Form N comprising exposing amorphous carvedilol dihydrogen phosphate to high relative humidity (e.g., greater than 80%, greater than 90%, greater than 95% or about 100% relative humidity), preferably for about 7 days.

In another embodiment, the invention encompasses a process for preparing carvedilol dihydrogen phosphate Form N comprising drying carvedilol dihydrogen phosphate Form O. Preferably, carvedilol dihydrogen phosphate Form O is heated to a temperature of from about 30° C. to about 70° C., more preferably to about 35° C., for a time sufficient to obtain carvedilol dihydrogen phosphate Form N. Carvedilol dihydrogen phosphate Form O may be prepared as described below. As one skilled in the art will appreciate, the time required to obtain carvedilol dihydrogen phosphate Form N will vary depending upon, among other factors, the amount of wet carvedilol dihydrogen phosphate Form O to be dried and the drying temperature, and can be determined by taking periodic XRDs.

In another embodiment, the invention encompasses a crystalline form of carvedilol dihydrogen phosphate, denominated Form O, characterized by X-ray powder diffraction reflections at about: 6.1, 12.2, 12.9, 16.2 and 18.0 degrees two theta±0.2 degrees two theta. Form O can be further characterized by X-ray powder diffraction reflections at about 20.1, 23.0, 23.7, 24.5 and 26.5 degrees two-theta, ±0.2 degrees two-theta. A typical powder x-ray diffractogram for Form O is shown in FIG. 20.

Figure 20:
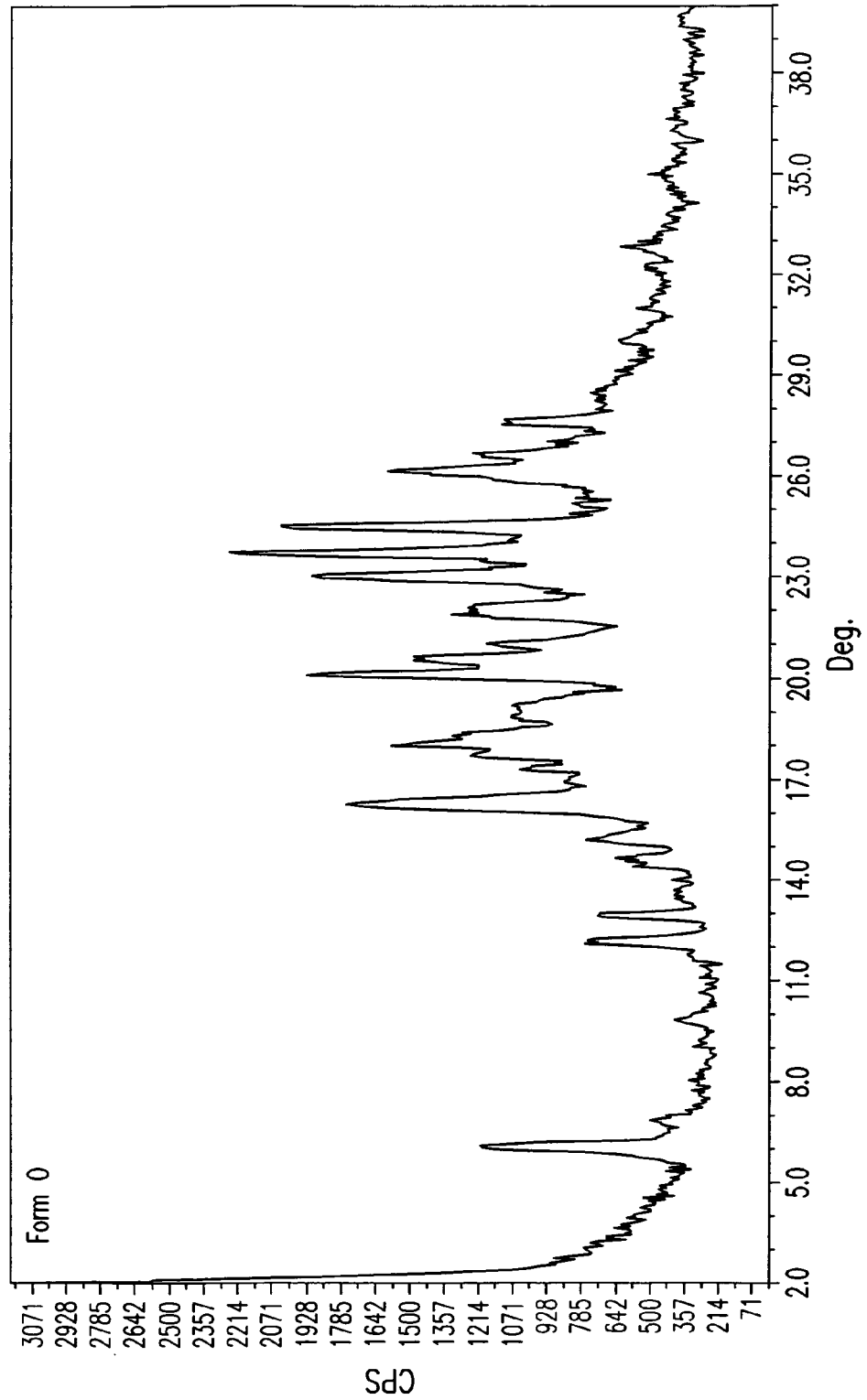
FIG. 20 illustrates a characteristic powder X-ray diffractogram for carvedilol dihydrogen phosphate Form O.

X-ray powder diffractogram of Form O is substantially shown in FIG. 20.

In another embodiment, the invention encompasses a process for preparing carvedilol dihydrogen phosphate Form O comprising grinding the amorphous form of carvedilol dihydrogen phosphate in the presence of water, for about 1-2 minutes.

Preferably, the amorphous form is ground in the presence of 2-3 drops of water. Preferably, about 2-3 drops of water per 200 mg of amorphous form is used.

In another embodiment, the invention encompasses a crystalline form of carvedilol dihydrogen phosphate, referred to herein as Form P, characterized by data selected from the group consisting of: X-ray powder diffraction reflections at about: 5.3, 10.4, 16.8, 26.0 and 31.8 degrees two theta±0.2 degrees two theta; a solid-state $^{13}$C-NMR spectrum having chemical shift resonances at about 154.7, 146.6 and 122.2±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 54.7, 46.6 and 22.2±0.1 ppm. The lowest ppm resonance in the chemical shift area of 100 to 180 ppm is typically at about 100.0±1 ppm.

Figure 21:
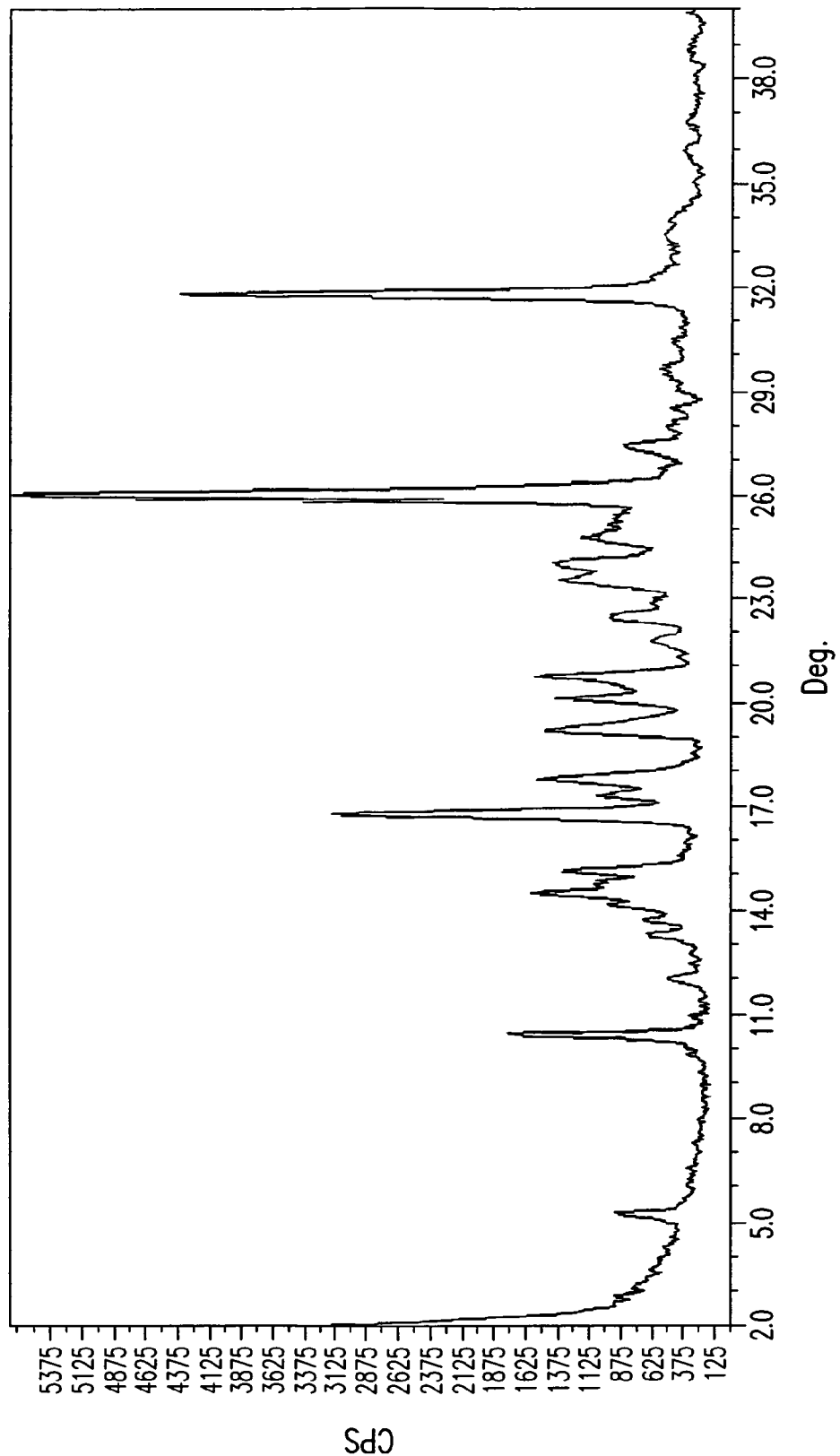
FIG. 21 illustrates a characteristic powder X-ray diffractogram for carvedilol dihydrogen phosphate Form P.

Form P has a X-ray powder diffractogram as substantially shown in FIG. 21. Form P has a solid-state $^{13}$C NMR spectrum as substantially shown in FIGS. 22 and 22a.

Form P can also be characterized by any five peaks selected from the following list of PXRD peaks at about: 5.3, 10.4, 14.5, 16.8, 17.8, 26.0 and 31.8±0.2 degrees two theta.

Form P can also be characterized by X-ray powder diffraction reflections at about: 5.3, 10.4, 15.2, 17.8 and 22.5 degrees two theta±0.2 degrees two theta.

Form P can also be characterized by X-ray powder diffraction reflections at about: 5.3, 14.5, 15.2, 16.8 and 17.3 degrees two theta±0.2 degrees two theta.

Form P can also be characterized by X-ray powder diffraction reflections at about: 5.3, 10.4, 14.5, 15.2 and 17.8 degrees two theta±0.2 degrees two theta.

Form P can also be characterized by X-ray powder diffraction reflections at about: 5.3, 14.5, 15.2, 17.8 and 20.1 degrees two theta±0.2 degrees two theta.

Figure 22:
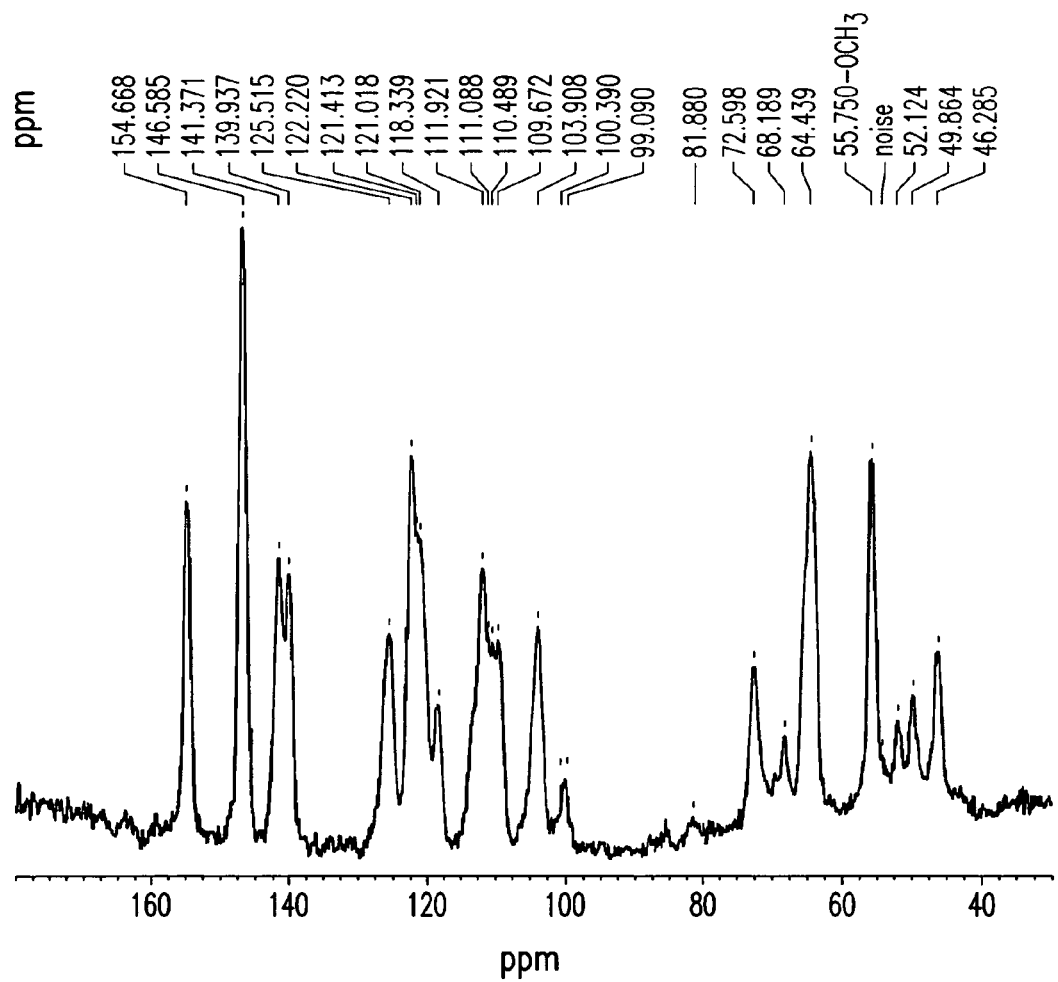
FIG. 22 illustrates a solid-state $^{13}$C-NMR spectrum of carvedilol dihydrogen phosphate Form P.
Figure 22A:
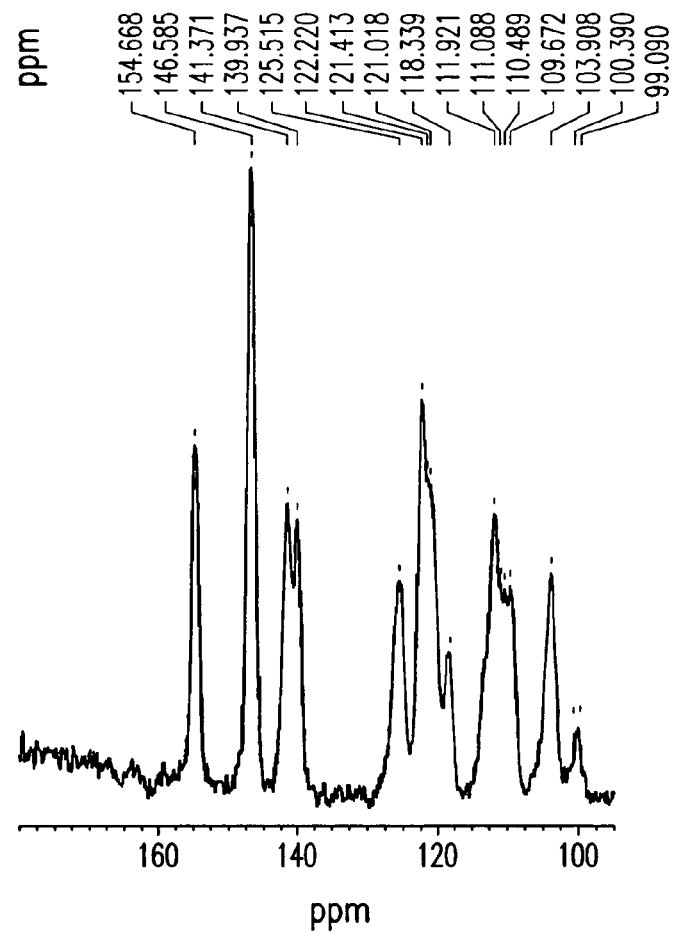
FIG. 22a illustrates a solid-state $^{13}$C-NMR spectrum of carvedilol dihydrogen phosphate Form P in the chemical shift area of 100 to 180 ppm.

Form P can be further characterized by data selected from the group consisting of: X-ray powder diffraction reflections at about 14.5 and 17.8 degrees two-theta, ±0.2 degrees two-theta; a solid-state $^{13}$C-NMR spectrum having chemical shift resonances at about 141.4, 139.9 and 111.9±0.2 ppm; and a solid-state $^{13}$C-NMR spectrum having chemical shift differences between the lowest ppm resonance in the chemical shift area of 100 to 180 ppm and another in the chemical shift area of 100 to 180 ppm of about 41.4, 39.9 and 11.9±0.1 ppm. The lowest ppm resonance in the chemical shift area of 100 to 180 ppm is typically at about 100.0±1 ppm. A typical powder x-ray diffractogram for Form P is shown in FIG. 21. A typical solid-state $^{13}$C-NMR spectrum of Form P is shown in FIG. 22 and or 22a.

Form P has a weight loss, as measured by TGA, of about 2.0% by weight, while it has water content, as measured by KF, of about 1.7% by weight. Form P is carvedilol dihydrogen phosphate hemihydrate.

In another embodiment, the invention encompasses a process for preparing carvedilol dihydrogen phosphate Form P comprising slurrying amorphous carvedilol dihydrogen phosphate in ethanol. Preferably, the reaction occurs at room temperature.

The carvedilol dihydrogen phosphate may be recovered by any method known to the skilled artisan. Preferably, the carvedilol dihydrogen phosphate is recovered from the mixture by filtration, and then dried under reduced pressure (<1 atmosphere).

In another embodiment, the invention encompasses a crystalline form of carvedilol dihydrogen phosphate, referred to herein as Form R, characterized by data selected from: X-ray powder diffraction reflections at about: 5.8, 11.8, 16.8, 18.6 and 23.2 degrees two theta±0.2 degrees two theta; a solid-state $^{13}$C-NMR spectrum having chemical shift resonances at about 153.7, 147.9 and 122.8±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 51.0, 45.2 and 20.1±0.1 ppm. The lowest ppm resonance in the chemical shift area of 100 to 180 ppm is typically at about 102.7±1 ppm.

Figure 29:
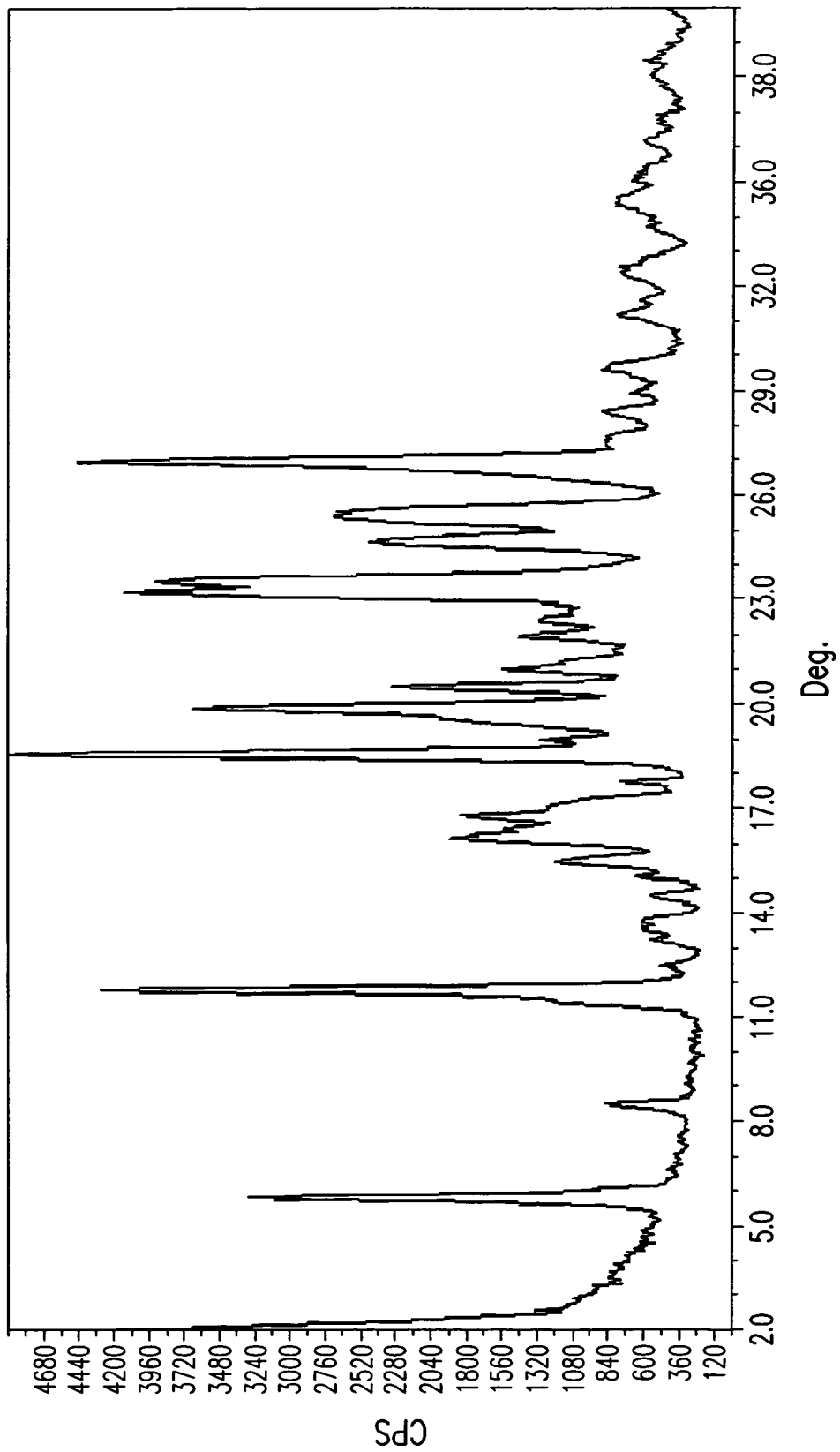
FIG. 29 illustrates a characteristic powder X-ray diffractogram for carvedilol dihydrogen phosphate Form R.

Form R has an X-ray powder diffractogram as substantially shown in FIG. 29. Form R has a solid-state $^{13}$C NMR spectrum as substantially shown in FIG. 30 and or 30a.

Form R is also characterized by an X-ray powder diffraction reflections at about: 5.8, 11.8, 15.5, 16.2 and 18.6 degrees two theta±0.2 degrees two theta.

Form R is also characterized by X-ray powder diffraction reflections at about: 5.8, 16.2, 18.6, 23.2 and 27.0 degrees two theta±0.2 degrees two theta.

Form R is also characterized by X-ray powder diffraction reflections at about: 5.8, 16.2, 16.8, 19.9 and 25.4 degrees two theta±0.2 degrees two theta.

Figure 30:
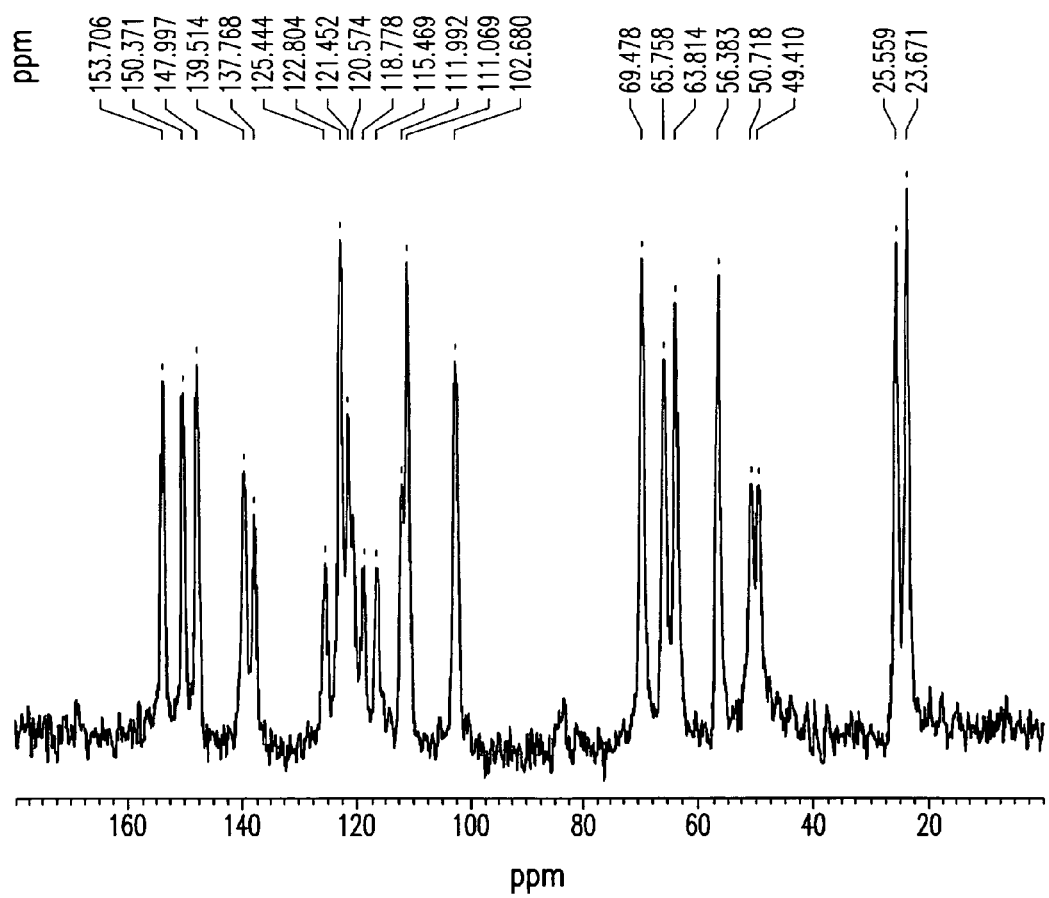
FIG. 30 illustrate a solid-state $^{13}$C-NMR spectrum of carvedilol dihydrogen phosphate Form R.
Figure 30A:
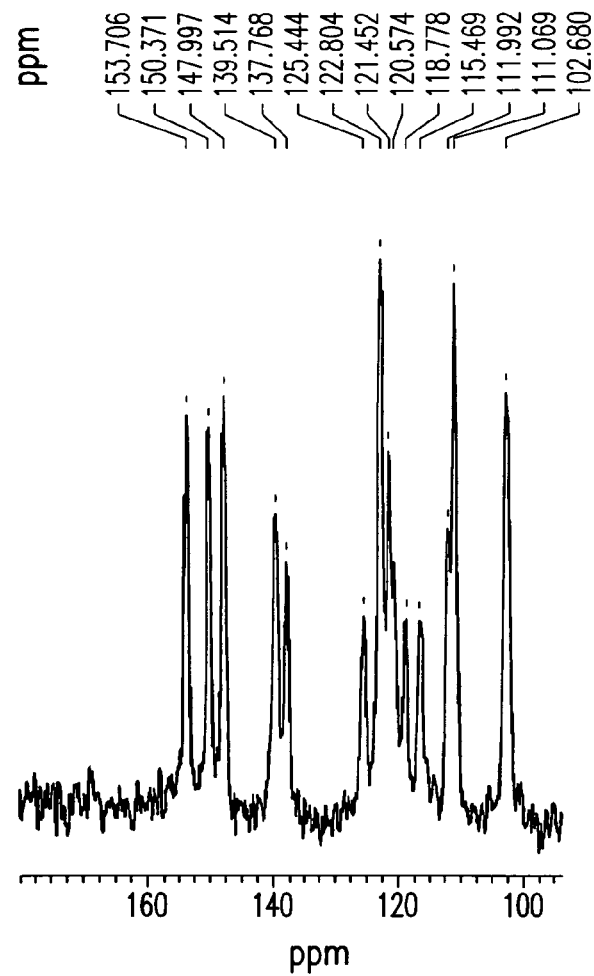
FIG. 30a illustrate a solid-state $^{13}$C-NMR spectrum of carvedilol dihydrogen phosphate Form R in the chemical shift area of 100 to 180 ppm.

Form R can be further characterized by X-ray powder diffraction reflections at about 8.5, 23.5, 24.7 and 27.0 degrees two-theta, ±0.2 degrees two-theta; a solid-state $^{13}$C-NMR spectrum having chemical shift resonances at about 137.8 and 116.5±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 35.1 and 13.8±0.1 ppm. The lowest ppm resonance in the chemical shift area of 100 to 180 ppm is typically at about 102.7±1 ppm. A typical powder x-ray diffractogram for Form R is shown in FIG. 29. A typical solid-state $^{13}$C-NMR spectrum of Form R is shown in FIG. 30 and or 30a.

Form R has a weight loss, as measured by GC measurement of residual solvents between about 75,000-100,300 ppm of isopropanol. Hence, Form R is isopropanol solvate of carvedilol dihydrogen phosphate.

Form R can be prepared by combining carvedilol base, isopropyl alcohol, and phosphoric acid to obtain a reaction mixture, followed by precipitation and recovery of Form R. Carvedilol base and phosphoric acid may be present in a molar ratio of about 0.8:1 to about 1.2:1, preferably 1:1. The reaction mixture can be heated or left at room temperature. Heating can be carried out of about 40° C. to about 60° C., such as about 55° C. The reaction mixture can be cooled to accelerate the precipitation process. Cooling can be carried at about 0° C. to about 20° C.

The product can be recovered by conventional techniques such as filtration. The crystals can be dried at elevated temperature, and a pressure of less than about 1 atmosphere.

Form R can also be prepared by slurrying carvedilol dihydrogen phosphate, such as amorphous, Form F1, Form N, in isopropanol. The slurry can be maintained to obtain Form R, such as a bout of about 6 hours to about 3 days. The product can be recovered and dried as above.

The present invention also provides crystalline form of Carvedilol phosphate salt, referred to herein as Form W. The X-ray powder diffraction pattern of Carvedilol phosphate salt Form W is substantially depicted in FIG. 32. Form W may be identified by characteristic X-Ray diffraction peaks at 6.6, 9.7, 13.8, 15.7 and 17.1±0.2.

Form W can be prepared from Carvedilol dihydrogen phosphate form F1, by adding Form F1 to $KH_2PO_4$, followed by adjution with a base, such as an alkali or alkaline metal base, including sodium and potassium hydroxide to obtain a suspension. A suspension is obtained when the pH reaches about 7. The suspension can be stirred at room temperature for a sufficient time, such as about 12 hours to about 2 days. Form W can be recovered by conventional techniques.

In another embodiment, the invention encompasses a crystalline form of carvedilol dihydrogen phosphate, referred to herein as Form Y, characterized by X-ray powder diffraction reflections at about: 7.7, 7.9, 9.1, 16.6 and 19.5 degrees two theta±0.2 degrees two theta; X-ray powder diffraction reflections at about: 7.7, 8.5, 16.6, 19.5 and 20.3 degrees two theta±0.2 degrees two theta. Form Y can be further characterized by X-ray powder diffraction reflections at about 8.5 and 15.5 degrees two-theta, ±0.2 degrees two-theta. A typical powder x-ray diffractogram for Form Y is shown in FIG. 31.

In another embodiment, the invention encompasses a process for preparing carvedilol dihydrogen phosphate Form Y comprising precipitation from a slurry of carvedilol, phosphoric acid and ethanol, wherein the slurry is maintained for about 2 to 3 hours.

The carvedilol and phosphoric acid are preferably present in a molar ratio of about 1:1.

Preferably, absolute ethanol is used.

Preferably, the ingredients are heated to reflux. Whether the ingredients are heated, the process may further comprise cooling, to induce precipitation.

The carvedilol dihydrogen phosphate may be recovered by any method known to the skilled artisan. Preferably, the carvedilol dihydrogen phosphate is recovered from the mixture by filtration.

Each of Forms L, L1, N, P, O, F, F1, F2, R, Y and W contain less than comprises less than about 20% crystalline carvedilol phosphate salts by weight, more preferably less than about 10% by weight, and even more preferably less than about 5% by weight, and even more preferably less than 1% by weight. The presence of a particular crystalline carvedilol can be determined by the presence of PXRD peaks characteristic of crystalline carvedilol phosphate salts.

In certain embodiments, each of Form L, L1, N, P, O, F, F1, F2, R, Y and W contains less than about 20%, less than about 10%, less than about 5% or less than about 1% by weight of Form I of carvedilol dihydrogen phosphate. In certain embodiments, each of Form L, L1, N, P, O, F, F1, F2, R, Y and W is provided as a solid material in which Form L, L1, N, P, O, F, F1, F2, R, Y and W represents about 80%, about 90%, about 95%, or about 99% by weight of the solid material.

In another embodiment, the invention encompasses essentially amorphous form of carvedilol dihydrogen phosphate characterized by data selected from the group consisting of: a solid-state $^{13}$C-NMR spectrum having broad chemical shift resonances at about 154.6, 146.7 and 140.3±0.2 ppm; and a solid-state $^{13}$C-NMR spectrum having chemical shift differences between the lowest ppm resonance in the chemical shift area of 100 to 180 ppm and another in the chemical shift area of 100 to 180 ppm of about 54.2, 46.3 and 39.9±0.1 ppm; a solid-state $^{13}$C-NMR spectrum having broad chemical shift resonances at about 154.6, 146.7, 140.3 and 100.4±0.2 ppm; and a solid-state $^{13}$C-NMR spectrum having chemical shift differences between the lowest ppm resonance in the chemical shift area of 100 to 180 ppm and another in the chemical shift area of 100 to 180 ppm of about 54.2, 46.3, 39.9 and 0.0±0.1 ppm. The lowest ppm resonance in the chemical shift area of 100 to 180 ppm is typically at about 100.4±1 ppm. X-ray diffractogram shown in FIG. 33, solid state $^{13}$C-NMR spectrum shown in FIG. 34 and or 34a.

Figure 33:
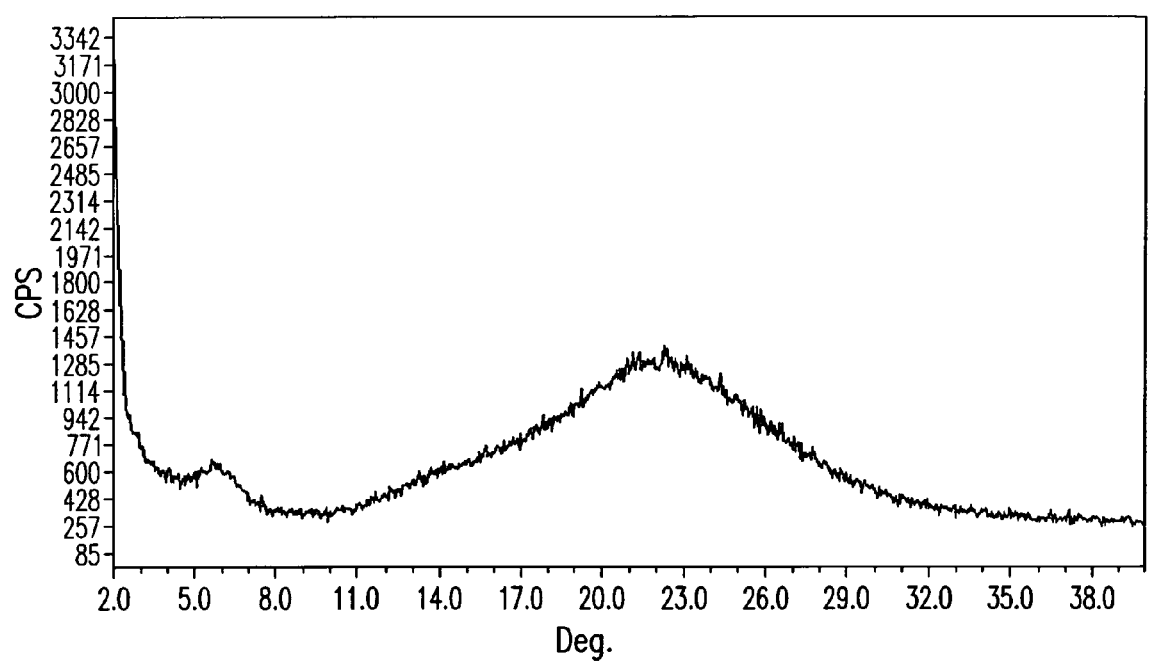
FIG. 33 illustrates a characteristic powder X-ray diffractogram for the amorphous form of carvedilol dihydrogen phosphate.

The essentially amorphous form of carvedilol dihydrogen phosphate can be further characterized by data selected from the group consisting of: a solid-state $^{13}$C-NMR spectrum having chemical shift resonances, which are broader than chemical shift resonances of a crystalline material, at about 121.9 and 111.5±0.2 ppm; and a solid-state $^{13}$C NMR spectrum having chemical shift differences between the lowest ppm resonance in the chemical shift area of 100 to 180 ppm and another in the chemical shift area of 100 to 180 ppm of about 21.5 and 11.1±0.1 ppm. The lowest ppm resonance in the chemical shift area of 100 to 180 ppm is typically at about 100.4±1 ppm. A typical powder x-ray diffractogram for the amorphous form is shown in FIG. 33. A typical solid-state $^{13}$C-NMR spectrum of amorphous form of carvedilol dihydrogen phosphate is shown in FIG. 34 and or 34a.

Figure 34:
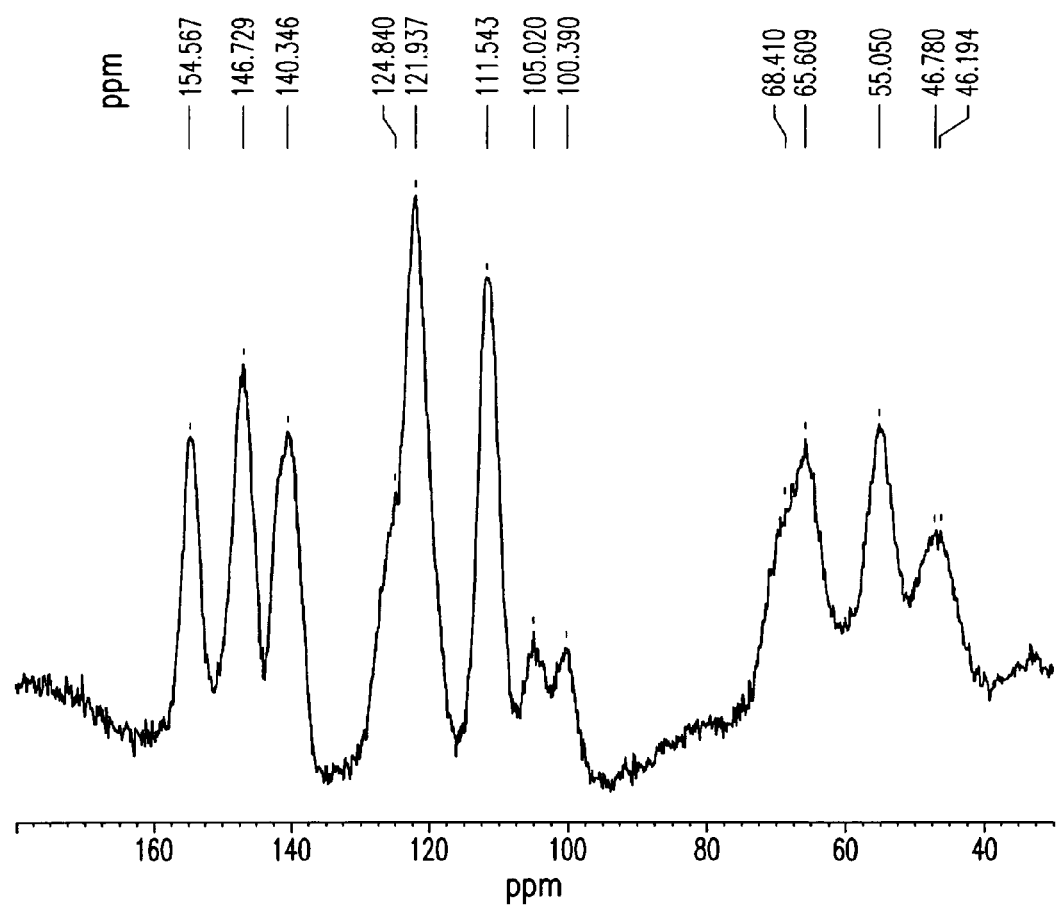
FIG. 34 illustrates a solid-state $^{13}$C-NMR spectrum of the amorphous form of carvedilol dihydrogen phosphate.
Figure 34A:
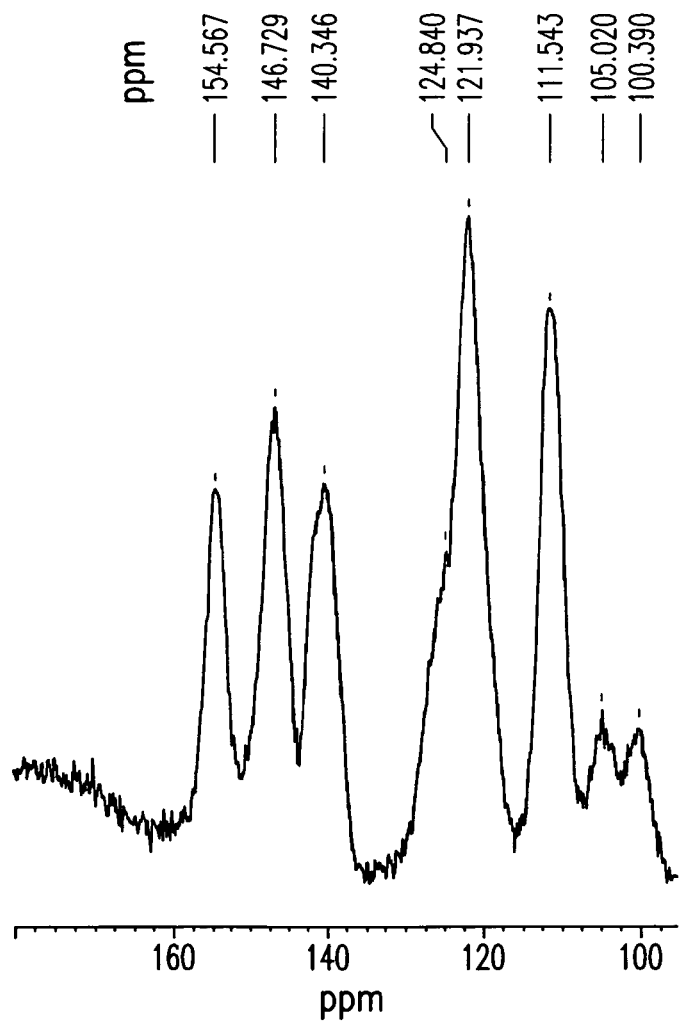
FIG. 34a illustrate a solid-state $^{13}$C-NMR spectrum of the amorphous form of carvedilol dihydrogen phosphate in the chemical shift area of 100 to 180 ppm.

The above amorphous form of carvedilol dihydrogen phosphate is substantially free of crystalline and is herein referred to as "carvedilol dihydrogen phosphate purely amorphous." FIG. 33 or 34 illustrates an XRPD pattern for this form, where the halo shape of the pattern illustrates the substantial absence of crystalline structure, by the absence of sharp peaks.

The carvedilol dihydrogen phosphate essentially amorphous contains not less than about 50% by weight of amorphous carvedilol dihydrogen phosphate, preferably not less than about 60%, more preferably not less than about 70%, even more preferably not less than about 80% and most preferably not less than about 90% or 95% by weight of amorphous carvedilol dihydrogen phosphate. In a certain embodiment, the carvedilol dihydrogen phosphate purely amorphous contains not more than about 20% by weight of Form I of carvedilol dihydrogen phosphate, preferably not more than about 10%, more preferably not more than about 5%, even more preferably not more than about 1% by weight of Form I of carvedilol dihydrogen phosphate.

The amount of crystallinity is quantified by methods known in the art like "crystallinity index" available to most XRD softwares.

Generally, the detection of peaks of Form I in amorphous carvedilol dihydrogen phosphate can be done by any method known to the skilled artisan.

For example, a person skilled in the art would know, when using XRD as a method for detecting or quantifying peaks of Form I in amorphous carvedilol dihydrogen phosphate, to select a peak or a number of peaks from the following list of peaks at about 7.0, 8.0, 9.2, 11.4, 16.0 and 20.7±0.2 degrees two theta. The absence or presence or intensity of a peak or a number of peaks from the following list of peaks at about 7.0, 8.0, 9.2, 11.4, 16.0 and 20.7±0.2 degrees two theta may be monitored at a scan rate slow enough, according to the common knowledge of the skilled in the art. The scan rate used may vary from instrument to instrument, and sample preparation. A skilled artisan will know to use other accepted analytical methods such as solid-state NMR, Raman, IR to detect Form I in amorphous carvedilol dihydrogen phosphate.

The carvedilol dihydrogen phosphate purely amorphous of the present invention is a solid material in which the carvedilol dihydrogen phosphate purely amorphous represents about 80% by weight of the solid material, more preferably about 90%, even more preferably about 95% and most preferably 99% by weight of the solid material, wherein the detection of crystalline percentage and/or amorphous percentage material can be calculated according to the common knowledge of the skilled in the art, for example by XRPD, in which the detection of crystalline percentage and/or amorphous percentage material is calculated by the ratio of the integrated area under the crystalline peaks to the total integrated area.

In another embodiment, the invention encompasses a process for preparing an amorphous form of carvedilol dihydrogen phosphate comprising dissolving carvedilol dihydrogen phosphate in a solvent selected from the group consisting of $C_1$-$C_8$ alcohols and mixtures of $C_{3-7}$ ketones with water, followed by solvent removal.

Preferably, a carvedilol dihydrogen phosphate purely amorphous is obtained.

Preferably, the solvent is methanol or acetone. Whenever acetone is used as the solvent, a ratio of acetone/water of 2:1 is preferably used and the solvent is preferably removed by spray drying.

Removing the solvent can be performed using vacuum drying or spray drying.

Vacuum drying broadly refers to processes involving removal of liquid material from a solution or mixture under air pressure below atmospheric pressure. The process of the present invention may preferably employ vacuum drying at a pressure of less than one atmosphere, such as less than about 100 mm Hg, more preferably less than about 40 mm Hg.

Alternatively, the solution may be spray dried.

The processes of the present invention may preferably employ spray drying with an inlet temperature of above about 80° C., preferably from about 80° C. to about 160° C.

The spray drying may preferably be conducted with an outlet temperature of below the inlet temperature, preferably from about 30° C. to about 110° C., more preferably below about 40° C.

The drying gas used in the process of the present invention may be any suitable gas, although inert gases such as nitrogen, nitrogen-enriched air, and argon are preferred.

The carvedilol dihydrogen phosphate product produced by spray drying may be recovered by techniques commonly used in the art, such as using a cyclone or a filter.

The carvedilol hydrogen phosphate starting material used for the processes of the present invention may be any crystalline or amorphous form of carvedilol hydrogen phosphate, including any solvates and hydrates. With processes where carvedilol hydrogen phosphate goes into solution, the form of the starting material is of minimal relevance since any solid state structure is lost in solution.

Amorphous Carvedilol Dihydrogen phosphate can also be prepared by heating another crystalline form of Carvedilol Dihydrogen phosphate, Particularly, heating of crystalline forms Form N or R results in Amorphous Carvedilol Dihydrogen. Heating is carried out at a temperature of about 80° C. to about 110° C. preferably about 80° C. to about 100° C. Heating can be carried out until the amorphous form obtained, such as from about 10 minutes to about 1 hours, preferably about 30 minutes.

Amorphous Carvedilol Dihydrogen phosphate can also be prepared by heating another crystalline form of Carvedilol Dihydrogen phosphate, Particularly, heating of crystalline Form N results in Amorphous Carvedilol Dihydrogen. Heating is preferably carried out at a temperature of about 20° C. to about 150° C., preferably about 140° C. Heating can be carried out until the amorphous form obtained, such as from about 10 minutes to about 4 hours, preferably about 30 minutes. In another embodiment, the invention encompasses a process for preparing a mixture of carvedilol dihydrogen phosphate Form N and carvedilol dihydrogen phosphate Form I comprising dissolving carvedilol dihydrogen phosphate in a mixture of $C_{3-7}$ ketones with water, followed by vacuum drying.

Preferably, the solvent is acetone. Whenever acetone is used as the solvent, a ratio of acetone/water of 2:1 is preferably used.

The invention further encompasses pharmaceutical compositions comprising the crystalline carvedilol phosphate, carvedilol hydrogen phosphate and carvedilol dihydrogen phosphate of the invention and, optionally, amorphous carvedilol dihydrogen phosphate of the invention, and at least one pharmaceutically acceptable excipient.

Pharmaceutical compositions of the invention contain the carvedilol dihydrogen forms of the invention, optionally in mixture with other crystalline or amorphous forms of carvedilol and/or other active ingredients such as hydrochlorothiazide.

In certain embodiments, the pharmaceutical compositions of the invention comprise Form L1 Form N, Form P, Form F, Form F1, Form F2, Form R, Form Y, Form L, Form L1, Form G, Form H, Form K, Form Q, Form Y or Form W and less than about 50%, less than about 25%, less than about 10%, less than about 5%, or less than about 1% (by weight of Form I of carvedilol dihydrogen phosphate present).

In certain embodiments, the pharmaceutical compositions of the invention comprise amorphous carvedilol phosphate and less than about 50%, less than about 25%, less than about 10%, less than about 5%, or less than about 1% (by weight of Form I of carvedilol dihydrogen phosphate present).

In certain embodiments, the pharmaceutical compositions of the invention comprise amorphous carvedilol hydrogen phosphate and less than about 50%, less than about 25%, less than about 10%, less than about 5%, or less than about 1% (by weight of Form I of carvedilol dihydrogen phosphate present).

In certain embodiments, the pharmaceutical compositions of the invention comprise amorphous carvedilol dihydrogen phosphate and less than about 50%, less than about 25%, less than about 10%, less than about 5%, or less than about 1% (by weight of Form I of carvedilol dihydrogen phosphate present).

In certain embodiments, the pharmaceutical compositions of the invention comprise a therapeutically effective amount of carvedilol phosphate, carvedilol hydrogen phosphate and carvedilol dihydrogen phosphate crystalline forms G, H, K, Q, L, L1, N, O, P, F, F1, F2, R, Y, W and amorphous forms (1:1, 2:1, 3:1) or mixtures thereof.

The purity of carvedilol phosphate, carvedilol hydrogen phosphate and carvedilol dihydrogen phosphate crystalline forms G, H, K, Q, L, L1, N, O, P, F, F1, F2, R, Y, W and amorphous form can be measured by any person skilled in the art, by PXRD using at least one peak of Form I when measuring the content of Form I. The peak or peaks may be selected from the following list of peaks at about: 7.0, 8.0, 9.2, 11.4, 14.0, 14.8, 15.5, 16.0, 18.3, 18.9, 19.7, 22.3, 22.9 and 25.4±0.2 degrees two theta.

Alternatively, the purity of the above crystalline forms can be measured by solid-state $^{13}$C NMR using at list one signal of Form I when measuring the content of Form I. The signal or signals may be selected from the following list of signals at about: 154.5, 146.5, 141.1, 139.7, 125.3, 122.1, 120.7, 118.3, 113.6, 110.2, 109.4 and 103.8±0.2 ppm.

In another embodiment, the present invention provides a pharmaceutical composition comprising by at least about 95% by weight at least one of the following crystal forms: crystalline Form G of carvedilol hydrogen phosphate, crystalline Form H of carvedilol hydrogen phosphate, crystalline Form K of carvedilol hydrogen phosphate, crystalline Form Q of carvedilol hydrogen phosphate crystalline Form L of carvedilol dihydrogen phosphate, crystalline Form L1 of carvedilol dihydrogen phosphate, crystalline Form N of carvedilol dihydrogen phosphate, crystalline Form O of carvedilol dihydrogen phosphate, crystalline Form P of carvedilol dihydrogen phosphate, crystalline Form F of carvedilol dihydrogen phosphate, crystalline Form F1 of carvedilol dihydrogen phosphate, crystalline Form F2 of carvedilol dihydrogen phosphate, crystalline Form R of carvedilol dihydrogen phosphate, crystalline Form Y of carvedilol dihydrogen phosphate,—and a pharmaceutically acceptable excipient, crystalline Form W of carvedilol dihydrogen phosphate.

In another embodiment, the present invention provides a pharmaceutical composition comprising a therapeutically effective amount of crystalline Form G of carvedilol hydrogen phosphate, crystalline Form H of carvedilol hydrogen phosphate, crystalline Form K of carvedilol hydrogen phosphate, crystalline Form Q of carvedilol hydrogen phosphate crystalline Form L of carvedilol dihydrogen phosphate, crystalline Form L1 of carvedilol dihydrogen phosphate, crystalline Form N of carvedilol dihydrogen phosphate, crystalline Form O of carvedilol dihydrogen phosphate, crystalline Form P of carvedilol dihydrogen phosphate, crystalline Form F of carvedilol dihydrogen phosphate, crystalline Form F1 of carvedilol dihydrogen phosphate, crystalline Form F2 of carvedilol dihydrogen phosphate, crystalline Form R of carvedilol dihydrogen phosphate, crystalline Form Y of carvedilol dihydrogen phosphate,—and a pharmaceutically acceptable excipient, crystalline Form W of carvedilol dihydrogen phosphate, amorphous carvedilol phosphate and amorphous carvedilol dihydrogen phosphate, and a pharmaceutically acceptable excipient.

In another embodiment, the present invention provides a method of treatment of congestive heart failure or hypertension comprising administering the above pharmaceutical composition to a mammal in need thereof.

Another embodiment of the invention provides a process of preparing a pharmaceutical composition comprising combining any of the carvedilol dihydrogen phosphate, carvedilol hydrogen phosphate and carvedilol phosphate forms of the invention, or a solution prepared using the carvedilol dihydrogen phosphate forms of the invention, with at least one pharmaceutically acceptable excipient.

Pharmaceutical compositions of the invention can contain the amorphous forms and/or crystalline forms of carvedilol phosphate, carvedilol hydrogen phosphate, or carvedilol dihydrogen phosphate described herein, optionally in mixture with other active ingredients such as hydrochlorothiazide. In addition to the active ingredient(s), the pharmaceutical compositions of the present invention can contain one or more excipients. Excipients are added to the composition for a variety of purposes.

Diluents increase the bulk of a solid pharmaceutical composition and can make a pharmaceutical dosage form containing the composition easier for the patient and caregiver to handle. Diluents for solid compositions include, for example, microcrystalline cellulose (e.g. AVICEL®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. EUDRAGIT®), potassium chloride, powdered cellulose, sodium chloride, sorbitol and talc.

Solid pharmaceutical compositions that are compacted into a dosage form like a tablet can include excipients whose functions include helping to bind the active ingredient and other excipients together after compression. Binders for solid pharmaceutical compositions include at least one of acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. KLUCEL®), hydroxypropyl methyl cellulose (e.g. METHOCEL®), liquid glucose, magnesium aluminum silicate, maltodextrin, methylcellulose, polymethacrylates, povidone (e.g. KOLLIDON®, PLASDONE®), pregelatinized starch, sodium alginate, or starch.

The dissolution rate of a compacted solid pharmaceutical composition in the patient's stomach can be increased by the addition of a disintegrant to the composition. Disintegrants include, but are not limited to, alginic acid, carboxymethylcellulose calcium, carboxymethylcellulose sodium (e.g. AC-DI-SOL @PRIMELLOSE®), colloidal silicon dioxide, croscarmellose sodium, crospovidone (e.g. KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g. EXPLOTAB®) or starch.

Glidants can be added to improve the flow properties of non-compacted solid composition and improve the accuracy of dosing. Excipients that can function as glidants include colloidal silicon dioxide, magnesium trisilicate, powdered cellulose, starch, talc, and/or tribasic calcium phosphate.

When a dosage form such as a tablet is made by compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease release of the product form the dye. Lubricants include, but are not limited to, magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and/or zinc stearate.

Flavoring agents and flavor enhancers make the dosage form more palatable to the patient. Common flavoring agents and flavor enhancers for pharmaceutical products that can be included in the composition of the present invention include, but are not limited to, maltol, vanillin, ethyl vanillin, menthol, citric acid, fumaric acid, ethyl maltol, or tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, one or more of the carvedilol forms described above and any other solid excipients are dissolved or suspended in a liquid carrier such as water, vegetable oil, alcohol, polyethylene glycol, propylene glycol or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, or cetyl alcohol.

Liquid pharmaceutical compositions of the present invention can also contain a viscosity-enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch, tragacanth or xanthan gum.

Sweetening agents such as sorbitol, saccharin, sodium saccharin, sucrose, aspartame, fructose, mannitol and/or invert sugar can be added to improve the taste.

Preservatives and chelating agents such as alcohol, sodium benzoate, butylated hydroxy toluene, butylated hydroxyanisole and ethylenediamine tetraacetic acid can be added at levels safe for ingestion to improve storage stability.

A liquid composition according to the invention can also contain a buffer such as gluconic acid, lactic acid, citric acid or acetic acid, sodium gluconate, sodium lactate, sodium citrate or sodium acetate.

Selection of excipients and the amounts to use can be readily determined by the formulation scientist based upon experience and consideration of standard procedures and reference works in the field.

The solid compositions of the invention include powders, granulates, aggregates and compacted compositions.

The amorphous forms and/or crystalline forms of carvedilol phosphate, carvedilol hydrogen phosphate, or carvedilol dihydrogen phosphate of the invention can be administered for treatment of congestive heart failure and hypertension (by any means that delivers the active ingredients) to the site of the body where beta-blocking activity exerts a therapeutic effect on the patient. For example, administration can be oral, buccal, parenteral (including subcutaneous, intramuscular, and intravenous) rectal, inhalant or ophthalmic. Although the most suitable route in any given case will depend on the nature and severity of the condition being treated, the most preferred route of the invention is oral. Amorphous carvedilol phosphate of the invention can be conveniently administered to a patient in oral unit dosage form and prepared by any of the methods well-known in the pharmaceutical arts. Dosage forms include solid dosage forms like tablets, powders, capsules, sachets, troches, or lozenges as well as liquid syrups, suspensions, or elixirs.

The active ingredient(s) and excipients can be formulated into compositions and dosage forms according to methods known in the art.

A composition for tableting or capsule filling can be prepared by wet granulation. In wet granulation some or all of the active ingredients and excipients in powder form are blended and then further mixed in the presence of a liquid, typically water that causes the powders to clump up into granules. The granulate is screened and/or milled, dried and then screened and/or milled to the desired particle size. The granulate can then be tableted or other excipients can be added prior to tableting such as a glidant and or lubricant.

A tableting composition can be prepared conventionally by dry blending. For instance, the blended composition of the actives and excipients can be compacted into a slug or a sheet and then comminuted into compacted granules. The compacted granules can be compressed subsequently into a tablet.

As an alternative to dry granulation, a blended composition can be compressed directly into a compacted dosage form using direct compression techniques. Direct compression produces a more uniform tablet without granules. Excipients that are particularly well suited to direct compression tableting include microcrystalline cellulose, spray dried lactose, dicalcium phosphate dihydrate and/or colloidal silica. The proper use of these and other excipients in direct compression tableting is known to those in the art with experience and skill in particular formulation challenges of direct compression tableting.

A capsule filling of the invention can comprise any of the aforementioned blends and granulates that were described with reference to tableting, only they are not subjected to a final tableting step.

Yet more particularly, a tablet can, for example, be formulated by blending and directly compressing the composition in a tablet machine.

A capsule can, for example, be prepared by filling half of a gelatin capsule with the above tablet composition and capping it with the other half of the gelatin capsule.

A simple parenteral solution for injection can, for example, be prepared by combining amorphous carvedilol phosphate of the invention, sterile propylene glycol, and sterile water and sealing the composition in a sterile vial under sterile conditions.

Capsules, tablets and lozenges and other unit dosage forms preferably contain a dosage level of about 1 mg to about 100 mg of amorphous forms and/or crystalline forms of carvedilol phosphate, carvedilol hydrogen phosphate, or carvedilol dihydrogen phosphate described herein.

Another embodiment of the present invention provides a method for treating a patient suffering from hypertension, congestive heart failure, or another condition that would benefit from treatment with amorphous forms and/or crystalline forms of carvedilol phosphate, carvedilol hydrogen phosphate, or carvedilol dihydrogen phosphate, comprising the step of administering to the patient a pharmaceutical composition comprising a therapeutically effective amount of the amorphous forms and/or crystalline forms of carvedilol phosphate, carvedilol hydrogen phosphate, or carvedilol dihydrogen phosphate of the invention described herein.

The amorphous form (1:1) of the present invention has higher solubility with compared to Form I at pH=7 and 25° C.:

| Form | Solubility (µg/mL) |
| --- | --- |
| I ('027) | 9.6 |
| Amorphous | 14.9 |

Figure 36:
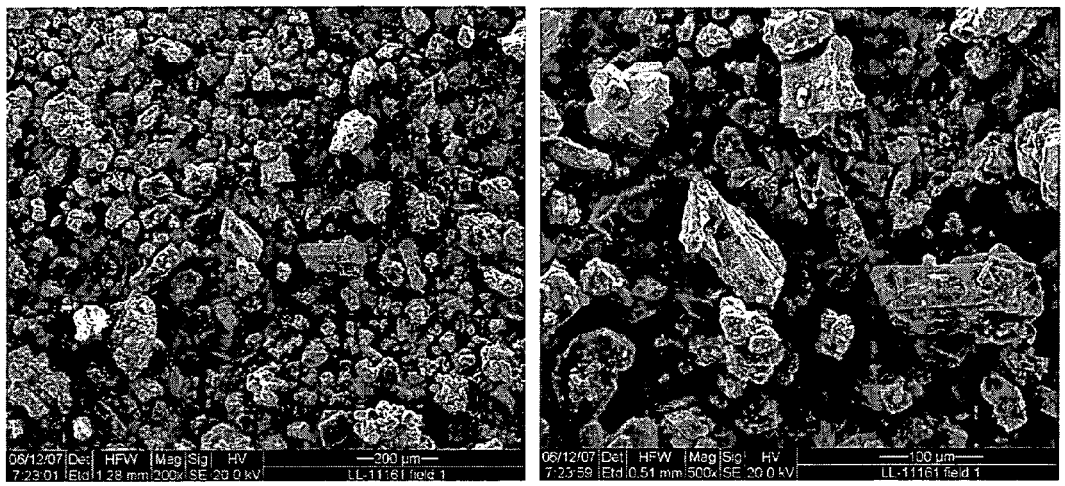
FIG. 36 is an SEM image of the Form I.
Figure 37:
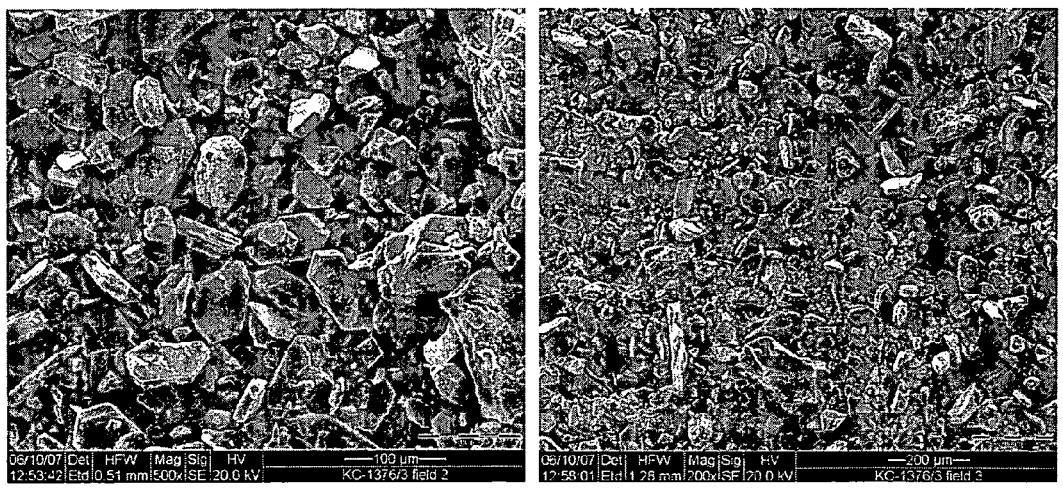
FIG. 37 is an SEM images of the Form IV.
Figure 38:
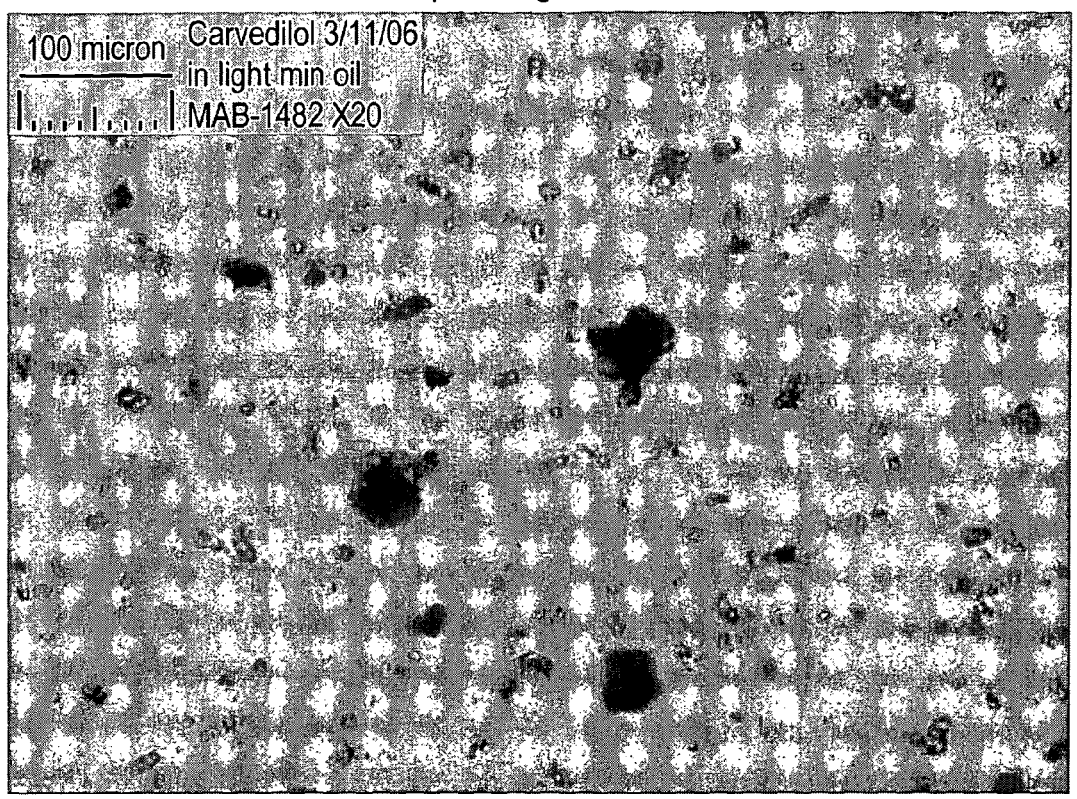
FIG. 38 is a Microscope image of the Form I.
Figure 39:
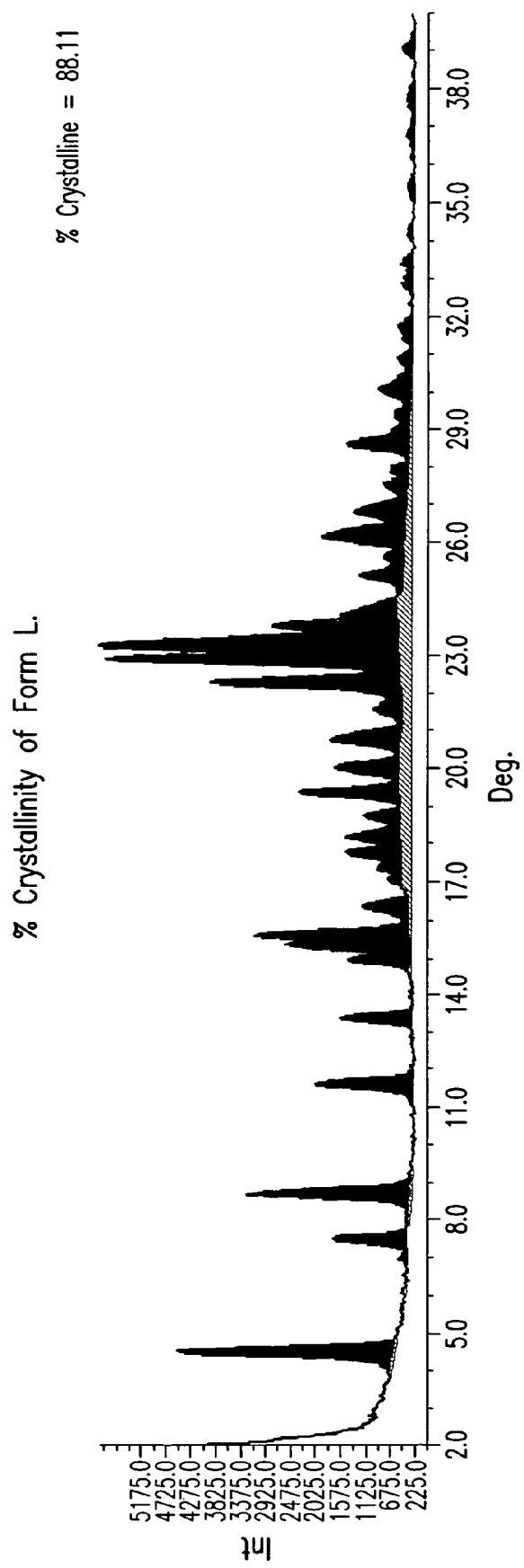
FIG. 39 illustrates the % Crystallinity of Form L.
Figure 40:
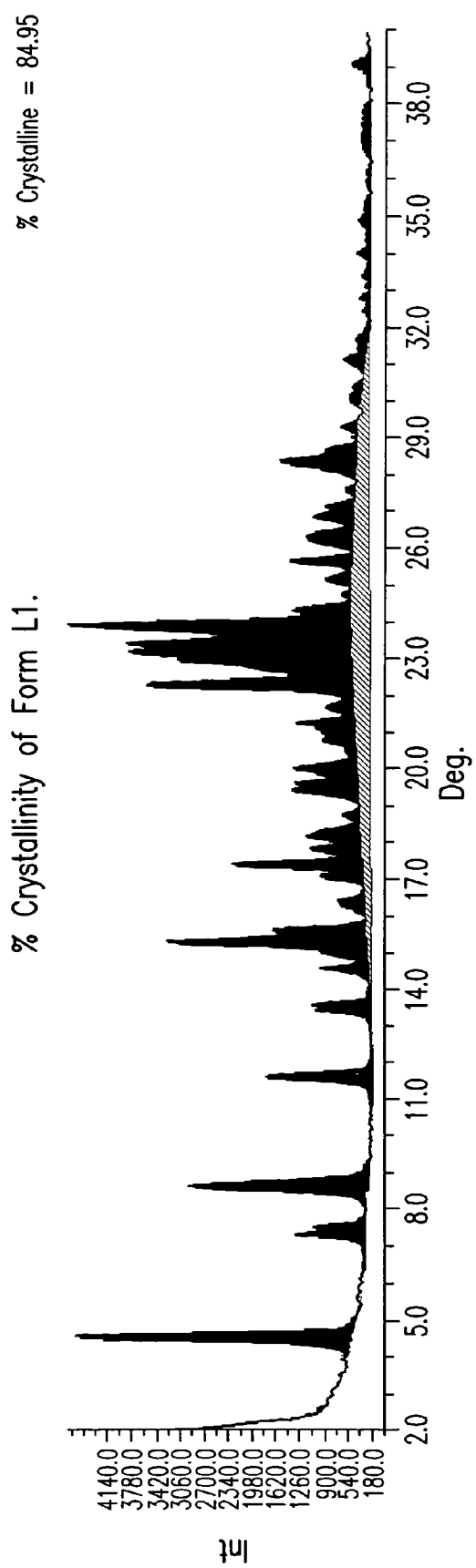
FIG. 40 illustrates the % Crystallinity of Form L1.
Figure 41:
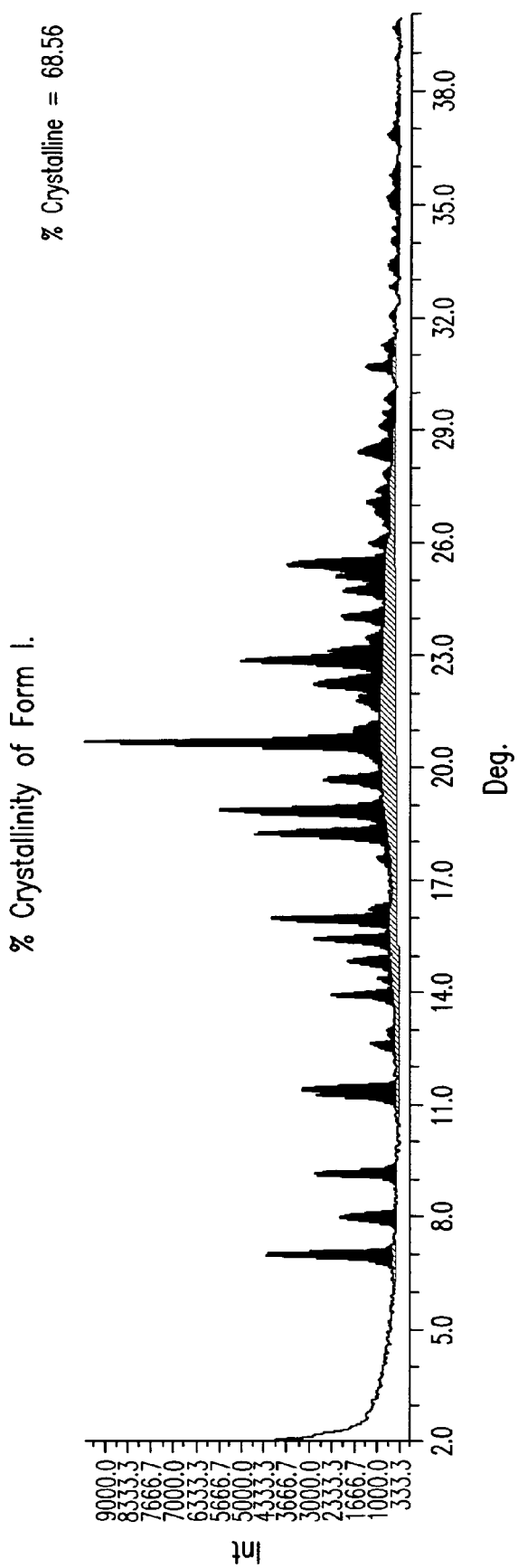
FIG. 41 illustrates the % Crystallinity of Form I.
Figure 42:
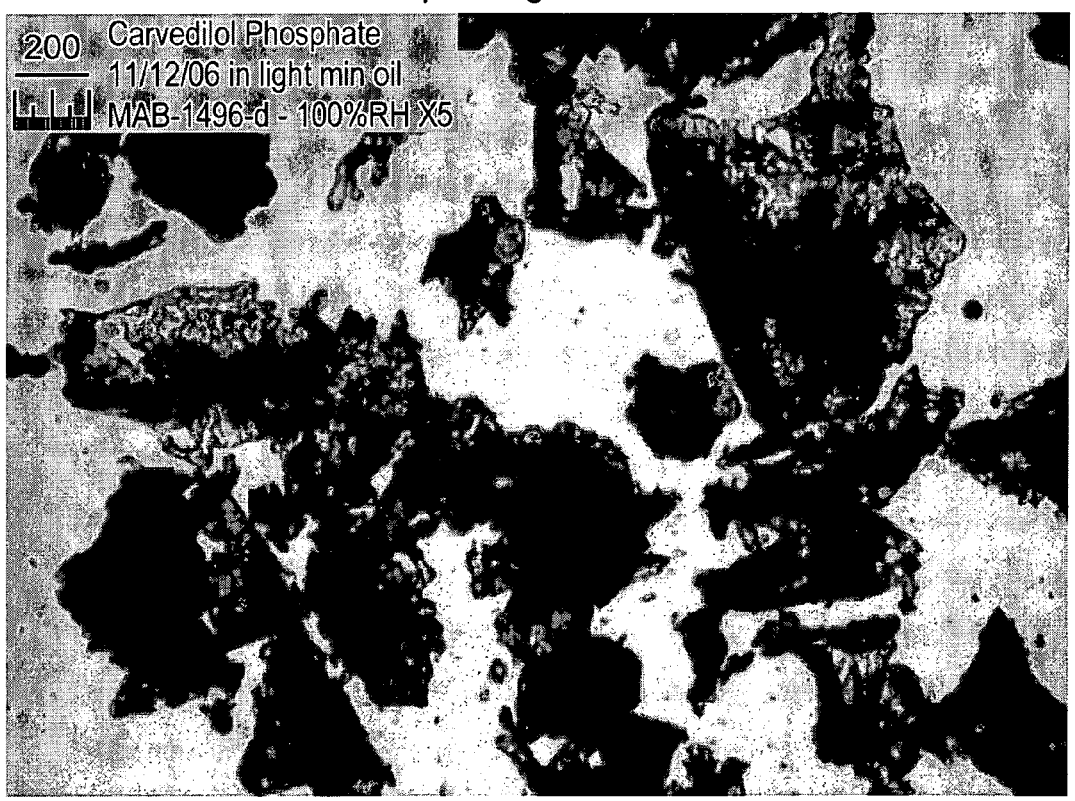
FIG. 42 is a Microscope image of the Form N.
Figure 43:
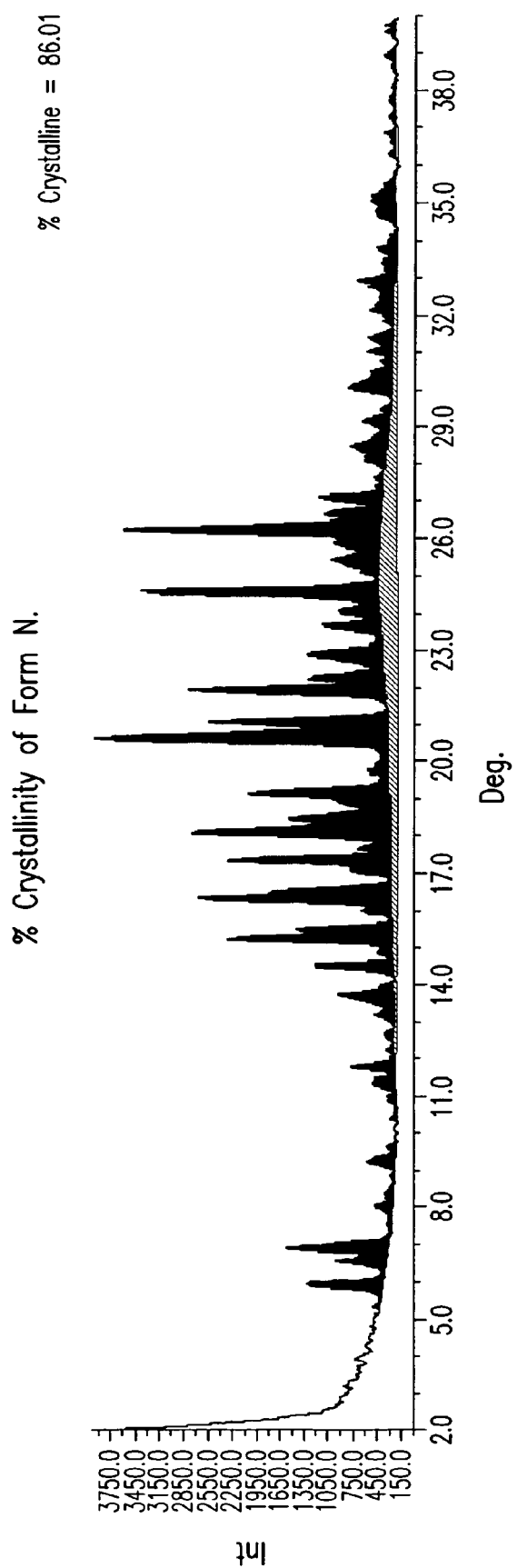
FIG. 43 illustrates the % Crystallinity of Form N.
Figure 52:
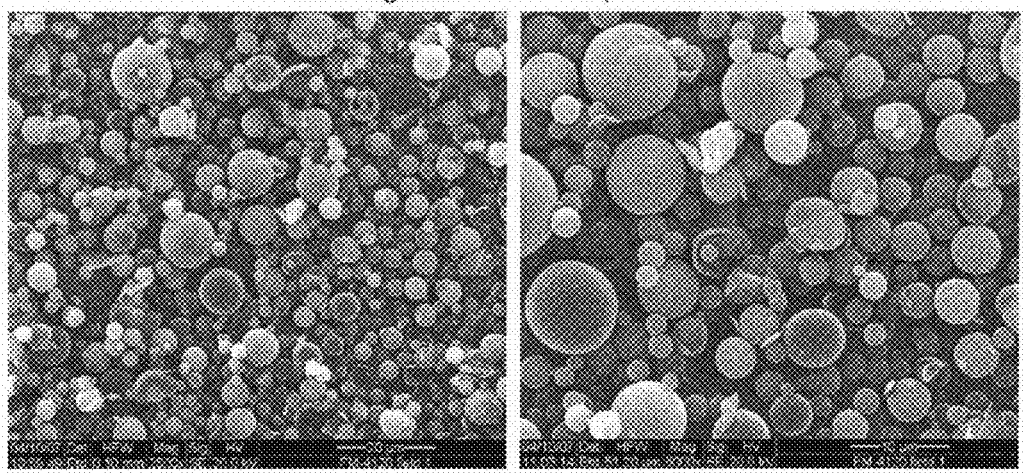
FIG. 52 is an SEM images of amorphous form 1:1.
Figure 53:
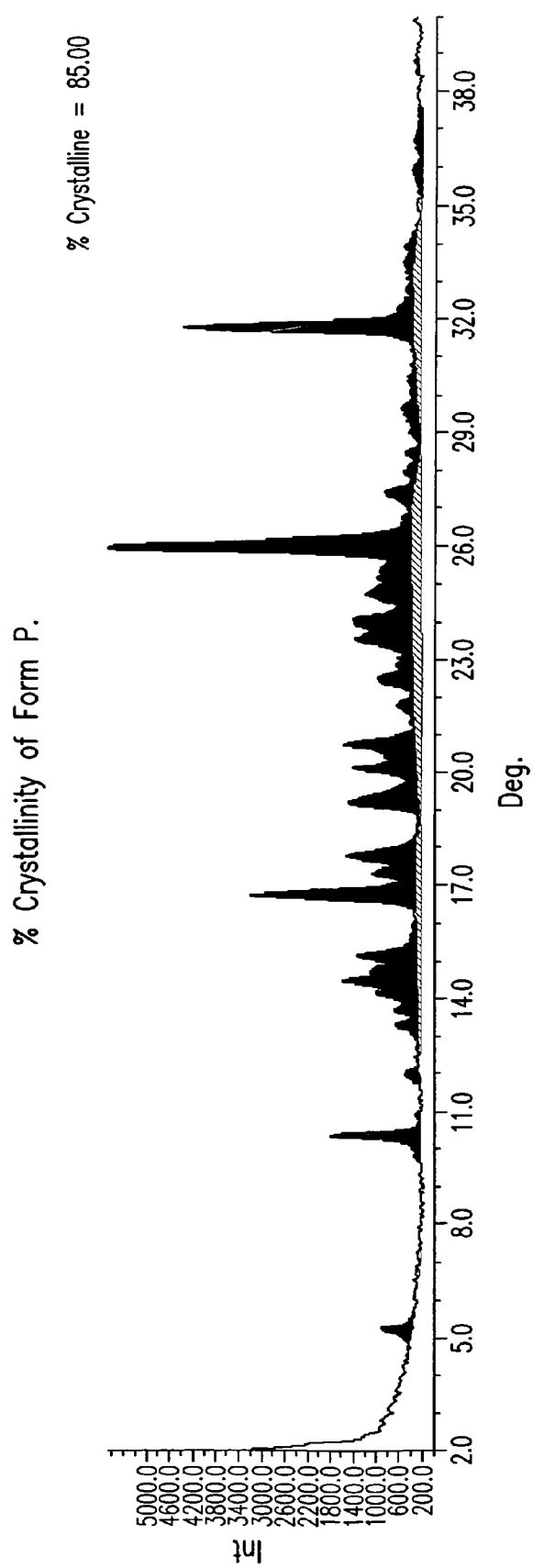
FIG. 53 is the % crystallinity of Form P.

Such higher solubility contributes to better bioavailability and can lead to greater efficacy. Furthermore, the amorphous form has very homogenous spherical habit (FIG. 52) directly obtained from manufacture process with compared to Form I (FIG. 36) or Form IV (FIG. 37). Pharmaceutical particles are rarely spherical. Such spherical habit has many advantages such as: higher compressibility. The compressibility and homogeneity of the powder also affect the uniformity of the solid dosage form (poor content uniformity would result if a drug powder were not dispersed evenly throughout a mixture with excipients) and its size.

Using spherical powders, flowability of the powder may be improved. Processing of powders strongly depends on powder flowability. Powder flowability is defined as the time required for a specific quantity of powder to flow through an orifice or a die cavity. Flowability of a powder is important in high-volume manufacturing, which depends on rapid, uniform, consistent filling of die cavity. Poor flow characteristics cause slow and nonuniform press feeding and difficulty in ensuring a fill of the die cavity. Free-flowing powder refers to powders that readily flow in the die cavity [ASM Handbook, vol. 7: Powder Metallurgy].

Forms F, F1, L, L1, N, P and R of the present invention have more crystallinity than Form I (about 86% for Form R, about 87% for Form F, about 86% for F1, about 88% for L and about 85% for L1 compared to about 68% of I, about 86% for Form N, about 85% for Form P) as can be seen from the % crystallinity calculation preformed using the WinXRD 2.0 program (FIGS. 46, 48, 39, 40, 43, 53, 50, 41). Less crystallinity powder means that the % of the amorphous ratio of the powder is greater, which can mean less stable material (amorphous materials are chemically and physically less stable than crystalline materials, such as when exposed to pressure, grinding, heat, long term shelf-life, humidity, etc.)

Forms F, F1, L, L1 and R are more stable for formulation than Form IV. Under extreme heat conditions (80° C. for 30 min in oven) which may be used during formulation processes, Forms F, F1, L, L1 and R are stable upon heating when compared to Form IV (it transforms to amorphous form under these conditions).

Forms F, F1, N and Y of the present invention have bigger particle size dimensions (Form N has particle size dimensions ~200-400 μm) (Form Y has bigger particle size dimensions ~20-100 μm), (Form F1 has particle size dimensions ~50-150 μm) (Form F has bigger particle size dimensions ~50-200 μm) compared to Form I (less than 20 μm), as can be seen from the microscope images of FIGS. 45, 47, 42, 51, 38. It has the advantage of being able to reduce the particle size to a range of smaller dimensions (according to the requirements of the formulator who prepare the capsule or tablet), while when starting in advance with a smaller size of powder (Form I) limits this option. In addition, small particles, reduce flowability.

Form P has higher melting point (about 158° C.) with compared to Form IV (about 90° C.) as was measured by DSC (Differential Scanning Calorimetry) measurement which is a thermal analysis technique to detect heat changes of a material as a function of temperature change.

Figure 44:
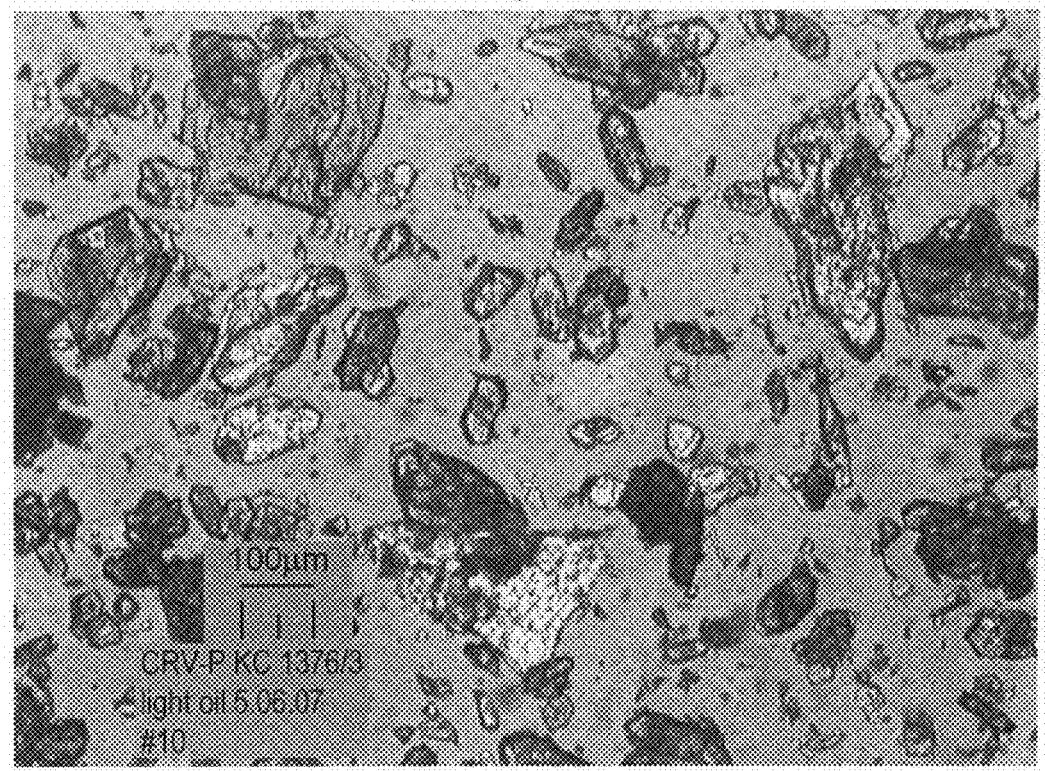
FIG. 44 is a Microscope image of the Form IV.
Figure 45:
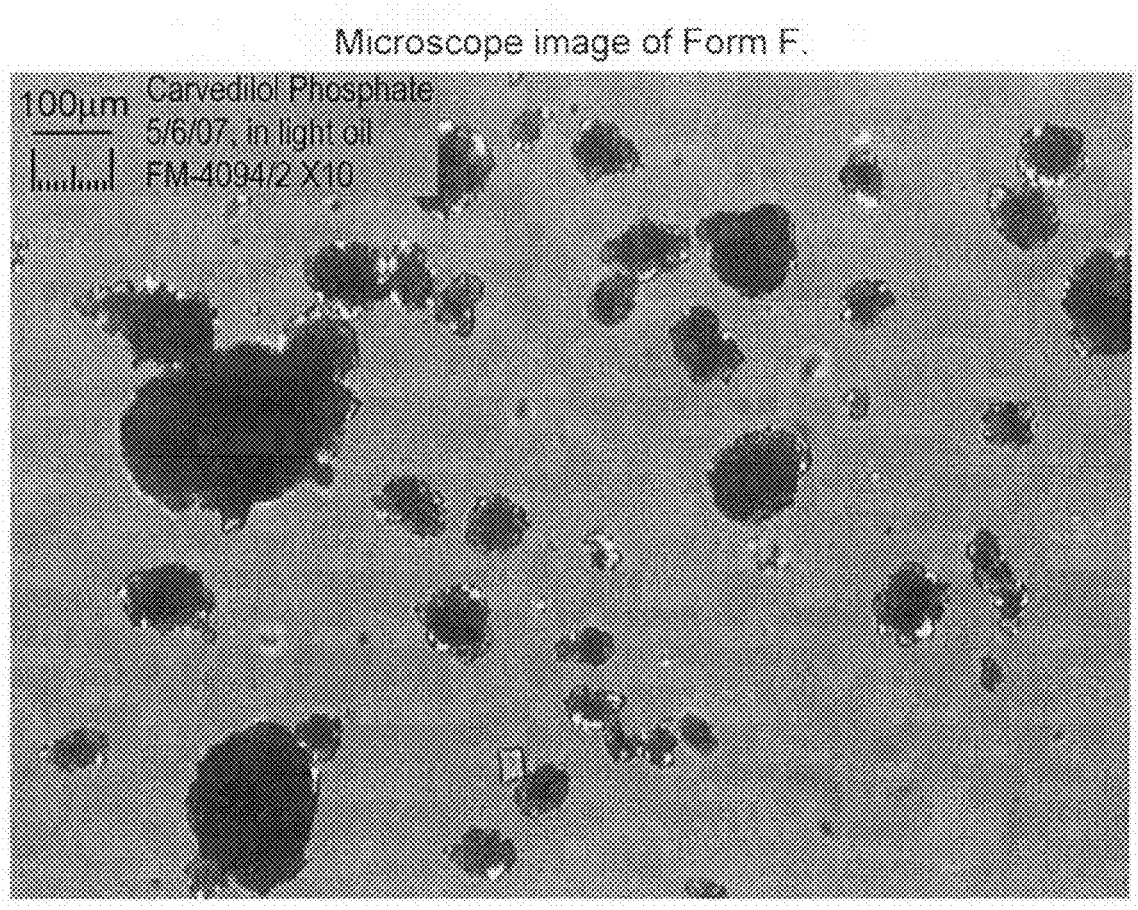
FIG. 45 is a Microscope image of Form F.
Figure 46:
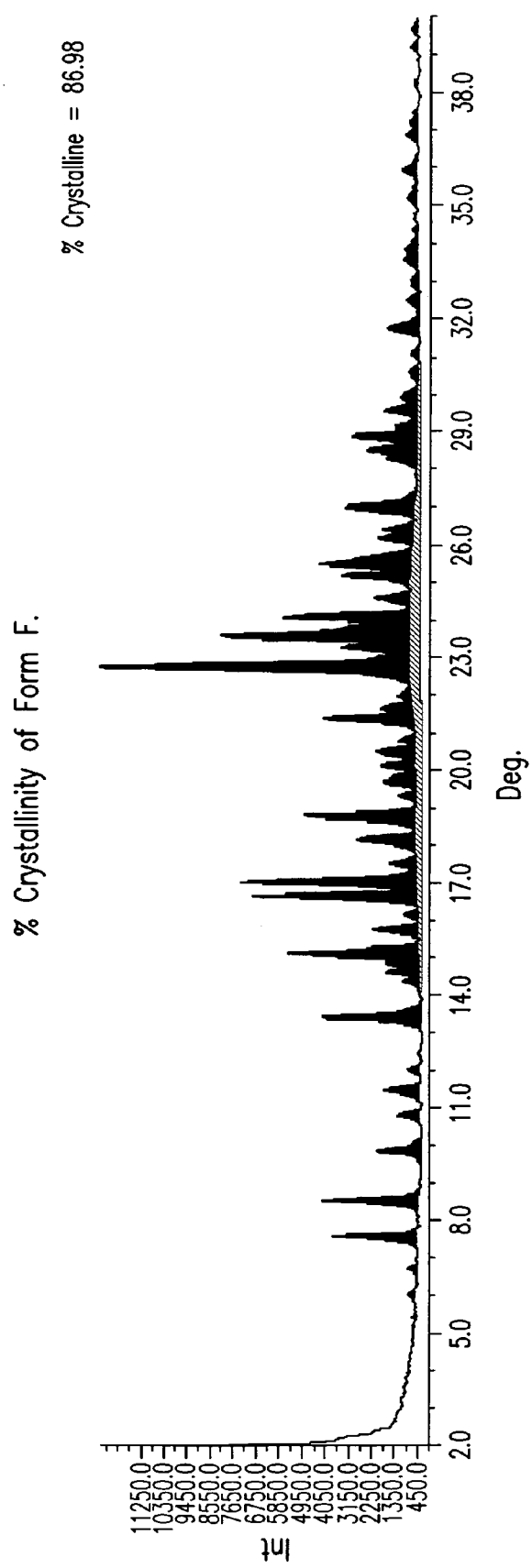
FIG. 46 illustrates the % Crystallinity of Form F.
Figure 47:
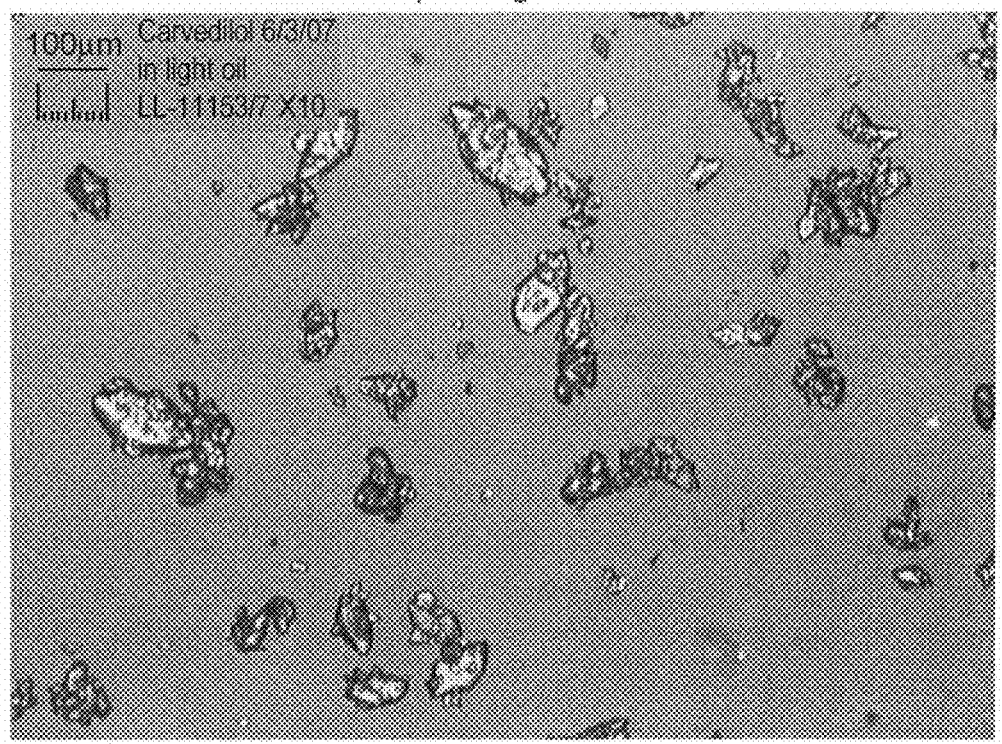
FIG. 47 is a Microscope image of Form F1.
Figure 48:
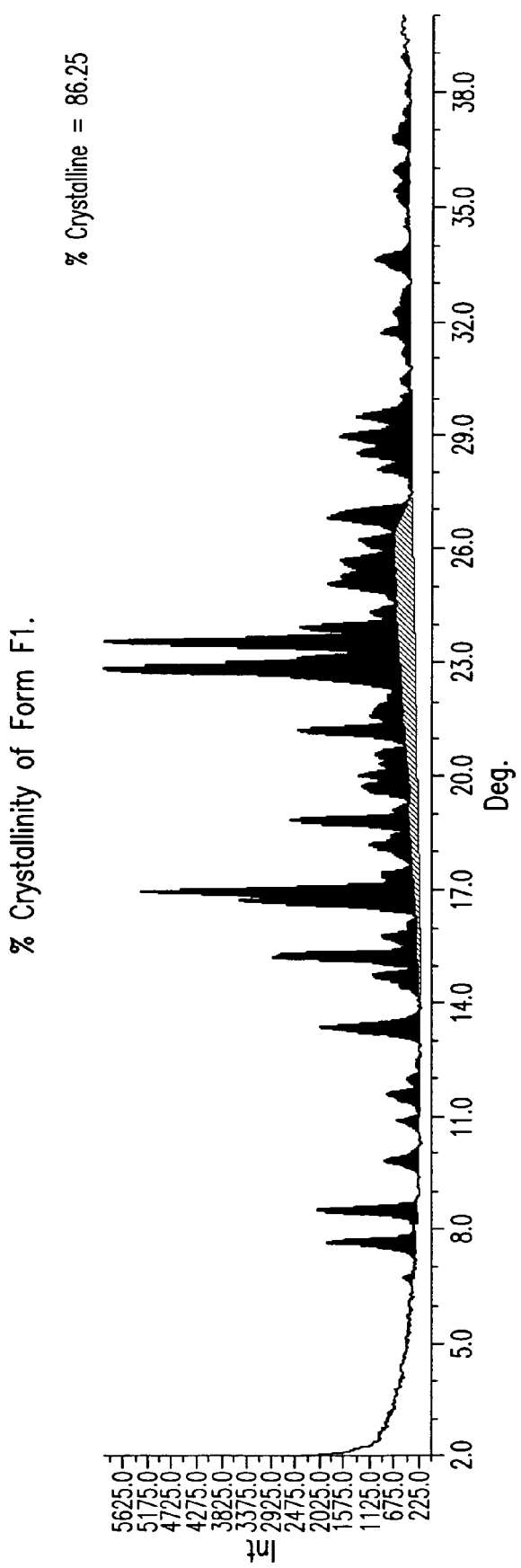
FIG. 48 illustrates the % Crystallinity of Form F1.
Figure 49:
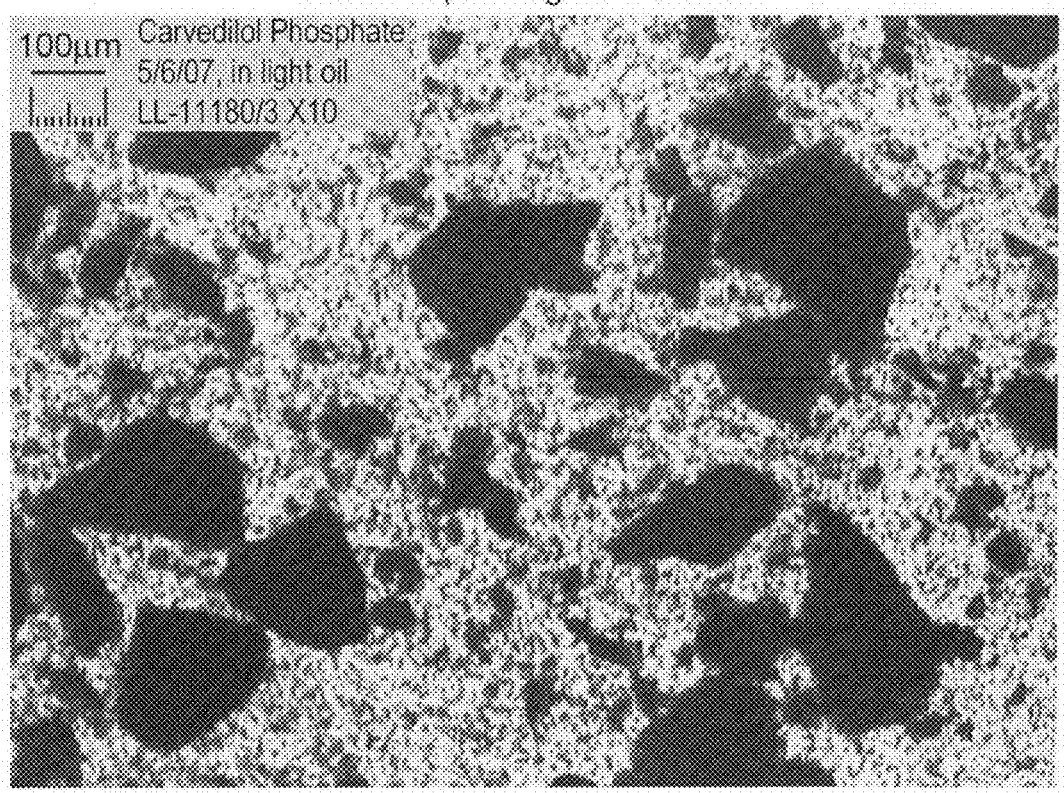
FIG. 49 is a Microscope image of Form R.
Figure 50:
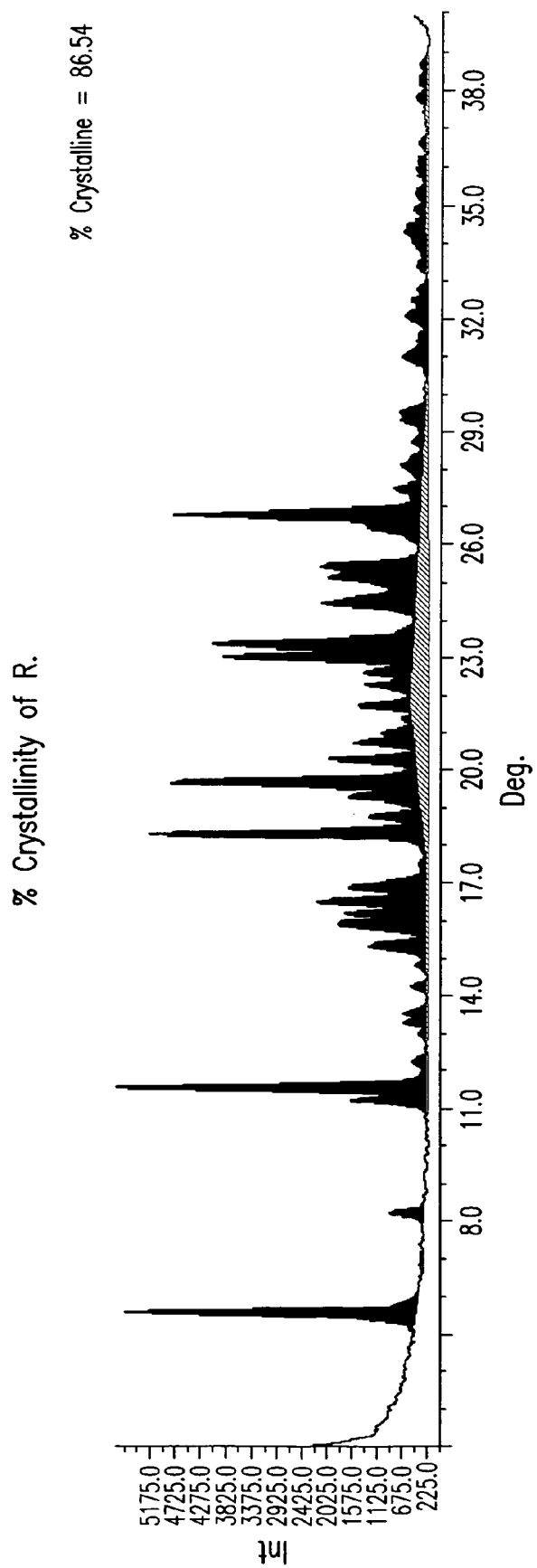
FIG. 50 illustrates the % crystallinity of R.
Figure 51:
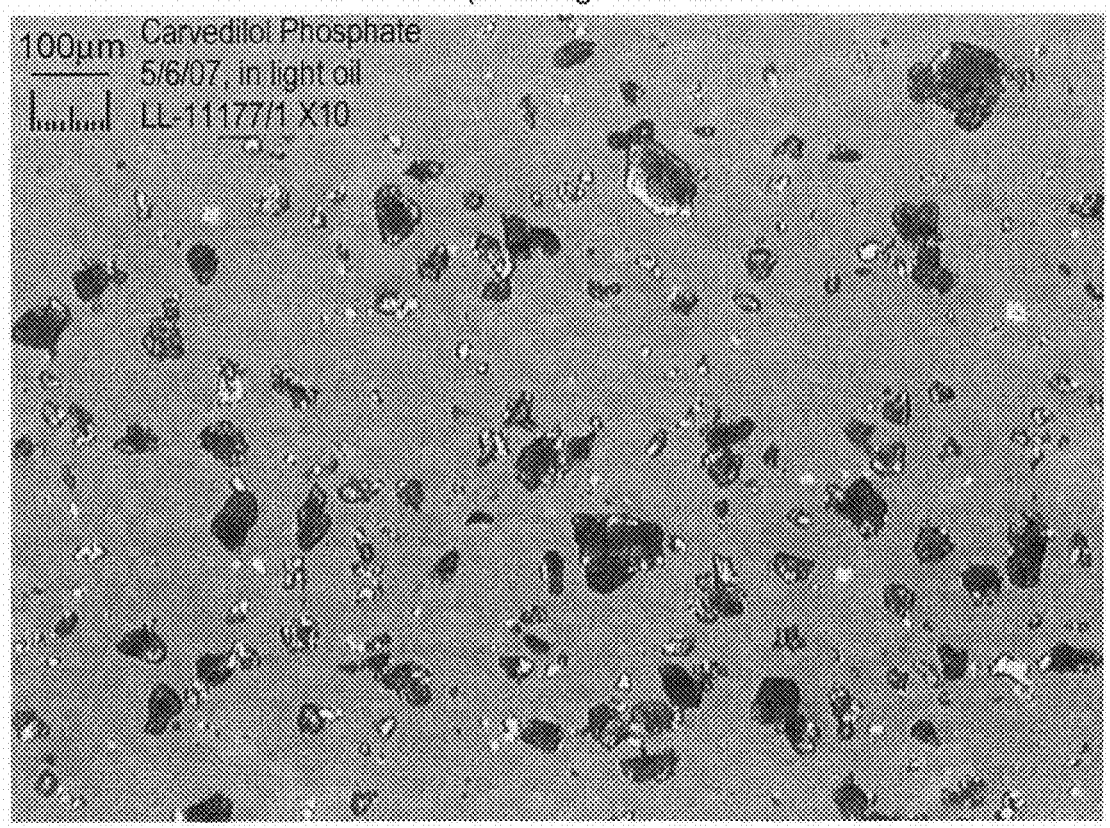
FIG. 51 is a Microscope image of Form Y.

Form Y has a more homogenous habit (FIG. 51) directly obtained from manufacture process when compared to that of Form IV (FIG. 44). This has many advantages such as: higher compressibility which is very important for handling the powder, storage, safety, etc. The compressibility and homogeneity of the powder also affect the uniformity of the solid dosage form (poor content uniformity would result if a drug powder were not dispersed evenly throughout a mixture with excipients) and its size.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

The following examples are given for the purpose of illustrating the invention and shall not be construed as limiting the scope or spirit of the invention.

EXAMPLES

Instruments

Powder X-Ray Diffraction

Powder X-ray diffraction data were obtained by using conventional methods employing a SCINTAG powder X-Ray diffractometer model X'TRA equipped with a solid-state detector. Copper radiation of 1.5418 Å was used to analyze the samples, which were in round aluminum sample holders with zero background. All peak positions reported are within ±0.2 degrees two theta.

TGA Analysis

TGA analysis was preformed using Mettler 3M with Mettler TG 50 thermobalance. The weight of the samples was about 10 mg; the samples were scanned at a rate of 10° C./min from 25° C. to 200 or 250° C. The oven was constantly purged with nitrogen gas at a flow rate of 40 ml/min. Standard alumina crucibles covered by lids with 1 hole were used.

Water Content

Water content was determined by Karl Fisher analysis using Mettler Toledo DL 38 Karl Fisher Titrator.

$^{13}$C NMR Spectroscopy

The cp/mas $^{13}$C NMR investigations were preformed at 125.76 MHz at ambient temperature on a Bruker DMX-500 digital FT-NMR spectrometer equipped with a BL-4 cp/mas probehead and High Resolution/High Performance (HPHP) 1H and X-channel preamplifiers for solids. Samples were placed in 4 mm zirconia rotors fitted with 'Kel-F' plastic caps, and spun with dry air at 5.0 kHz.

Example 1

Preparation of Amorphous Carvedilol Phosphate

To a mixture of 3 g of carvedilol in 45 ml ethanol was slowly added 0.14 ml of phosphoric acid. The mixture was heated to reflux until complete dissolution. The resulting solution was stirred for an additional 10 minutes, and cooled to room temperature. 45 ml of water were then added to the solution and it was stirred overnight, upon which a precipitate formed. The precipitate was filtered and dried in a vacuum oven to give 2.7 g of a white solid. The resulting solid was analyzed by PXRD and was determined to be amorphous carvedilol phosphate.

Example 2

Preparation of Carvedilol Hydrogen Phosphate Form G

To a mixture of 5 g of carvedilol in 50 ml methyl alcohol was slowly added 0.84 ml of phosphoric acid and the mixture heated to reflux to obtain a clear solution. After cooling to room temperature, 50 ml of water were added and the resulting solid was filtered and dried in a vacuum oven to give 2.85 g of a white solid. The resulting solid was analyzed by XRD and shown to be carvedilol hydrogen phosphate Form G.

Example 3

Preparation of Carvedilol Hydrogen Phosphate Form G

To a mixture of 3 g of carvedilol in 45 ml acetone/water (3:1) was slowly added 0.22 ml of phosphoric acid and the mixture was stirred overnight at room temperature. The resulting solid was filtered and analyzed by XRD and shown to be carvedilol hydrogen phosphate Form G.

Example 4

Preparation of Phosphate Salt of Carvedilol Hydrogen Phosphate Form G 10 g of dry amorphous carvedilol dihydrogen phosphate were charged into 1 liter glass reactor equipped with mechanical stirrer, and controlled heating/cooling system. 250 ml of 0.1M (buffer phosphoric pH=3.5) aqueous solution were charged into the reactor. The agitator was turned on, and suspension was obtained. The suspension was stirred at 25° C. for 19 hours and filtered.

The cake product was dried in a vacuum oven under a reduced pressure (under 100 mmHg) at 50° C. until a dried product was obtained.

The resulting solid was analyzed by XRD and showed phosphate salt of carvedilol hydrogen phosphate Form G.

Example 5

Preparation of Phosphate Salt of Carvedilol Hydrogen Phosphate Form G 10 g of dry amorphous carvedilol dihydrogen phosphate were charged into 1 liter glass reactor equipped with mechanical stirrer, and controlled heating/cooling system. 250 ml of 0.1M (buffer phosphoric pH=7) aqueous solution were charged into the reactor. The agitator was turned on, and suspension was obtained. The suspension was stirred at 25° C. for 21 hours and filtered.

The cake product was dried in a Vacuum oven under a reduced pressure (under 100 mmHg) at 50° C. until a dried product was obtained.

The resulting solid was analyzed by XRD and showed phosphate salt of carvedilol hydrogen phosphate Form G.

Example 6

Preparation of Carvedilol Hydrogen Phosphate Form G

A 50 ml flask is charged with 1 g of Carvedilol dihydrogen phosphate Form R and 10 ml water. The mixture is stirred at room temperature for 24 hours until the crystals are converted to Form G. The crystals are collected by filtration under reduced pressure and dried at 50° C. under reduced pressure (under 100 mmHg).

The resulting solid was analyzed by XRD and showed Carvedilol hydrogen phosphate Form G.

Example 7

Preparation of Carvedilol Hydrogen Phosphate Form G

A 50 ml flask is charged with 1 g of Carvedilol dihydrogen phosphate Form F1 and 10 ml water. The mixture is stirred at room temperature for 24 hours until the crystals are converted to Form G. The crystals are collected by filtration under reduced pressure and dried at 50° C. under reduced pressure (under 100 mmHg).

The resulting solid was analyzed by XRD and showed Carvedilol hydrogen phosphate Form G.

Example 8

Preparation of Carvedilol Hydrogen Phosphate Form H

To a mixture of 3 g of carvedilol in 45 ml ethyl alcohol was slowly added 0.22 ml of phosphoric acid and the mixture heated to reflux and 150 ml of ethyl alcohol followed by 30 ml of water were added. After cooling to room temperature, the mixture was stirred overnight. The resulting solid was filtered and dried in a vacuum oven to give 2.37 g of a white solid. The resulting solid was analyzed by XRD and shown to be carvedilol hydrogen phosphate Form H.

Example 9

Preparation of Carvedilol Hydrogen Phosphate Form K

Carvedilol hydrogen phosphate Form H was exposed to 80% and 100% relative humidity (RH) for 16 days at room temperature. According to XRD, the exposed samples contain carvedilol hydrogen phosphate Form K.

Example 10

Preparation of Carvedilol Hydrogen Phosphate Form K

A mixture of 10 g of carvedilol in 150 ml acetone/water (3:1) was stirred at room temperature for 30 minutes and 0.56 ml. of phosphoric acid 85% were added and stirred for overnight. The resulting mixture was filtered and dried in vacuum oven for over night at 50° C. The product was analyzed by XRD and found to be carvedilol hydrogen phosphate Form K.

Example 11

Preparation of a Mixture of Carvedilol Hydrogen Phosphate Forms K and H

A mixture of 10 g of carvedilol in 150 ml acetone/water (3:1) was stirred at room temperature for 30 minutes and filtrated (to remove foreign objects). To the filtrated solution was added 0.56 ml. of phosphoric acid 85% and stirred for overnight. The resulting mixture was filtered and dried in vacuum oven for over night at 50° C. The product was analyzed by XRD and found to be a mixture of carvedilol hydrogen phosphate Forms K and H.

Example 12

Preparation of carvedilol hydrogen phosphate Form Q

Carvedilol hydrogen phosphate Form K was exposed to 0% relative humidity (RH) for 7 days at room temperature. According to XRD, the exposed sample is carvedilol hydrogen phosphate Form Q.

Example 13

Preparation of Amorphous Carvedilol Hydrogen Phosphate 10 g of carvedilol hydrogen phosphate was dissolved in 200 ml of methanol at reflux. The solution was sprayed (72 [ml/h]) into the chamber with ambient nitrogen (38 m³/h, 100° C.) at co-current flow. The atomizing flow (660[l/h]) of nitrogen produced droplets, which led to a high evaporation rate. The temperature of the outlet solids was 29-30° C. The obtained sample was analyzed by XRD and found to be amorphous carvedilol hydrogen phosphate.

Example 14

Preparation of Amorphous Carvedilol Hydrogen Phosphate 10 g of carvedilol hydrogen phosphate was dissolved in 200 ml of acetone/water (2:1) at reflux. The solution was sprayed (72 [ml/h]) into the chamber with ambient nitrogen (38 m³/h, 100° C.) at co-current flow. The atomizing flow (660[l/h]) of nitrogen produced droplets, which led to a high evaporation rate. The temperature of the outlet solids was 40° C. The obtained sample was analyzed by XRD and found to be amorphous.

Example 15

Preparation of Carvedilol Dihydrogen Phosphate Form I

To a mixture of 5 g of Carvedilol in 100 ml acetone was slowly added 0.84 ml of phosphoric acid and the mixture stirred at the same temperature overnight. The resulting solid was filtered and dried in a vacuum oven to give 2.46 g of a white solid. The resulting solid was analyzed by XRD and showed Carvedilol dihydrogen phosphate Form I.

Example 16

Preparation of Carvedilol Dihydrogen Phosphate Form I

To a mixture of 5 g of Carvedilol in 75 ml ethanol was slowly added 0.84 ml of phosphoric acid and the mixture was heated to reflux. The mixture was cooled to room temperature and kept at the same temperature overnight. The resulting solid was filtered and dried in a vacuum oven to give 5.22 g of a white solid. The resulting solid was analyzed by XRD and showed Carvedilol dihydrogen phosphate Form I.

Example 17

Preparation of Carvedilol Dihydrogen Phosphate Form I

To a mixture of 5 g of Carvedilol in 120 ml IPA was slowly added 0.84 ml of phosphoric acid and the mixture was heated to reflux. After 1 hour, the mixture was cooled to room temperature and stirred overnight. The resulting solid was filtered and dried in a vacuum oven to give 5.12 g of a white solid. The resulting solid was analyzed by XRD and showed Carvedilol dihydrogen phosphate Form I.

Example 18

Preparation of Carvedilol Dihydrogen Phosphate Form I

To a mixture of 3 g of Carvedilol in 45 ml ethanol was slowly added 0.53 ml of phosphoric acid and the mixture was heated to reflux. To the reflux mixture were added an additional 150 ml of ethanol and 30 ml of water (till complete dissolution). After cooling to room temperature, the mixture was stirred overnight. The resulting solid was filtered and dried in a vacuum oven to give 2.32 g of a white solid. The resulting solid was analyzed by XRD and showed Carvedilol dihydrogen phosphate Form I.

Example 19

Preparation of Carvedilol Dihydrogen Phosphate Form I

To a mixture of 5 g of Carvedilol in 50 ml methanol was slowly added 0.84 ml of phosphoric acid and the mixture was heated to reflux (till complete dissolution). After cooling to room temperature, 20 ml of water were added and the mixture stirred at the same temperature overnight. The resulting solid was filtered and dried in a vacuum oven to give 4.06 g of a white solid. The resulting solid was analyzed by XRD and showed Carvedilol dihydrogen phosphate Form I.

Example 20

Preparation of Carvedilol Dihydrogen Phosphate Form I

To a mixture of 5 g of Carvedilol in 75 ml ethanol was slowly added 0.84 ml of phosphoric acid and the mixture was heated to reflux and 75 ml of water was added (till complete dissolution). The solution was cooled to room temperature and stirred at the same temperature overnight. The resulting solid was filtered and dried in a vacuum oven to give 4 g of a white solid. The resulting solid was analyzed by XRD and showed Carvedilol dihydrogen phosphate Form I.

Example 21

Preparation of Carvedilol Dihydrogen Phosphate Form I

To a mixture of 5 g of Carvedilol in 25 ml THF was slowly added 0.84 ml of phosphoric acid and stirred at room temperature overnight. The resulting solid was filtered and dried in a vacuum oven to give 6 g of a white solid. The resulting solid was analyzed by XRD and showed Carvedilol dihydrogen phosphate Form I.

Example 22

Preparation of Carvedilol Dihydrogen Phosphate Form I

A slurry of 1 g of a mixture of Carvedilol hydrogen phosphate and Carvedilol base in 10 ml acetone was stirred overnight. The resulting solid was filtered and dried in a vacuum oven to give 0.27 g of a white solid. The resulting solid was analyzed by XRD and showed Carvedilol dihydrogen phosphate Form I content.

Example 23

Preparation of Carvedilol Dihydrogen Phosphate Form I

To a mixture of 10 g of Carvedilol in 200 ml absolute ethanol was slowly added 1.7 ml of phosphoric acid and 100 ml of ethanol were slowly distilled out. The solution was cooled to room temperature and stirred at the same temperature overnight. The resulting solid was filtered and dried in a vacuum oven to give 7 g of a white solid. The resulting solid was analyzed by XRD to yield Carvedilol dihydrogen phosphate Form I.

Example 24

Preparation of Carvedilol Dihydrogen Phosphate Form I

To a mixture of 5 g of Carvedilol in 50 ml acetonitrile was slowly added 0.84 ml of phosphoric acid and the mixture was heated to reflux. The solution was cooled to room temperature and stirred at the same temperature for overnight. The resulting solid was filtered and dried in a vacuum oven to give 3.36 g of a white solid. The resulting solid was analyzed by XRD to yield Carvedilol dihydrogen phosphate Form I.

Example 25

Preparation of Carvedilol Dihydrogen Phosphate Form I

To a mixture of 5 g of Carvedilol in 100 ml heptane was slowly added 0.84 ml of phosphoric acid and the mixture was heated to reflux. The mixture was cooled to room temperature and stirred at the same temperature overnight. The resulting solid was filtered and dried in a vacuum oven to give 2.12 g of a white solid. The resulting solid was analyzed by XRD to yield Carvedilol dihydrogen phosphate Form I.

Example 26

Preparation of Carvedilol Dihydrogen Phosphate Form I

To a mixture of 5 g of Carvedilol in 50 ml PGME was slowly added 0.84 ml of phosphoric acid and the mixture was heated to reflux. The solution was cooled to room temperature and stirred at the same temperature overnight. The resulting solid was filtered and dried in a vacuum oven to give 5.17 g of a white solid. The resulting solid was analyzed by XRD to yield Carvedilol dihydrogen phosphate Form I.

Example 27

Preparation of Carvedilol Dihydrogen Phosphate Form I

To a mixture of 5 g of Carvedilol in 100 ml MIBK was slowly added 0.84 ml of phosphoric acid and the mixture was heated to reflux. The mixture was cooled to room temperature and stirred at the same temperature overnight. The resulting solid was filtered and dried in a vacuum oven to give 0.66 g of a white solid. The resulting solid was analyzed by XRD to yield Carvedilol dihydrogen phosphate Form I.

Example 28

Preparation of Carvedilol Dihydrogen Phosphate Form I

To a mixture of 5 g of Carvedilol in 100 ml MEK was slowly added 0.84 ml of phosphoric acid and the mixture was heated to reflux. The mixture was cooled to room temperature and stirred at the same temperature overnight. The resulting solid was filtered and dried in a vacuum oven to give 5.65 g of a white solid. The resulting solid was analyzed by XRD to yield Carvedilol dihydrogen phosphate Form I.

Example 29

Preparation of Carvedilol Dihydrogen Phosphate Form I

To a mixture of 5 g of Carvedilol in 50 ml 2-BuOH was slowly added 0.84 ml of phosphoric acid and the mixture was heated to reflux. The solution was cooled to room temperature and stirred at the same temperature overnight. The resulting solid was filtered and dried in a vacuum oven to give 3.89 g of a white solid. The resulting solid was analyzed by XRD to yield Carvedilol dihydrogen phosphate Form I.

Example 30

Preparation of Carvedilol Dihydrogen Phosphate Form I

To a mixture of 5 g of Carvedilol in 50 ml n-BuOH was slowly added 0.84 ml of phosphoric acid and the mixture was heated to reflux. The solution was cooled to room temperature and stirred at the same temperature for 5 hours. The resulting solid was filtered and dried in a vacuum oven to give 0.30 g of a white solid. The resulting solid was analyzed by XRD to yield Carvedilol dihydrogen phosphate Form I.

Example 31

Preparation of Carvedilol Dihydrogen Phosphate Form I

To a mixture of 5 g of Carvedilol in 150 ml tert-BuOH was slowly added 0.84 ml of phosphoric acid and the mixture was heated to reflux. The mixture was cooled to room temperature and stirred at the same temperature over the weekend. The resulting solid was filtered and dried in a vacuum oven to give 2.74 g of a white solid. The resulting solid was analyzed by XRD to yield Carvedilol dihydrogen phosphate Form I.

Example 32

Preparation of Carvedilol Dihydrogen Phosphate Form I

To a mixture of 8 g of Carvedilol in 80 ml n-propanol was slowly added 1.34 ml of phosphoric acid and the mixture stirred at room temperature overnight. The resulting solid was filtered and dried in a vacuum oven to give 5.67 g of a white solid. The resulting solid was analyzed by XRD and showed Carvedilol dihydrogen phosphate Form I.

Example 33

Preparation of Carvedilol Dihydrogen Phosphate Form I

To a mixture of 8 g of Carvedilol in 80 ml of methyl acetate was slowly added 1.34 ml of phosphoric acid and the mixture stirred at room temperature overnight. The resulting solid was filtered and dried in a vacuum oven to give 5.13 g of a white solid. The resulting solid was analyzed by XRD and showed Carvedilol dihydrogen phosphate Form I.

Example 34

Preparation of Carvedilol Dihydrogen Phosphate Form I

To a mixture of 8 g of Carvedilol in 80 ml isobutyl acetate was slowly added 1.34 ml of phosphoric acid and the mixture was heated to reflux. After 2 hour, the mixture was cooled to room temperature and stirred overnight. The resulting solid was filtered and dried in a vacuum oven to give 7.5 g of a white solid. The resulting solid was analyzed by XRD and showed Carvedilol dihydrogen phosphate Form I.

Example 35

Preparation of Carvedilol Dihydrogen Phosphate Form I

To a mixture of 8 g of Carvedilol in 80 ml ethyl acetate was slowly added 1.34 ml of phosphoric acid and the mixture was heated to reflux. After 2 hour, the mixture was cooled to room temperature and stirred overnight. The resulting solid was filtered and dried in a vacuum oven to give 7.2 g of a white solid. The resulting solid was analyzed by XRD and showed Carvedilol dihydrogen phosphate Form I.

Example 36

Preparation of Carvedilol Dihydrogen Phosphate Form I

To a mixture of 8 g of Carvedilol in 80 ml MTBE was slowly added 1.34 ml of phosphoric acid and the mixture was heated to reflux. After 2 hour, the mixture was cooled to room temperature and stirred overnight. The resulting solid was filtered and dried in a vacuum oven to give 7.7 g of a white solid. The resulting solid was analyzed by XRD and showed Carvedilol dihydrogen phosphate Form I.

Example 37

Preparation of Carvedilol Dihydrogen Phosphate Form I

A 50 ml flask was charged with 1 g of Carvedilol dihydrogen phosphate Form R and 10 ml EtOH abs. The mixture was stirred at room temperature for 24 hours until the crystals were converted to Form I. The crystals were collected by filtration under reduced pressure and dried at 50° C. under reduced pressure (under 100 mmHg). The resulting solid was analyzed by XRD and showed Carvedilol dihydrogen phosphate Form I.

Example 38

Preparation of Carvedilol Dihydrogen Phosphate Form L

A mixture of 4 g of Carvedilol dihydrogen phosphate in 40 ml of dioxane was heated to reflux overnight. After cooling to room temperature, the resulting solid was filtered and dried in a vacuum oven at 45° C. to give 3.88 g of a white solid. The resulting solid was analyzed by XRD and showed Carvedilol dihydrogen phosphate Form L.

Example 39

Preparation of Carvedilol Dihydrogen Phosphate Form L

To a solution of 4 g of Carvedilol in 60 ml dioxane was slowly added 0.67 ml of phosphoric acid and the resulting mixture was heated to reflux (an additional 20 ml of dioxane were added). After overnight the mixture was cooled to room temperature, and stirred for overnight. The resulting solid was filtered and dried in a vacuum oven to give 3.45 g (64.32% chemical yield) of a white solid. The resulting solid was analyzed by XRD to yield Carvedilol dihydrogen phosphate Form L.

Example 40

Preparation of Carvedilol Dihydrogen Phosphate Form L1

A mixture of 30 g of Carvedilol dihydrogen phosphate in 300 ml of dioxane was heated to reflux overnight. After cooling to room temperature, the resulting solid was filtered and dried in a vacuum oven at 55° C. to give 29 g of a white solid. The resulting solid was analyzed by XRD and showed Carvedilol dihydrogen phosphate Form L1.

Example 41

Preparation of carvedilol dihydrogen phosphate Form O

Form O was prepared by grinding about 200 mg of amorphous form with 2-3 drops of water for about 1-2 min (using mortar and pestle).

Example 42

Preparation of Carvedilol Dihydrogen Phosphate Form P

A mixture of 5 g of amorphous Carvedilol dihydrogen phosphate in 50 ml of ethanol was stirred at room temperature overnight. The resulting solid was filtered and dried in a vacuum oven at 55° C. to give 3.4 g of a white solid. The resulting solid was analyzed by XRD and showed Carvedilol dihydrogen phosphate Form P.

Example 43

Preparation of Amorphous Carvedilol Dihydrogen Phosphate 10 g of Carvedilol dihydrogen phosphate was dissolved in 200 ml of methanol at reflux. The solution was sprayed (72 [ml/h]) into the chamber of a spray drying apparatus with ambient nitrogen (38 m$^3$/h, 100° C.) at co-current flow. The atomizing flow (660[l/h]) of nitrogen produced droplets, which led to a high evaporation rate. The temperature of the outlet solids was 37° C. The obtained sample was analyzed by XRD and found to be amorphous.

Example 44

Preparation of Amorphous Carvedilol Dihydrogen Phosphate 10 g of carvedilol dihydrogen phosphate was dissolved in 200 ml of acetone/water (2:1) at reflux. The solution was sprayed (72 [ml/h]) into the chamber of a spray drying apparatus with ambient nitrogen (38 m$^3$/h, 100° C.) at co-current flow. The atomizing flow (660[l/h]) of nitrogen produced droplets, which led to a high evaporation rate. The temperature of the outlet solids was 33-35° C. The obtained sample was analyzed by XRD and found to be amorphous.

Example 45

Preparation of Amorphous Carvedilol Dihydrogen Phosphate 5 g of Carvedilol dihydrogen phosphate was dissolved in 100 ml of methanol at reflux. The solution was sprayed (72 [ml/h]) into the chamber of a spray drying apparatus with ambient nitrogen (38 m$^3$/h, 80° C.) at co-current flow. The atomizing flow (660[l/h]) of nitrogen produced droplets, which led to a high evaporation rate. The temperature of the outlet solids was 19° C. The obtained sample was analyzed by XRD and found to be amorphous.

Example 46

Preparation of Amorphous Carvedilol Dihydrogen Phosphate 5 g of Carvedilol dihydrogen phosphate was dissolved in 100 ml of methanol. The solution was sprayed (72 [ml/h]) into the chamber of a spray drying apparatus with ambient nitrogen (38 m$^3$/h, 100° C.) at co-current flow. The atomizing flow (660[l/h]) of nitrogen produced droplets, which led to a high evaporation rate. The temperature of the outlet solids was 40° C. The obtained sample was analyzed by XRD and found to be amorphous.

Example 47

Preparation of Amorphous Carvedilol Dihydrogen Phosphate 100 g of dry Carvedilol were charged into a 5 liter stainless steel lab dryer equipped with a mechanical stirrer, and a controlled heating/cooling system. 1000 ml of methanol were charged and 17 ml of 85% phosphoric acid was introduced into the dryer. The agitator was turned on, and suspension was obtained. The jacket temperature was adjusted to 70° C. and at 58° C. clear solution was obtained. The solution was heated to reflux and was mixed for 15 minutes.

The solution was dried under reduced pressure (the pressure was reduced gradually from atmospheric pressure down to 40 mmHg) at 70° C. until a dried product was obtained.

20 g of the product were further dried at 50° C., under reduced pressure (under 100 mmHg). 16 g of white solid were obtained. The resulting solid was analyzed by XRD and showed Amorphous Carvedilol dihydrogen phosphate.

Example 48

Preparation of Carvedilol Dihydrogen Phosphate Form N

Carvedilol dihydrogen phosphate Form L, L1 and amorphous carvedilol dihydrogen phosphate were exposed to 100% relative humidity (RH) for 7 days at room temperature. According to XRD, the exposed samples are carvedilol dihydrogen phosphate Form N.

Example 49

Preparation of a Mixture of Carvedilol Dihydrogen Phosphate Form I and Form N 100 g of dry Carvedilol were charged into a 5 liter stainless steel lab dryer equipped with a mechanical stirrer and a controlled heating/cooling system. 350 ml of acetone and 150 ml of water were charged and 17 ml of 85% phosphoric acid was introduced into the dryer. The agitator was turned on and suspension was obtained. The jacket temperature was adjusted to 70° C. and at about 60° C. a clear solution was obtained.

The solution was dried under reduced pressure (the pressure was reduced gradually from atmospheric pressure down to 40 mmHg) at a jacket temp of 70° C. until a dried product was obtained.

The resulting solid was analyzed by XRD and showed a Carvedilol dihydrogen phosphate mixture of Form I and Form N.

Example 50

Preparation of Carvedilol Dihydrogen Phosphate Form F 40 g of dry Carvedilol were charged into a 1 liter glass lab reactor equipped with a mechanical stirrer and a controlled heating/cooling system. 400 ml of methanol were charged. The agitator was turned on and a suspension was obtained. The temperature was adjusted to 50° C. and 6.8 ml of 85% phosphoric acid was introduced into the reactor. The solution was heated to reflux and was mixed for 3 hours until Carvedilol dihydrogen phosphate precipitated. The precipitated product was slurried for 1 hr and then the product was isolated by filtration under reduced pressure. The filtered cake was washed with 40 ml of methanol. 10 g of the wet product were dried in a tray oven at 50° C., under reduced pressure. 8 g of white solid were obtained. The resulting solid was analyzed by XRD and showed Carvedilol dihydrogen phosphate Form F.

Example 51

Preparation of Carvedilol Dihydrogen Phosphate Form F 20 g of dry Carvedilol base were charged into 0.5 liter glass reactor equipped with mechanical stirrer, and controlled heating/cooling system. 300 ml of Methanol were charged. The agitator was turned on, the solution was heated to 50° C. and partial dissolution was obtained, 3.4 ml of 85% phosphoric acid were introduced into the reactor.

The jacket temperature was adjusted to 75° C. (at 54° C. a full dissolution was obtained). The solution was heated and stirred for 16 hours during which the product precipitated.

The product was filtered and the cake product was dried in a Vacuum oven under reduced pressure (under 100 mmHg) at 55° C. until a dried product was obtained. The dry sample was analyzed by XRD and found to be carvedilol dihydrogen phosphate Form F.

Example 52

Preparation of Carvedilol Dihydrogen Phosphate Form F

A 100 ml flask was charged with Carvedilol dihydrogen phosphate Form I (2 g) and methanol (20 ml). The suspension was heated to reflux and stirred for 30 min to obtain a clear solution. The solution was further stirred at reflux until precipitation was observed and then cooled to room temperature and stirred for an additional hour.

The crystals were collected by filtration under reduced pressure and dried at 50° C. under reduced pressure to obtain Carvedilol dihydrogen phosphate. (1.7 g)

The dry sample was analyzed by XRD and found to be carvedilol dihydrogen phosphate Form F.

Example 53

Preparation of Carvedilol Dihydrogen Phosphate Form F1

50 g of dry Carvedilol base were charged into 1 liter glass reactor equipped with mechanical stirrer, and controlled heating/cooling system. 750 ml of EtOH abs (Ethanol absolute) were charged and 8.5 ml of 85% phosphoric acid was introduced into the reactor. The agitator was turned on, and suspension was obtained. The jacket temperature was adjusted to 80° C. The suspension was heated and stirred for 4 hours, cooled to 15° C. and stirred for 2 hours, filtered and washed with 50 ml EtOH abs.

The cake product was dried in a Vacuum oven under a reduced pressure from amt under 100 mmHg) at 55° C. until a dried product was obtained.

The dry sample was analyzed by XRD and found to be carvedilol dihydrogen phosphate Form F1.

Example 54

Preparation of Carvedilol Dihydrogen Phosphate Form F1

20 g of dry Carvedilol dihydrogen Phosphate Form I were charged into 1 liter glass reactor equipped with mechanical stirrer, and controlled heating/cooling system.

300 ml of EtOH abs (Ethanol absolute) were charged into the reactor, The agitator was turned on, and suspension was obtained. The jacket temperature was adjusted to 80° C. The suspension was heated and stirred for 15.5 hours, cooled to 15° C. and stirred for 2 hours and filtered.

The cake product was dried in a vacuum oven under a reduced pressure from atm (under 100 mmHg) at 80° C. until a dried product was obtained.

The resulting solid was analyzed by XRD and showed Carvedilol dihydrogen phosphate Form F1.

Example 55

Preparation of Carvedilol Dihydrogen Phosphate Form F1

20 g of dry Carvedilol dihydrogen Phosphate Form R were charged into a 1 liter glass reactor equipped with mechanical stirrer, and controlled heating/cooling system.

300 ml of EtOH abs (Ethanol absolute) were charged into the reactor. The agitator was turned on, and suspension was obtained. The jacket temperature was adjusted to 80° C. The suspension was heated and stirred for 15.5 hours, cooled to 15° C., and stirred for 2 hours and filtered.

The cake product was dried in a vacuum oven under a reduced pressure from atm (under 100 mmHg) at 80° C. until a dried product was obtained.

The resulting solid was analyzed by XRD and showed Carvedilol dihydrogen phosphate Form F1.

Example 56

Preparation of Carvedilol Dihydrogen Phosphate Form R 50 g of dry Carvedilol base were charged into 1 liter glass reactor equipped with mechanical stirrer, and controlled heating/cooling system. 750 ml of IPA (isopropyl alcohol) were charged and 8.5 ml of 85% phosphoric acid was introduced into the reactor. The agitator was turned on, and suspension was obtained. The jacket temperature was adjusted to 25° C. The suspension was stirred for 4 hours at 25° C., cooled to 15° C., stirred for 2 hours, filtered and washed with 50 ml IPA.

The cake product was dried in a Vacuum oven under a reduced pressure from (under 100 mmHg) at 55° C. until a dried product was obtained.

The dry sample was analyzed by XRD and found to be carvedilol dihydrogen phosphate Form R.

Example 57

Preparation of Carvedilol Dihydrogen Phosphate Form R 50 g of dry Carvedilol base were charged into 1 liter glass reactor equipped with mechanical stirrer, and controlled heating/cooling system. 250 ml of IPA (isopropyl alcohol) were charged and 8.5 ml of 85% phosphoric acid was introduced into the reactor. The agitator was turned on, and suspension was obtained. The jacket temperature was adjusted to 52.5° C. The suspension was heated and stirred for 2 hours, cooled to 15° C., stirred for 2 hours, filtered and washed with 50 ml IPA.

The cake product was dried in a Vacuum oven under a reduced pressure from (under 100 mmHg) at 55° C. until a dried product was obtained.

The dry sample was analyzed by XRD and found to be carvedilol dihydrogen phosphate Form R including traces of Form I.

Example 58

Preparation of Carvedilol Dihydrogen Phosphate Form R

A 50 ml flask was charged with 1 g of Carvedilol dihydrogen phosphate amorphous and 10 ml IPA. The mixture was stirred at room temperature for 24 hours until the crystals were converted to Form R. The crystals were collected by filtration under reduced pressure and dried at 50° C. under reduced pressure (under 100 mmHg).

The resulting solid was analyzed by XRD and showed Carvedilol dihydrogen phosphate Form R.

Example 59

Preparation of Carvedilol Dihydrogen Phosphate Form R

A 50 ml flask was charged with 1 g of Carvedilol dihydrogen phosphate Form F1 and 10 ml IPA. The mixture was stirred at room temperature for 24 hours until the crystals were converted to Form R. The crystals were collected by filtration under reduced pressure and dried at 50° C. under reduced pressure (under 100 mmHg).

The resulting solid was analyzed by XRD and showed Carvedilol dihydrogen phosphate Form R.

Example 60

Preparation of Carvedilol Dihydrogen Phosphate Form Y 450 g of dry Carvedilol were charged into a 10 liter glass reactor equipped with mechanical stirrer, and controlled heating/cooling system. 6,750 ml of EtOH abs (Ethanol absolute) were charged and 768.5 ml of 85% phosphoric acid was introduced into the reactor. The agitator was turned on and suspension was obtained. The jacket temperature was adjusted to 80° C. The suspension was heated and stirred. A sample from the suspension was taken after 3 hours and then was filtered.

The wet sample was analyzed by XRD and found to be carvedilol dihydrogen phosphate Form Y.

Examples to Obtain Essentially Form I

Example 61

Carvedilol dihydrogen phosphate Form F was exposed to 100% relative humidity (RH) for 7 days at 60° C. According to XRD, the resulting exposed sample is carvedilol dihydrogen phosphate Form I.

Example 62

Carvedilol dihydrogen phosphate Form N was placed in oven at a temperature of 120° C. for 30 min. The resulting solid was analyzed by XRD and showed a Carvedilol dihydrogen phosphate Form I.

Example 63

A 50 ml flask is charged with 1 gr of Carvedilol dihydrogen phosphate Form F1 and 10 ml Acetone. The mixture is stirred at room temperature for 1 day while which the crystals are converted to Form I. The crystals are collected by filtration under reduced pressure and dried at 80° C. under reduced pressure (under 100 mmHg).

The resulting solid was analyzed by XRD and showed Carvedilol dihydrogen phosphate FORM I.

Example 64

A 50 ml flask is charged with 1 gr of Amorphous Carvedilol dihydrogen phosphate and 10 ml Acetone. The mixture is stirred at room temperature for 1 day until the crystals are converted to Form I. The crystals are collected by filtration under reduced pressure and dried at 80° C. under reduced pressure (under 100 mmHg).

The resulting solid was analyzed by XRD and showed Carvedilol dihydrogen phosphate Form I.

Example 65

A 50 ml flask is charged with 1 gr of Carvedilol dihydrogen phosphate Form R and 10 ml Acetone. The mixture is stirred at room temperature for 1 day until the crystals are converted to Form I. The crystals are collected by filtration under reduced pressure and dried at 80° C. under reduced pressure (under 100 mmHg).

The resulting solid was analyzed by XRD and showed Carvedilol dihydrogen phosphate FORM I.

Example 66

A 100 ml flask is charged with 7 gr of Carvedilol dihydrogen phosphate Form N and 70 ml Acetone. The mixture is stirred at room temperature for 1 day while which the crystals are converted to Form I. The crystals are collected by filtration under reduced pressure and dried at 50° C. under reduced pressure (under 100 mmHg).

The resulting solid was analyzed by XRD and showed Carvedilol dihydrogen phosphate FORM I.

Example 67

Carvedilol dihydrogen phosphate Form L1 was placed in oven at a temperature of about between 80-120° C. for 30 min. The resulting solid was analyzed by XRD and showed a Carvedilol dihydrogen phosphate Form I.

Example 68

Amorphous Carvedilol dihydrogen phosphate was placed in oven at a temperature of 120° C. for 30 min. The resulting solid was analyzed by XRD and showed a Carvedilol dihydrogen phosphate Form I.

Example 69

40 ml of water was added to 4 gr Carvedilol dihydrogen phosphate Form I (MAB-1449). The mixture was slurred at room temperature over night.

The suspension was vacuum filtered and dried in vacuum at 50° C. in oven over night to obtain 3.13 gr (78% yield). The resulting solid was analyzed by XRD and showed a mixture of carvedilol dihydrogen phosphate Form I and carvedilol hydrogen phosphate Form G.

Example 70

Carvedilol dihydrogen phosphate Form P was placed in oven at a temperature of about between 80-120° C. for about 30 min. The resulting solid was analyzed by XRD and showed a Carvedilol dihydrogen phosphate Form I.

Example 71

Carvedilol dihydrogen phosphate Form R was placed in oven at a temperature of about 120° C. for about 30 min. The resulting solid was analyzed by XRD and showed a Carvedilol dihydrogen phosphate Form I.

Example 72

Carvedilol dihydrogen phosphate Form N was pressed by pressure of 2 ton by a laboratory press for about 1 min. The resulting solid was analyzed by XRD and showed a Carvedilol dihydrogen phosphate mixture of Form N and Form I.

Example 73

Carvedilol dihydrogen phosphate Form P was pressed by pressure of 2 ton by a laboratory press for about 1 min. The resulting solid was analyzed by XRD and showed a Carvedilol dihydrogen phosphate Form I.

Example 74

Carvedilol dihydrogen phosphate Form P was ground by mortal and pestle for about 1 min. The resulting solid was analyzed by XRD and showed a Carvedilol dihydrogen phosphate Form I.

Example 75

Carvedilol dihydrogen phosphate Form F was ground by mortal and pestle with 2-3 drops of butanol for about 1 min. The resulting solid was analyzed by XRD and showed a Carvedilol dihydrogen phosphate mixture of Form F and Form I.

Example 76

Amorphous Carvedilol dihydrogen phosphate was placed in an atmosphere of the following solvents for 7 days: n-propanol, iso-propanol, butanol, acetone and ethyl acetate. The resulting solids were analyzed by XRD and showed a Carvedilol dihydrogen phosphate mixture of amorphous form and Form I for n-propanol, iso-propanol, butanol, acetone and ethyl acetate.

Example 77

A 50 ml flask is charged with 0.6 gr of Carvedilol dihydrogen phosphate Form N and 6 ml water. The mixture is stirred at room temperature for 3 days until part of the crystals are converted to Form I. The crystals are collected by filtration under reduced pressure and dried at 50° C. under reduced pressure (under 100 mmHg).

The resulting solid was analyzed by XRD and showed a mixture of Carvedilol dihydrogen phosphate FORM N and Form I.

Examples to Obtain Essentially Amorphous Form (1:1)

Example 78

Carvedilol dihydrogen phosphate Form F was placed in oven at a temperature of about 140° C. for about 30 min. The resulting solid was analyzed by XRD and showed an amorphous form of Carvedilol dihydrogen phosphate.

Example 79

Carvedilol dihydrogen phosphate Form R was placed in oven at a temperature of about 100° C. for about 30 min. The resulting solid was analyzed by XRD and showed a mixture of Carvedilol dihydrogen phosphate Form R and amorphous form.

Example 80

Solid pharmaceutical compositions of amorphous form and the following excipients: lactose monohydrate, sucrose and avicel were compacted into a dosage form like a tablet.

Examples to Obtain Form N (1:1)

Example 81

Carvedilol dihydrogen phosphate Form F1 was exposed to 100% relative humidity (RH) for 7 days at room temperature. The resulting solid was analyzed by XRD and showed a Carvedilol dihydrogen phosphate mixture of Form N and Form F1.

Example 82

Carvedilol dihydrogen phosphate Form R was exposed to 100% relative humidity (RH) for 7 days at room temperature. According to XRD, the exposed sample is Carvedilol dihydrogen phosphate Form N.

Example 83

Carvedilol dihydrogen phosphate Form F1 was exposed to 100% relative humidity (RH) for 7 days at room temperature. The resulting solid was analyzed by XRD and showed a Carvedilol dihydrogen phosphate mixture of Form F1 and Form N.

Example 84

Carvedilol dihydrogen phosphate Form N was placed in oven at a temperature of 80° C. for 30 min. The resulting solid was analyzed by XRD and showed a Carvedilol dihydrogen phosphate mixture of amorphous form and Form N.

Example 85

Solid pharmaceutical compositions of Form N and the following excipients: lactose monohydrate, sucrose and avicel were compacted into a dosage form like a tablet.

Examples to Obtain Form F1 (1:1)

Example 86

A 50 ml flask is charged with 0.6 gr of Carvedilol dihydrogen phosphate Form N and 6 ml EtOH. The mixture is stirred at room temperature for 3 days until the crystals are converted to Form F1. The crystals are collected by filtration under reduced pressure and dried at 50° C. under reduced pressure (under 100 mmHg).

The resulting solid was analyzed by XRD and showed Carvedilol dihydrogen phosphate FORM F1.

Example 87

30 gr (on dry basis) of wet Carvedilol base were charged into 1 liter glass reactor equipped with mechanical stirrer, and controlled heating/cooling system. 810 ml of EtOH abs (Ethanol absolute) were charged, the agitator was turned on and the reactor content was heated to reflux (78-82° C.), during the heating full dissolution was achieved.

5.6 ml of 85% phosphoric acid and 90 ml of EtOH abs. were introduced into the reactor. Seeding was preformed with 0.15 gr Carvedilol dihydrogen phosphate FORM F1 slurried in 8 ml EtOH abs. The reactor content was stirred for 4 hr, cooled to 15° C. stirred for another 2 hr, filtered and washed with 60 ml ETOH abs.

The cake product was dried in a vacuum oven under a reduced pressure (under 100 mmHg) at 50° C. until a dried product was obtained.

The resulting solid was analyzed by XRD and showed Carvedilol dihydrogen phosphate Carvedilol dihydrogen phosphate FORM F1.

Example 88

Solid pharmaceutical compositions of Form F1 and the following excipients: lactose monohydrate, sucrose and avicel were compacted into a dosage form like a tablet.

Examples to Obtain Form R (1:1)

Example 89

A 50 ml flask is charged with 0.6 gr of Carvedilol dihydrogen phosphate Form N and 6 ml IPA. The mixture is stirred at room temperature for 3 days while which the crystals are converted to Form R. The crystals are collected by filtration under reduced pressure and dried at 50° C. under reduced pressure (under 100 mmHg). The resulting solid was analyzed by XRD and showed Carvedilol dihydrogen phosphate FORM R.

Example 90

Solid pharmaceutical compositions of Form R and the following excipients: lactose monohydrate, sucrose and avicel were compacted into a dosage form like a tablet.

Example 91

Process for the Preparation of Carvedilol Dihydrogen Phosphate Form F2

Carvedilol dihydrogen phosphate Form I was used for crystallization. Sample (40 mg) was dissolved in ethanol (4 ml, Merck 1.11727.2500) at 70° C. The flask was placed at the thermos flask at 50° C. and was allowed to cool slowly to 20° C. within 6 days. Data collection was preformed at 150 K.

Process for the Preparation of Form Q

Example 92

Carvedilol hydrogen phosphate Form K was exposed to 0% relative humidity (RH) for 7 days at room temperature. The resulting solid was analyzed by XRD and showed Form Q content.

Example 93

Process for the Preparation of Carvedilol Phosphate Salt Phosphate Form W

Carvedilol dihydrogen phosphate form F1, sample LL-11193, was added to 30 ml of 0.1 M $KH_2PO_4$ (pH=7.0 adjusted with 1M KOH) until a suspension was obtained. The suspension was stirred at was stirred at 25° C. for 24 hr and filtered under vacuum. XRD analysis showed that it was a new crystal form (designated Form W).

What is claimed is:

1. A crystalline form of carvedilol dihydrogen phosphate characterized by data selected from the group consisting of:
    (a) X-ray powder diffraction reflections at about: 7.6, 9.8, 10.9, 21.2 and 25.0 degrees two theta±0.2 degrees two theta;
    (b) any five peaks selected from the following list of PXRD peaks at about: 7.6, 8.5, 9.8, 10.9, 12.0, 13.3, 15.2 and 16.9±0.2 degrees two theta;
    (c) X-ray powder diffraction reflections at about: 7.6, 10.9, 13.3, 15.2 and 18.8 degrees two theta±0.2 degrees two theta;
    d) X-ray powder diffraction reflections at about: 7.6, 8.5, 9.8, 15.2 and 16.9±0.2 degrees two theta;
    (e) X-ray powder diffraction reflections at about: 7.6, 9.8, 10.9, 14.7, 15.2 and 22.8±0.2 degrees two theta;
    (f) X-ray powder diffraction reflections at about: 7.6, 8.5, 9.8, 13.3 and 15.2±0.2 degrees two theta; and
    (g) an X-ray powder diffraction pattern substantially as depicted in FIG. 26 or FIG. 27.

2. The crystalline form carvedilol dihydrogen phosphate of claim 1 characterized by X-ray powder diffraction reflections at about: 7.6, 9.8, 10.9, 21.2 and 25.0 degrees two theta±0.2 degrees two theta.

3. The crystalline form carvedilol dihydrogen phosphate of claim 1 characterized by any five peaks selected from the following list of PXRD peaks at about: 7.6, 8.5, 9.8, 10.9, 12.0, 13.3, 15.2 and 16.9±0.2 degrees two theta.

4. The crystalline form carvedilol dihydrogen phosphate of claim 1 characterized by X-ray powder diffraction reflections at about: 7.6, 10.9, 13.3, 15.2 and 18.8 degrees two theta±0.2 degrees two theta.

5. The crystalline form carvedilol dihydrogen phosphate of claim 1 characterized by X-ray powder diffraction reflections at about: 7.6, 8.5, 9.8, 15.2 and 16.9±0.2 degrees two theta.

6. The crystalline form carvedilol dihydrogen phosphate of claim 1 characterized by X-ray powder diffraction reflections at about: 7.6, 9.8, 10.9, 14.7, 15.2 and 22.8±0.2 degrees two theta.

7. The crystalline form carvedilol dihydrogen phosphate of claim 1 characterized by X-ray powder diffraction reflections at about: 7.6, 8.5, 9.8, 13.3 and 15.2±0.2 degrees two theta.

8. The crystalline form carvedilol dihydrogen phosphate of claim 1, further characterized by a solid-state $^{13}$C-NMR spectrum having chemical shift resonances at about 155.3, 145.3 and 127.7±0.2 ppm.

9. The crystalline form carvedilol dihydrogen phosphate of claim 1, further characterized by a solid-state $^{13}$C NMR spectrum having chemical shift differences between the lowest ppm resonance in the chemical shift area of 100 to 180 ppm and another in the chemical shift area of 100 to 180 ppm of about 52.6, 42.6 and 25±0.1 ppm.

10. The crystalline form carvedilol dihydrogen phosphate of claim 1 characterized by an X-ray powder diffraction pattern substantially as depicted in FIG. 26 or FIG. 27.

11. The crystalline form carvedilol dihydrogen phosphate of claim 1, further characterized by a solid-state $^{13}$C NMR spectrum substantially as depicted in FIG. 28 or 28a.

12. The crystalline form carvedilol dihydrogen phosphate of claim 1 containing less than about 20% by weight of other crystalline forms of carvedilol and carvedilol phosphate salts.

13. The crystalline form carvedilol dihydrogen phosphate of claim 1 containing less than about 20% by weight of crystalline carvedilol dihydrogen phosphate Form I; wherein carvedilol dihydrogen phosphate Form I is characterized by X-ray powder diffraction reflections at about: 7.0, 8.0, 11.4 and 16.0 degrees two theta±0.2 degrees two theta.

14. The crystalline form carvedilol dihydrogen phosphate of claim 12 containing less than about 10% by weight of other crystalline forms of carvedilol and carvedilol phosphate salts.

15. The crystalline form carvedilol dihydrogen phosphate of claim 14 containing less than about 5% by weight of other crystalline forms of carvedilol and carvedilol phosphate salts.

16. The crystalline form carvedilol dihydrogen phosphate of claim 15 containing less than about 1% by weight of other crystalline forms of carvedilol and carvedilol phosphate salts.

17. The crystalline form carvedilol dihydrogen phosphate of claim 13 containing less than about 10% by weight of crystalline carvedilol dihydrogen phosphate Form I.

18. The crystalline form carvedilol dihydrogen phosphate of claim 17 containing less than about 5% by weight of crystalline carvedilol dihydrogen phosphate Form I.

19. The crystalline form carvedilol dihydrogen phosphate of claim 18 containing less than about 1% by weight of crystalline carvedilol dihydrogen phosphate Form I.

* * * * *